United States Patent
Gerlach et al.

(10) Patent No.: US 10,329,292 B2
(45) Date of Patent: Jun. 25, 2019

(54) SUBSTITUTED XANTHINE DERIVATIVES

(71) Applicants: Boehringer Ingelheim International GmbH, Ingelheim am Rhein (DE); Hydra Biosciences, Inc., Cambridge, MA (US)

(72) Inventors: Kai Gerlach, Ingelheim am Rhein (DE); Christian Eickmeier, Ingelheim am Rhein (DE); Achim Sauer, Ingelheim am Rhein (DE); Stefan Just, Ingelheim am Rhein (DE); Bertrand L. Chenard, Waterford, CT (US)

(73) Assignees: Boehringer Ingelheim International GmbH, Ingelheim am Rhein (DE); Hydra Biosciences, Inc., Cambridge, MA (US)

( * ) Notice: Subject to any disclaimer, the term of this patent is extended or adjusted under 35 U.S.C. 154(b) by 0 days.

(21) Appl. No.: 16/031,399

(22) Filed: Jul. 10, 2018

(65) Prior Publication Data

US 2019/0016722 A1     Jan. 17, 2019

(30) Foreign Application Priority Data

Jul. 11, 2017 (EP) .................................. 17180721

(51) Int. Cl.
*C07D 473/06*     (2006.01)
*A61P 25/28*     (2006.01)
*A61P 25/30*     (2006.01)
*A61P 25/22*     (2006.01)
*A61P 25/18*     (2006.01)
*A61P 25/24*     (2006.01)
*A61K 31/519*     (2006.01)
*A61K 31/522*     (2006.01)
*C07D 487/04*     (2006.01)

(52) U.S. Cl.
CPC .......... *C07D 473/06* (2013.01); *A61K 31/519* (2013.01); *A61K 31/522* (2013.01); *A61P 25/18* (2018.01); *A61P 25/22* (2018.01); *A61P 25/24* (2018.01); *A61P 25/28* (2018.01); *A61P 25/30* (2018.01); *C07D 487/04* (2013.01); *A61K 2121/00* (2013.01)

(58) Field of Classification Search
None
See application file for complete search history.

(56) References Cited

U.S. PATENT DOCUMENTS

| | | | |
|---|---|---|---|
| 6,869,947 B2 * | 3/2005 | Kanstrup | C07D 473/02 514/217.06 |
| 2002/0198205 A1 * | 12/2002 | Himmelsbach | C07D 473/04 514/234.5 |
| 2014/0275071 A1 * | 9/2014 | Chenard | C07D 473/04 514/234.2 |
| 2017/0050966 A1 * | 2/2017 | Lippa | C07D 473/08 |

FOREIGN PATENT DOCUMENTS

WO     WO-2014143799 A2 *     9/2014     .......... C07D 473/04

* cited by examiner

*Primary Examiner* — Nyeemah A Grazier
(74) *Attorney, Agent, or Firm* — Wolf, Greenfield & Sacks, P.C.

(57) ABSTRACT

The present invention relates to substituted xanthine derivatives, pharmaceutical compositions containing them and their use in therapy, particularly in the treatment of conditions having an association with TRPC5 containing ion channels.

18 Claims, No Drawings

SUBSTITUTED XANTHINE DERIVATIVES

CROSS REFERENCE TO RELATED APPLICATION(S)

The present application claims priority to European Application No. EP 17 180 721.7, filed Jul. 11, 2017, which is incorporated herein by reference in its entirety.

FIELD OF THE INVENTION

The present invention relates to substituted xanthine derivatives, pharmaceutical compositions containing them and their use in therapy, particularly in the treatment or prevention of conditions having an association with TRPC5 containing ion channels.

BACKGROUND OF THE INVENTION

A variety of ion channel proteins exist to mediate ion flux across cellular membranes. The proper expression and function of ion channel proteins is essential for the maintenance of cell function, and the intracellular communication. Numerous diseases are the result of mis-regulation of membrane potential or aberrant calcium handling. Given the central importance of ion channels in modulating membrane potential and ion flux in cells, identification of agents that can promote or inhibit particular ion channels are of great interest as research tools and as possible therapeutic agents.

Cation channels such as the transient receptor potential (TRP) cation channel subfamily C, member 5 (TRPC5) modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPC5 also alters the intracellular free calcium concentration. Calcium is a ubiquitous second messenger molecule within the cell and the alterations in intracellular calcium levels have profound effects on signal transduction and gene expression. Thus, activation of non-selective cation channels such as TRPC5 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Homomeric TRPC5 ion channels are signal transduction gated, Ca2+-permeable channels predominantly expressed in neurons. TRPC5 forms homomultimeric structures such as tetramers (i.e., TRPC5 homomultimers) and heteromultimeric structures such as tetramers (i.e., TRPC5-TRPC1 heteromultimers). Unless expressly stated otherwise, when the term TRPC5 is used herein, for example, when identifying a modulator of TRPC5 such as a TRPC5 antagonist, the term TRPC5 is used generically so as to include either or both of a TRPC5 homomultimer or a heteromultimer (e.g. TRPC5-TPRC1 or TRPC5-TRPC4 heteromultimer). Examples of TRPC5 in the literature include the following: Nature 2008 Jan. 3; 451 (7174):69-72; Mol Pharmacol. 2008 January; 73 (1):42-9; J Biol Chem. 2007 Nov. 16; 282 (46):33868-78; Biochem Biophys Res Commun. 2008 Jan. 11; 365 (2):239-45; J Biol Chem. 2006 Nov. 3; 281 (44): 33487-96; Eur J Pharmacol. 2005 Mar. 14; 510 (3):217-22; J Biol Chem. 2006 Feb. 24; 281 (8):4977-82; Biochem Soc Trans. 2007 February; 35 (Pt.1):101-4; Handb Exp Pharmacol. 2007; (179):109-23; J Biol Chem. 2005 Mar. 25; 280 (12):10997-1006; J Physiol. 2006 Jan. 15; 570 (Pt 2):219-35; and Nat Neurosci. (2003) 6: 837-45.

Modulating the function of TRPC5 proteins provides a means of modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

Compounds inhibiting TRPC5 containing ion channels are for example useful for treating conditions such as a neuropsychiatric disorder, a neurodegenerative disorder, nephropathy, and seizure disorder by modulating the activity of the transient receptor potential cation channel subfamily C, member 5 (TRPC5), which can exist in homomultimeric form as well as heteromultimeric form with other ion channels such as TRPC1 or TRPC3 (i.e. TRPC5-TRPC1 and TRPC 1-TRPC3-TRPC5). WO 2014/143799 discloses xanthine derivatives that inhibit TRPC5. They modulate the function of TRPC5 by inhibiting a TRPC5-mediated ion flux or by inhibiting the inward current, the outward current, or both currents mediated by TRPC5.

DETAILED DESCRIPTION OF THE INVENTION

The present invention provides novel substituted xanthine derivatives that unexpectedly are potent TRPC5-inhibitors. The compounds of the present invention differ from the structurally closest compounds disclosed in WO 2014/143799 in that the C8-position of the xanthine in the compounds of the present invention is substituted with a heteroaryl group rather than with a phenyl group.

In particular, the present invention provides the following compounds:

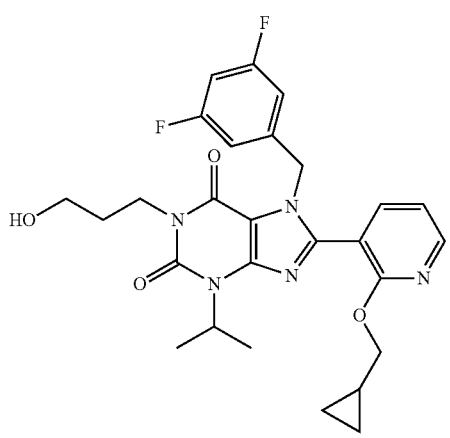

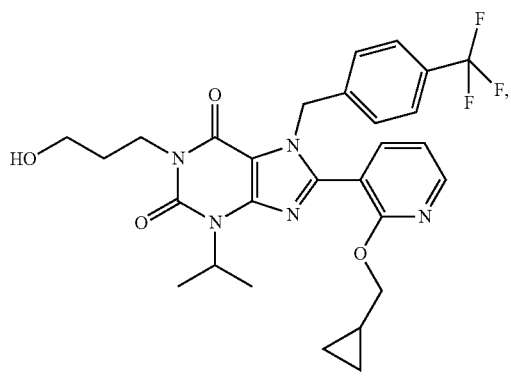
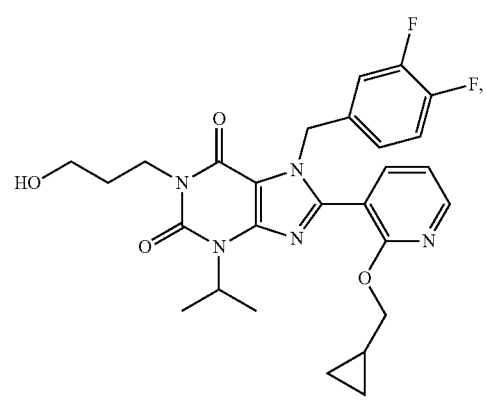
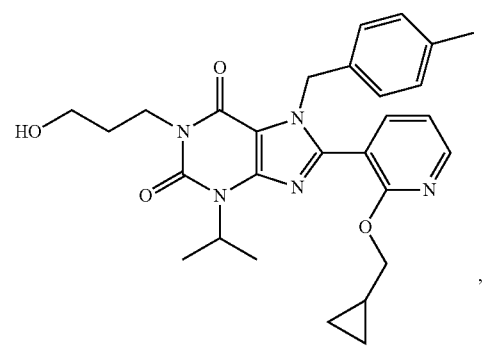
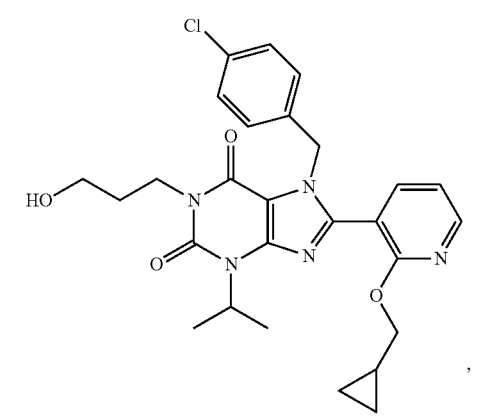
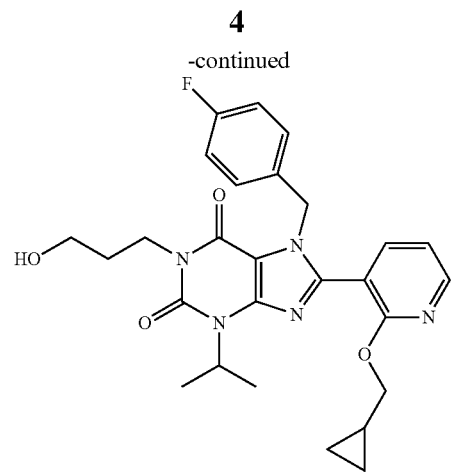
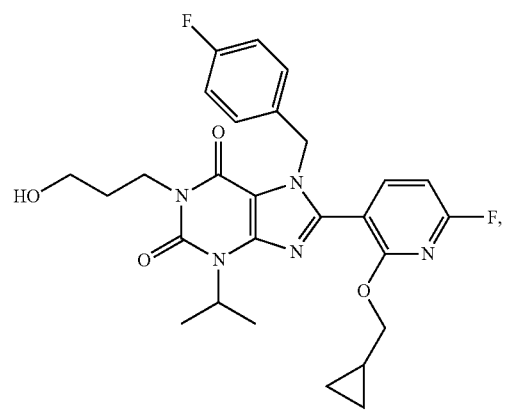
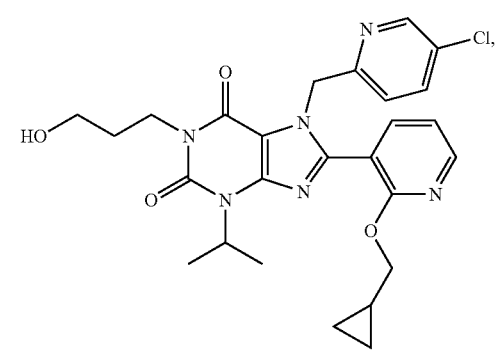
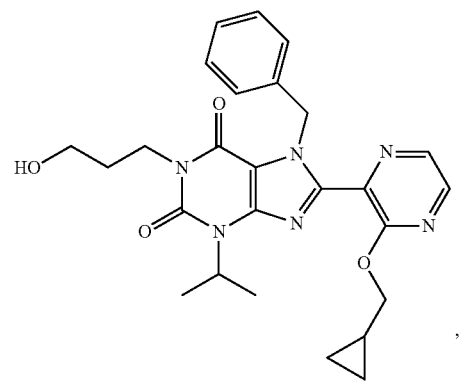

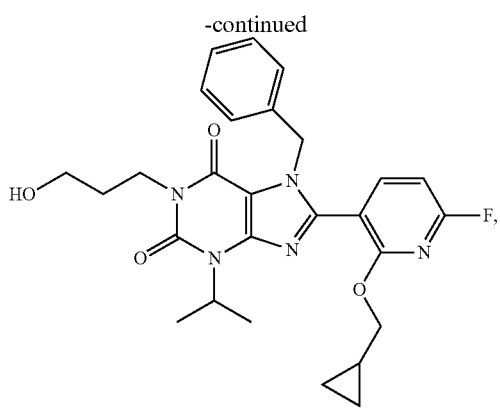
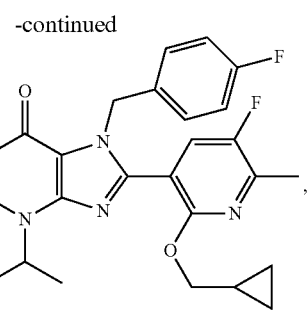
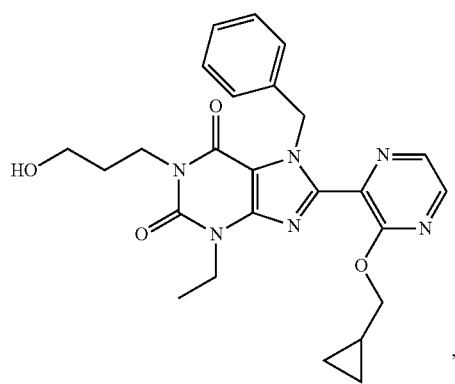
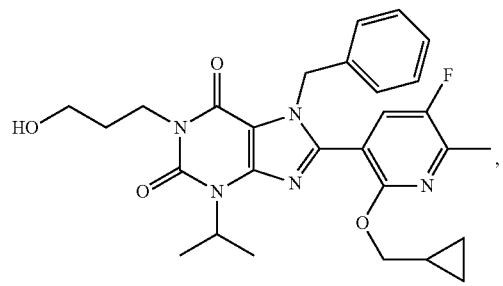
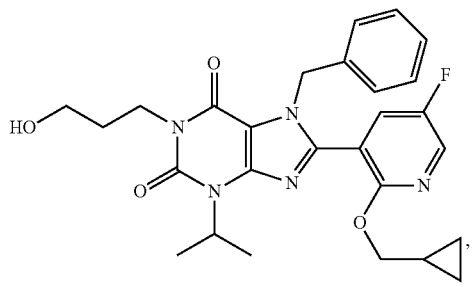
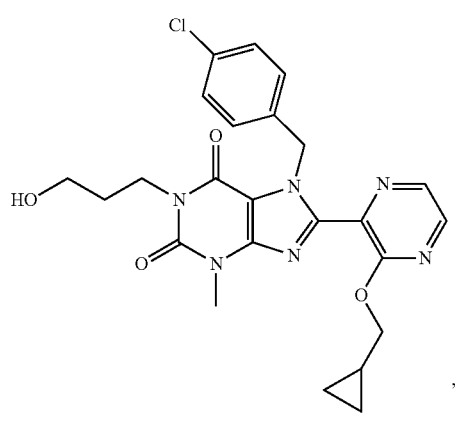
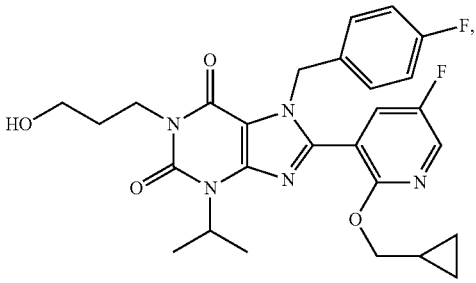
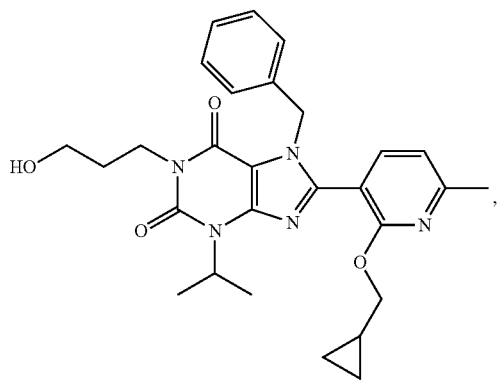
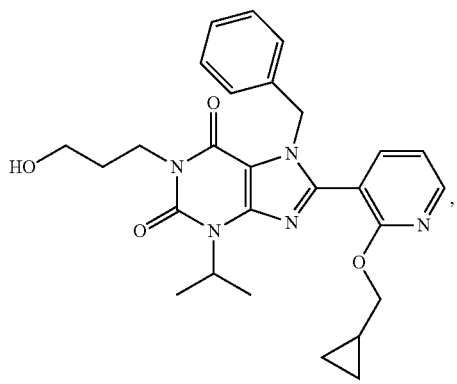

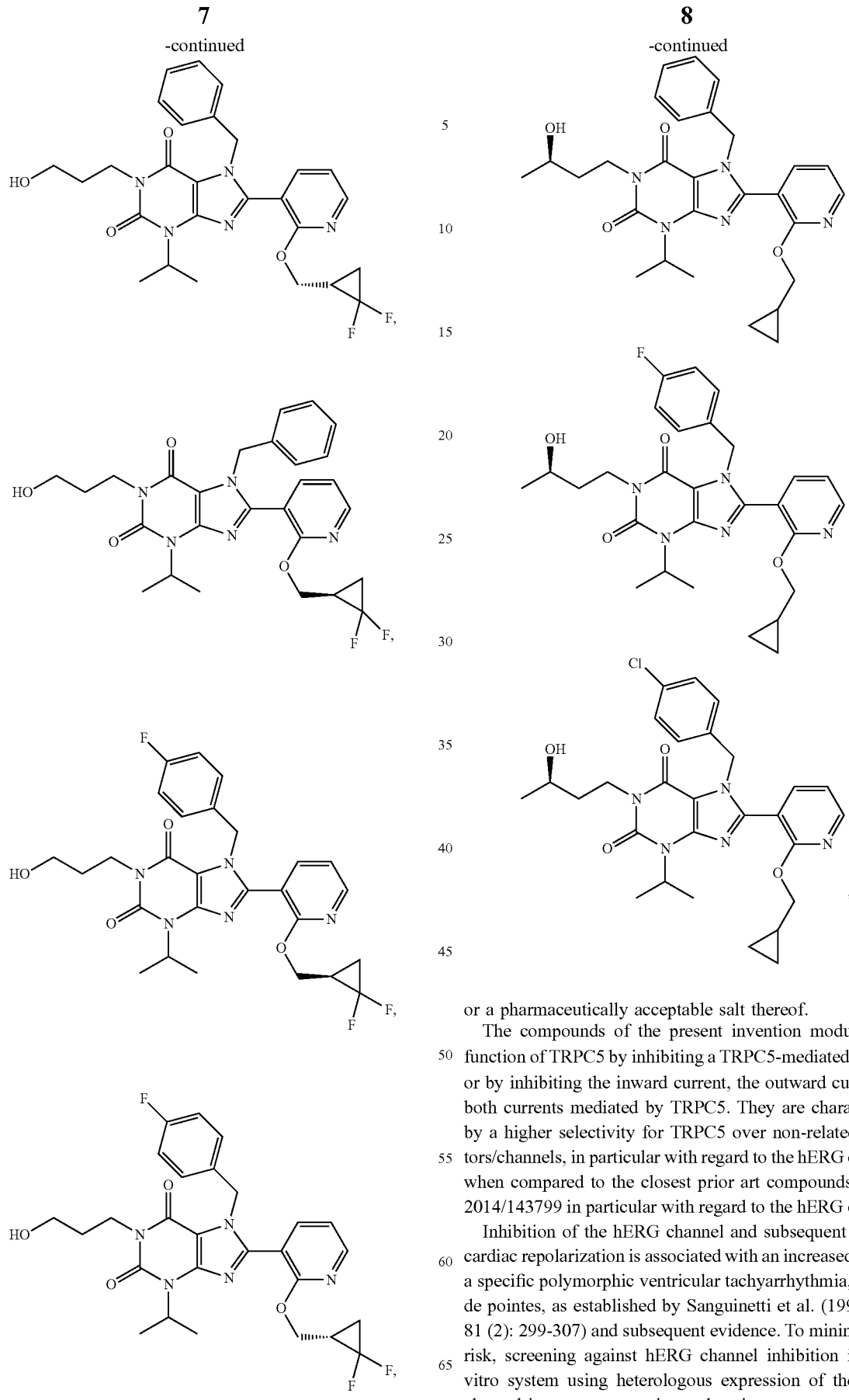

or a pharmaceutically acceptable salt thereof.

The compounds of the present invention modulate the function of TRPC5 by inhibiting a TRPC5-mediated ion flux or by inhibiting the inward current, the outward current, or both currents mediated by TRPC5. They are characterized by a higher selectivity for TRPC5 over non-related receptors/channels, in particular with regard to the hERG channel, when compared to the closest prior art compounds in WO 2014/143799 in particular with regard to the hERG channel.

Inhibition of the hERG channel and subsequent delayed cardiac repolarization is associated with an increased risk for a specific polymorphic ventricular tachyarrhythmia, torsade de pointes, as established by Sanguinetti et al. (1995, Cell, 81 (2): 299-307) and subsequent evidence. To minimize this risk, screening against hERG channel inhibition in an in vitro system using heterologous expression of the hERG channel is common practice and an important part of later preclinical profiling as recommended by the ICH guideline S 7 B (International Conference on Harmonization (2005): ICH Topic S 7 B; The nonclinical Evaluation of the Potential for delayed Ventricular Repolarization (QT Interval Prolongation) by Human Pharmaceuticals). Therefore, low hERG channel inhibition or interaction, such as shown by the compounds of the present invention, is highly desirable. Consequently, compounds of the present invention are more viable for human therapy.

The present invention thus provides compounds for use in the treatment of a TRPC5 mediated disorder.

The present invention further provides methods of treating a TRPC5 mediated disorder in a human subject comprising administering to the subject a compound or composition of a compound of the present invention or a pharmaceutically acceptable salt thereof.

In one aspect, the invention relates to a method for treating a condition for which reduced TRPC5 activity can reduce the severity of the condition, by administering a TRPC5 antagonist, such as a compound as described herein that inhibits a TRPC5-mediated current and/or a TRPC5-mediated ion flux. Described herein are compounds, which are TRPC5 antagonists that have a measured IC50 for inhibition of TRPC5 of 10 nanomolar or less. In certain embodiments, the compounds described herein, which are TRPC5 antagonists inhibit one or both of inward and outward TRPC5-mediated currents with an IC50 of 10 nanomolar or less. In certain embodiments, the compounds described herein inhibit at least 95% of a TRPC5-mediated current or a TRPC5-mediated ion flux when administered at 1 micromolar or less. At the same time, the compounds described herein do practically not interact with the hERG channel. Described herein are compounds, which are TRPC5 antagonists and have a measured IC50 for the inhibition of hERG of 1 micormolar or more, preferably of 5 micromolar or more and particularly preferred of 10 micromolar or more.

In another aspect, the compounds described herein, which are TRPC5 antagonists can be used to inhibit a function of TRPC5, for example a TRPC5-mediated current and/or a TRPC5-mediated ion flux. In some embodiments, the compounds described herein can be used to inhibit a TRPC5 mediated current in vitro, for example in cells in culture. In other embodiments, the compounds described herein can be used to inhibit a TRPC5 mediated current in vivo. In certain embodiments, the compounds described herein inhibit both an inward and an outward TRPC5-mediated current.

Definitions

Terms not specifically defined herein should be given the meanings that would be given to them by one skilled in the art in light of the disclosure and the context.

The terms "antagonist" and "inhibitor" are used interchangeably to refer to an agent that decreases or suppresses a biological activity, such as to repress an activity of an ion channel, such as TRPC5. TRPC5 ion channels as described herein include homomultimeric and heteromultimeric structures (e.g. homomultimeric TRPC5 and heteromeric TRPC5-TRPC1 or TRPC5-TRPC4). TRPC5 antagonists include inhibitors having any combination of the structural and/or functional properties disclosed herein.

An "effective amount" of, e.g. a TRPC5 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPC5 antagonist for use in the methods of the present invention includes an amount of a TRPC5 antagonist effective to decrease one or more in vitro or in vivo function of a TRPC5 channel. Exemplary functions include, but are not limited to, membrane polarization (e.g. an antagonist may promote hyperpolarization of a cell), ion flux, ion concentration in a cell, outward current, and inward current. Compounds that antagonize TRPC5 function include compounds that antagonize an in vitro or in vivo functional activity of TRPC5. When a particular functional activity is only readily observable in an in vitro assay, the ability of a compound to inhibit TRPC5 function in that in vitro assay serves as a reasonable proxy for the activity of that compound. In certain embodiments, an effective amount is an amount sufficient to inhibit a TRPC5-mediated current and/or an amount sufficient to inhibit TRPC5 mediated ion flux.

The TRPC5 antagonists for use in the methods of the present invention may be characterized according to their activity, or lack of activity, against one or more other ion channels. When other ion channels are referred to, inhibition of a function of such other ion channels is defined similarly. For example, inhibition of an ion channel or an activity of an ion channel means the antagonist inhibits one or more functional activities of the other ion channel. Such functions include the current mediated by the particular ion channel, ion flux, or membrane polarization.

The terms "compound" and "agent" are used interchangeably to refer to the inhibitors/antagonists of the invention.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as 3-camphorsulfonic acid. Other resolving agents suitable for fractional crystallization methods include stereoisomerically pure forms of α-methylbenzylamine (e.g., S- and R-forms, or diastereomerically pure forms), 2-phenylglycinol, norephedrine, ephedrine, N-methylephedrine, cyclohexylethylamine, and 1,2-diaminocyclohexane.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms, such as keto-enol tautomers.

Unless specifically indicated, throughout the specification and the appended claims, a given chemical formula or name shall encompass tautomers and all stereo, optical and geometrical isomers (e.g. enantiomers, diastereoisomers, E/Z isomers) and racemates thereof, as well as mixtures in different proportions of the separate enantiomers, mixtures of diastereoisomers, or mixtures of any of the foregoing forms where such isomers and enantiomers exist, as well as pharmaceutically acceptable salts thereof.

Compounds of the invention can also include all isotopes of atoms occurring in the intermediates or final compounds. For example, the compound of the invention may be radiolabeled with radioactive isotopes, such as for example tritium ($^3H$) or carbon-14 ($^{14}C$). All isotopic variations, whether radioactive or not, are intended to be encompassed within the scope of the present invention.

As used herein, "pharmaceutically acceptable salts" refer to derivatives of the disclosed compounds wherein the parent compound forms a salt with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid. Also included are the salts of amino acids such as arginate, and salts of organic acids like glucuronic or galactunoric acids (see, for example, Berge et al., "Pharmaceutical Salts", Journal of Pharmaceutical Science, 1977, 66, 1-19).

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane.

The neutral form of the compounds of the invention is preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The terms "TRPC5", "TRPC5 protein", and "TRPC5 channel" are used interchangeably throughout the application. Unless expressly stated, the term TRPC5 includes homomultimeric structures (e.g. homomultimeric TRPC5) and heteromultimeric structures (e.g. heteromultimeric TRPC5-TRPC1).

Biological Assays

The biological activity of compounds is determined by the following methods:

Assay A: Determination of TRPC5-Inhibition

Patch clamp experiments permit the detection of currents through the TRPC5 channel in a cell line. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution. A perfusion system permits control of the extracellular solution, including the addition of blockers and activators of the current. The current can be activated by including 1.4 μM free Ca2+ in the pipette (intracellular) solution, and 80 μM $LaCl_3$ in the extracellular solution.

TRPC5 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM HEDTA, 2 mM $CaCl_2$, 2.27 mM $MgCl_2$ and 10 mM HEPES, pH 7.2, with 1,400 nM calculated free Ca2+. The external solution consisted of 150 mM NaCl, 4.5 mM 15 KCl, 1 mM $MgCl_2$, 2 mM $CaCl_2$, 10 mM HEPES, 10 mM glucose, 1 mM EGTA, pH 7.4. Upon addition of $LaCl_3$, TRPC5 current was induced only in TRPC5-expressing cells and not in parental HEK293 TREx cells. Removal of the LaCh stimulus causes most of the current to go away. Potential blockers were tested for ability to block both inward and outward currents in the continued presence of $LaCl_3$.

IC50 of a compound of the invention was estimated by testing the compound 500 nM. When 500 nM of a compound showed no block, IC50 was estimated as >1 μM. Compounds blocking 50% or more at 500 nM are retested at multiple concentrations, and the % block is fitted by standard equations to determine IC50 accurately, using a ⅝ point concentration-response experiment.

Assay B: Determination of hERG-Inhibition hERG-channel inhibition was determined as described in Rast G, Guth B D, Solubility assessment and on-line exposure confirmation in a patch-clamp assay for hERG (human ether-a-go-go-related gene) potassium channel inhibition, J Pharmacol Toxicol Methods. 2014 September-October; 70(2):182-7.

Biological Data

TABLE 1

In vitro potencies of compounds of WO2014/143799 determined in the Assays A and B (described above)

| Compound | Structure | Assay A TRPC5 inhibition | Assay B hERG inhibition |
|---|---|---|---|
| Compound ID 260 in WO2014/143799 | [structure] | <10 nM | 1.9 µM |
| Compound ID 415 in WO2014/143799 | [structure] | Agonist | >10 µM |

While compound ID 260 in WO2014/143799 shows potent TRPC5-inhibition, it also shows hERG inhibition in the low µM range. Compound ID 415 in WO2014/143799, the structurally closest prior art compound, inhibits hERG at a higher concentration (>10 µM), however, it shows agonism (activation) at the TRPC5 channel, which is the complete opposite TRPC5 activity as compared to the presently claimed compounds, which are TRCP5 antagonists (inhibitiors).

The compounds of the present invention differ structurally from Example 415 in WO 2014/143799, i.e. the closest prior art compound, in that the C8-position of the xanthine in the presently claimed compounds is substituted with a heteroaryl group including 3-pyridyl and 2-pyrazinyl rather than with a phenyl group as in Example 415 of WO 2014/143799. Furthermore, the heteroaryl group in the presently claimed compounds is substituted with a cyclopropylmethyl-O- or difluorocyclopropylmethyl-O-group rather than with a methoxy-group, as in Example 415 of WO 2014/143799. These structural differences unexpectedly result in potent TRPC5-inhibition in combination with an improved selectivity profile with regard to hERG channel inhibition (Table 2).

These results demonstrate that, unexpectedly, compounds of the present invention are superior to the structurally most similar example disclosed in WO2014/143799 (closest prior art compound) with the combination of high potency inhibition of TRPC5 and reduced hERG channel inhibition. Consequently, compounds of the present invention are more viable for human use.

TABLE 2
In vitro potencies of compounds of the present invention determined in the Assays A and B (described above)
| Example | Structure | Assay A TRPC5 inhibition | Assay B hERG inhibition |
|---|---|---|---|
| 1 | 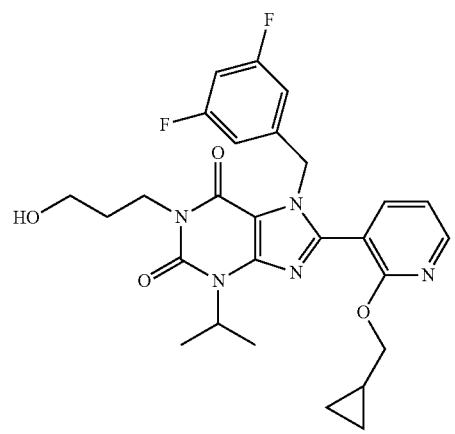 [SMILES: CC(C)n1c(=O)n(CCCO)c(=O)c2c1nc(-c1cccnc1OCC1CC1)n2Cc1cc(F)cc(F)c1] | <10 nM | >10 μM |
| 2 | 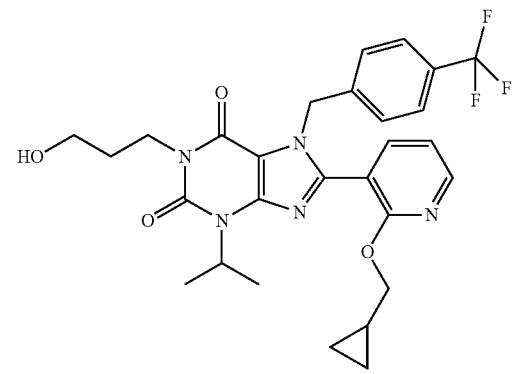 [SMILES: CC(C)n1c(=O)n(CCCO)c(=O)c2c1nc(-c1cccnc1OCC1CC1)n2Cc1ccc(C(F)(F)F)cc1] | <10 nM | 8.3 μM |
| 3 | 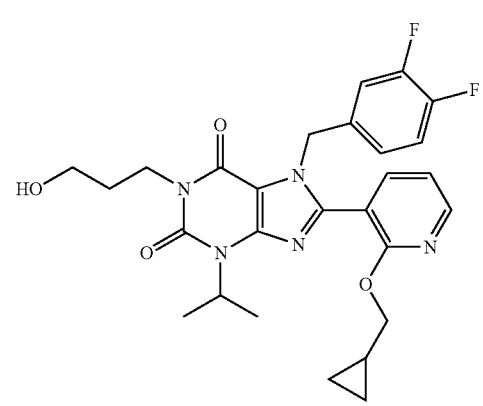 [SMILES: CC(C)n1c(=O)n(CCCO)c(=O)c2c1nc(-c1cccnc1OCC1CC1)n2Cc1ccc(F)c(F)c1] | <10 nM | >10 μM |

TABLE 2-continued
*In vitro potencies of compounds of the present invention determined in the Assays A and B (described above)*
| Example | Structure | Assay A TRPC5 inhibition | Assay B hERG inhibition |
|---|---|---|---|
| 4 | 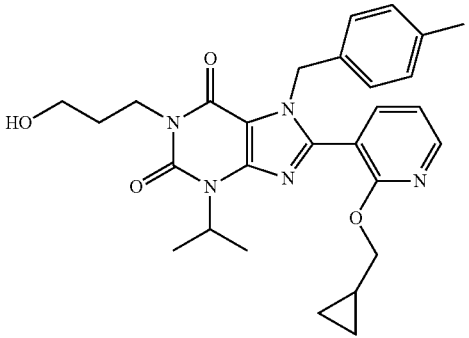 [SMILES: Cc1ccc(Cn2c(-c3cccnc3OCC3CC3)nc3c2c(=O)n(CCCO)c(=O)n3C(C)C)cc1] | <10 nM | >10 μM |
| 5 | 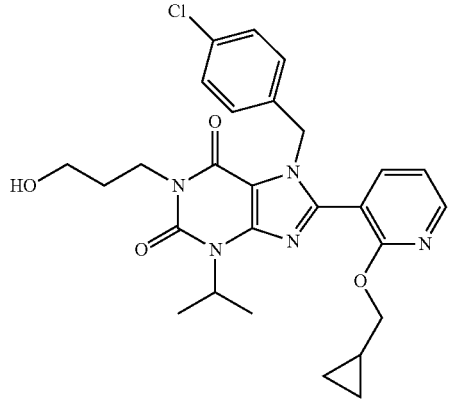 [SMILES: CC(C)n1c(=O)n(CCCO)c(=O)c2c1nc(-c1cccnc1OCC1CC1)n2Cc1ccc(Cl)cc1] | <10 nM | >10 μM |
| 6 | 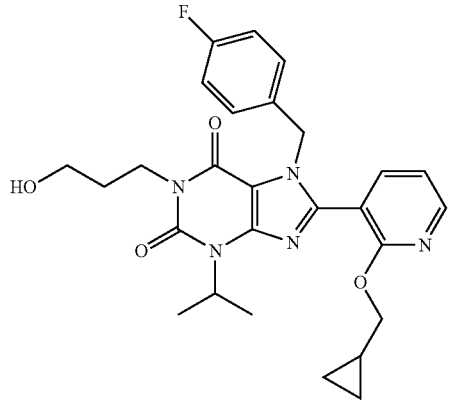 | <10 nM | >10 μM |

TABLE 2-continued

In vitro potencies of compounds of the present invention determined in the Assays A and B (described above)

| Example | Structure | Assay A TRPC5 inhibition | Assay B hERG inhibition |
|---|---|---|---|
| 7 | 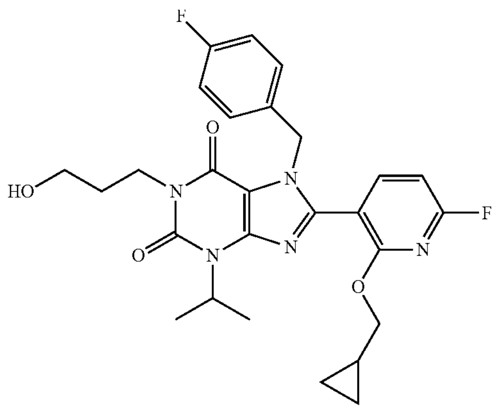 [SMILES: CC(C)n1c(=O)n(CCCO)c(=O)c2c1nc(-c1ccc(F)nc1OCC1CC1)n2Cc1ccc(F)cc1] | <10 nM | >10 μM |
| 8 | 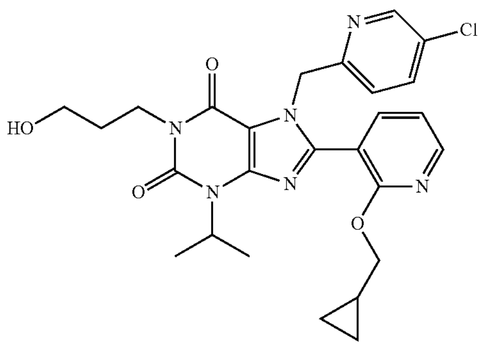 [SMILES: CC(C)n1c(=O)n(CCCO)c(=O)c2c1nc(-c1cccnc1OCC1CC1)n2Cc1ccc(Cl)cn1] | <10 nM | >10 μM |
| 9 | 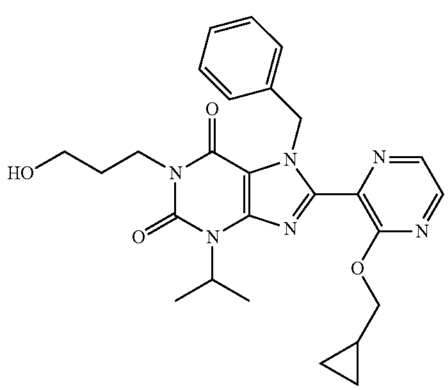 [SMILES: CC(C)n1c(=O)n(CCCO)c(=O)c2c1nc(-c1nccnc1OCC1CC1)n2Cc1ccccc1] | <10 nM | >10 μM |
| 10 | 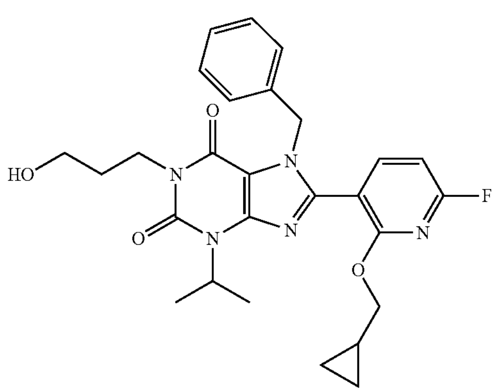 [SMILES: CC(C)n1c(=O)n(CCCO)c(=O)c2c1nc(-c1ccc(F)nc1OCC1CC1)n2Cc1ccccc1] | <10 nM | >10 μM |

TABLE 2-continued
In vitro potencies of compounds of the present invention determined in the Assays A and B (described above)
| Example | Structure | Assay A TRPC5 inhibition | Assay B hERG inhibition |
|---|---|---|---|
| 11 | 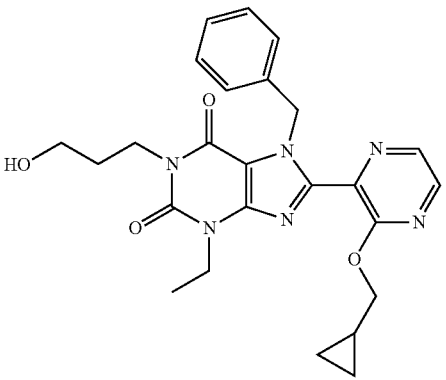 [SMILES: CCn1c(=O)n(CCCO)c(=O)c2c1nc(-c1nccnc1OCC1CC1)n2Cc1ccccc1] | <10 nM | >10 μM |
| 12 | 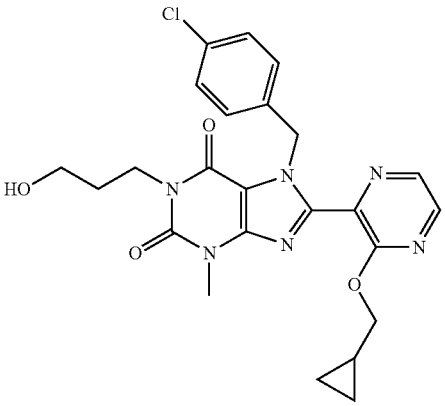 [SMILES: Cn1c(=O)n(CCCO)c(=O)c2c1nc(-c1nccnc1OCC1CC1)n2Cc1ccc(Cl)cc1] | <10 nM | >10 μM |
| 13 | 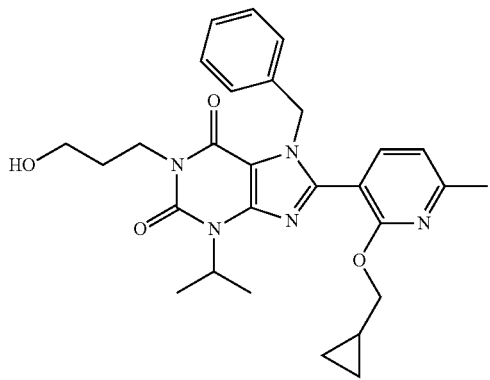 [SMILES: Cc1ccc(-c2nc3c(c(=O)n(CCCO)c(=O)n3C(C)C)n2Cc2ccccc2)c(OCC2CC2)n1] | <10 nM | >10 μM |
| 14 | 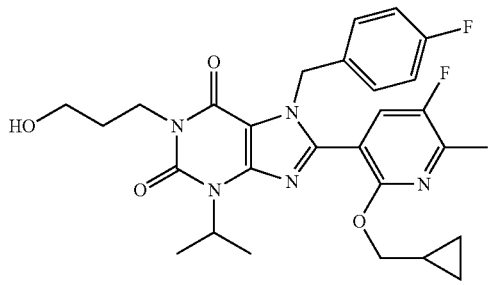 [SMILES: Cc1nc(OCC2CC2)c(-c2nc3c(c(=O)n(CCCO)c(=O)n3C(C)C)n2Cc2ccc(F)cc2)cc1F] | <10 nM | 5.8 μM |

TABLE 2-continued

In vitro potencies of compounds of the present invention determined in the Assays A and B (described above)

| Example | Structure | Assay A TRPC5 inhibition | Assay B hERG inhibition |
|---------|-----------|--------------------------|-------------------------|
| 15 | 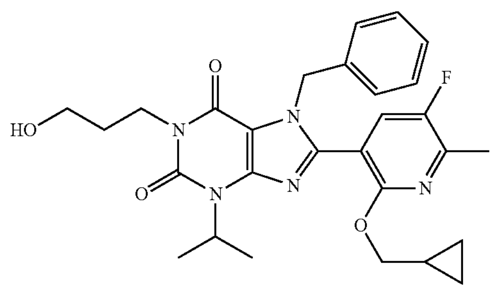 [SMILES: Cc1nc(OCC2CC2)c(-c2nc3c(c(=O)n(CCCO)c(=O)n3C(C)C)n2Cc2ccccc2)cc1F] | <10 nM | 5.8 μM |
| 16 | 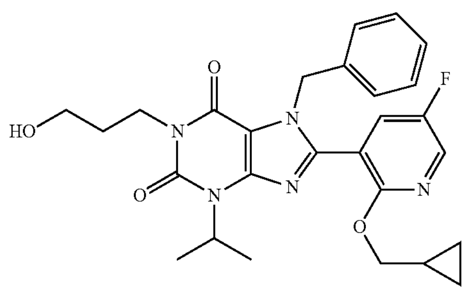 [SMILES: CC(C)n1c(=O)n(CCCO)c(=O)c2c1nc(-c1cc(F)cnc1OCC1CC1)n2Cc1ccccc1] | <10 nM | >10 μM |
| 17 | 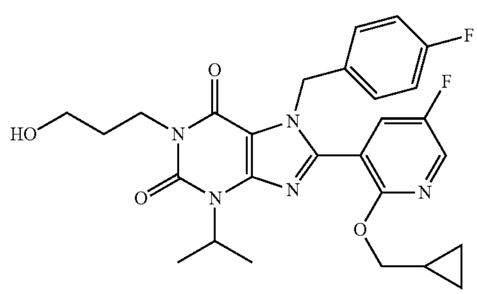 [SMILES: CC(C)n1c(=O)n(CCCO)c(=O)c2c1nc(-c1cc(F)cnc1OCC1CC1)n2Cc1ccc(F)cc1] | <10 nM | >10 μM |
| 18 | 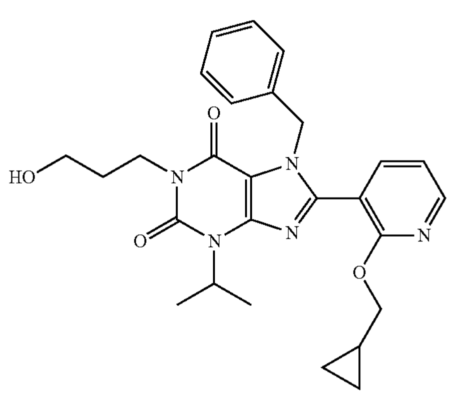 [SMILES: CC(C)n1c(=O)n(CCCO)c(=O)c2c1nc(-c1cccnc1OCC1CC1)n2Cc1ccccc1] | <10 nM | >10 μM |

TABLE 2-continued

In vitro potencies of compounds of the present invention determined in the Assays A and B (described above)

| Example | Structure | Assay A TRPC5 inhibition | Assay B hERG inhibition |
|---|---|---|---|
| 19 | 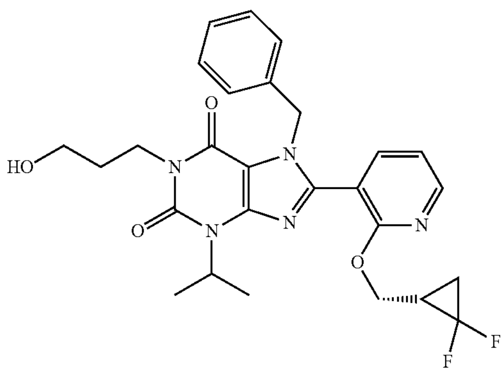 | <10 nM | >10 µM |
| 20 | 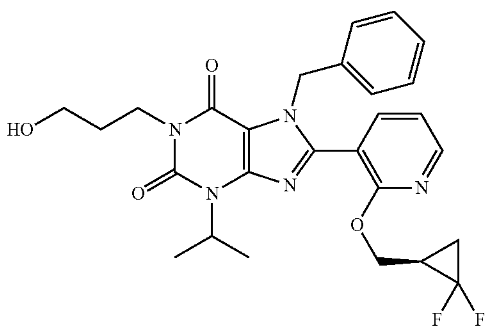 [SMILES: CC(C)n1c(=O)n(CCCO)c(=O)c2c1nc(-c1cccnc1OC[C@H]1CC1(F)F)n2Cc1ccccc1] | <10 nM | >10 µM |
| 21 | 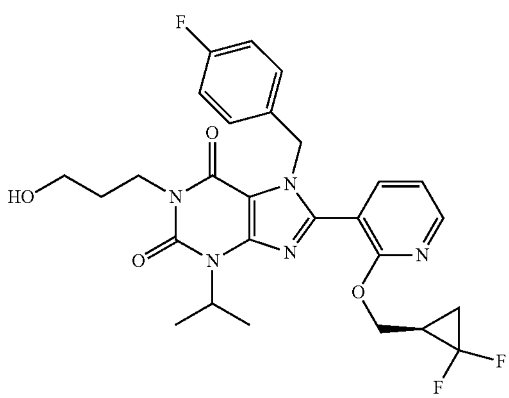 [SMILES: CC(C)n1c(=O)n(CCCO)c(=O)c2c1nc(-c1cccnc1OC[C@H]1CC1(F)F)n2Cc1ccc(F)cc1] | <10 nM | >10 µM |
| 22 | 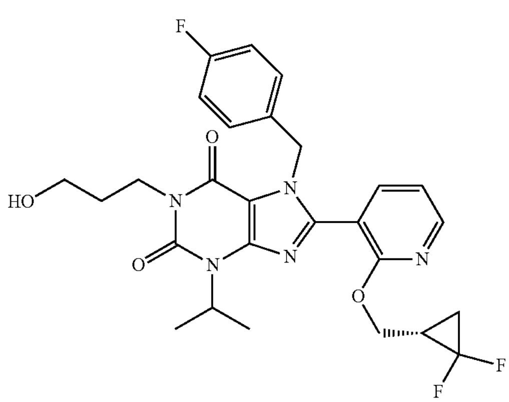 [SMILES: CC(C)n1c(=O)n(CCCO)c(=O)c2c1nc(-c1cccnc1OC[C@@H]1CC1(F)F)n2Cc1ccc(F)cc1] | <10 nM | >10 µM |

TABLE 2-continued

In vitro potencies of compounds of the present invention determined in the Assays A and B (described above)

| Example | Structure | Assay A TRPC5 inhibition | Assay B hERG inhibition |
|---|---|---|---|
| 23 | 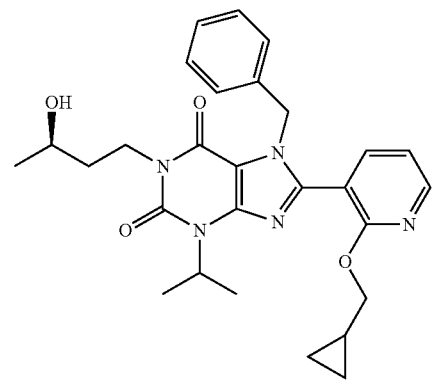 [SMILES: CC(C)n1c(=O)n(CC[C@@H](C)O)c(=O)c2c1nc(-c1cccnc1OCC1CC1)n2Cc1ccccc1] | <10 nM | >10 μM |
| 24 | 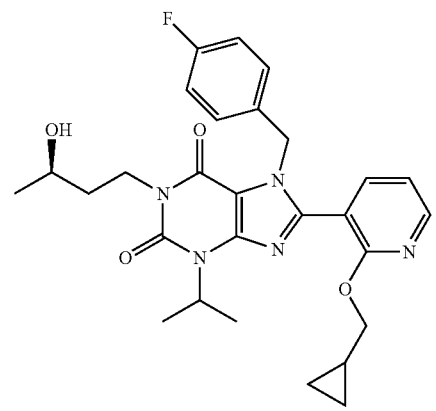 [SMILES: CC(C)n1c(=O)n(CC[C@@H](C)O)c(=O)c2c1nc(-c1cccnc1OCC1CC1)n2Cc1ccc(F)cc1] | <10 nM | >10 μM |
| 25 | 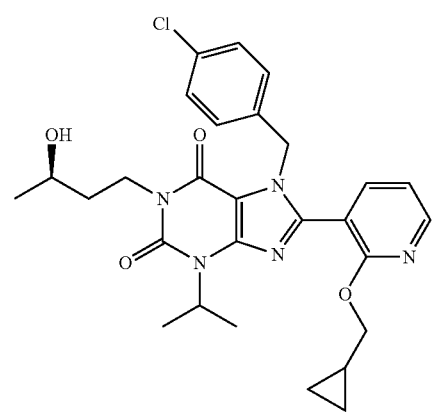 [SMILES: CC(C)n1c(=O)n(CC[C@@H](C)O)c(=O)c2c1nc(-c1cccnc1OCC1CC1)n2Cc1ccc(Cl)cc1] | <10 nM | 7.6 μM |

Use in Treatment/Method of Use

The present invention is directed to compounds which are useful in the treatment of a disease, disorder and condition wherein the inhibition of the activity of the transient receptor potential cation channel TRPC5 is of therapeutic benefit. This includes but is not limited to the treatment and/or prevention of psychiatric, neurological or neurodegenerative conditions, pain, seizure, non-neuronal conditions, and cancer.

Psychiatric conditions include diseases associated with dysregulated emotional processing (e.g. borderline personality disorder or depressive disorders like major depression, major depressive disorder, psychiatric depression, dysthymia, and postpartum depression, and bipolar disorders), anxiety and fear-related disorders (e.g. post-traumatic stress disorder, panic disorder, agoraphobia, social phobias, generalized anxiety disorder, panic disorder, social anxiety disorder, obsessive compulsive disorder, and separation anxiety), memory disorders (e.g. Alzheimer's disease, amnesia, aphasia, brain injury, brain tumor, chronic fatigue syndrome, Creutzfeldt-Jakob disease, dissociative amnesia, fugue amnesia, Huntington's disease, learning disorders, sleeping disorders, multiple personality disorder, pain, post-traumatic stress disorder, schizophrenia, sports injuries, stroke, and Wernicke-Korsakoff syndrome), disorders associated with impaired impulse control and addiction.

Neurological or neurodegenerative conditions include e.g. Alzheimer's disease (AD), Parkinson's disease, Huntington's disease, amyotrophic lateral sclerosis (ALS), and other brain disorders caused by trauma or other insults including aging.

Pain disorders include nociceptive pain, inflammatory pain, cancer pain, and neuropathic pain (e.g. cancer pain, osteoarthritic pain, rheumatoid arthritis pain, post-herpetic neuralgia, pain due to burns, and other indications). The pain can be chronic or acute.

Seizures may be induced by excitotoxicity of a variety of origins. Commonly excess neuronal firing can drive seizure activity. Compounds that reduce the hyperexcitability of relevant neuronal populations have significant potential in reducing seizure activity. Compounds of the invention that inhibit TRPC5 may reduce hyperexcitability and thus reduce seizure activity.

Non-neuronal conditions include nephropathy, proteinuric kidney disease, liver diseases (e.g. hepatic dyslipidemia associated with cholestasis), disorders associated with malfunction of the cardiovascular-vascular system or vascular permeability (e.g. pulmonary arterial hypertension, acute respiratory distress syndrome (ARDS), maladaptive cardiac remodeling), and disorders associated with maladaptive blood pressure control like hypertension or hypotension.

Another aspect of the invention relates to pharmaceutical compositions for use in a human patient, comprising an effective amount of a compound described herein (or a pharmaceutically acceptable salt thereof), and one or more pharmaceutically acceptable excipient(s). The invention further contemplates the use of the compounds described herein in the manufacture of a medicament or a pharmaceutical composition to treat or reduce the symptoms of any of the diseases or conditions provided in the specification. The compounds described herein can be used for treating a particular disease or condition and can be formulated for administration via a route appropriate for the particular disease or condition.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable compositions for administering the compounds of the present invention will be apparent to those with ordinary skill in the art and include for example tablets, pills, capsules, suppositories, lozenges, troches, solutions, syrups, elixirs, sachets, injectables, inhalatives, and powders. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and compressing the resulting mixture to tablets.

Combination Therapy

The compounds of the present invention can be used alone or in combination with other active pharmaceutical ingredients. In particular, compounds according to the present invention can be combined with other treatment options known to be used in the art in connection with a treatment of any of the indications the treatment of which is in the focus of the present invention.

Among such active pharmaceutical ingredients or treatment options that are considered suitable for combination with the compounds and the treatment according to the present invention are antidepressants, mood stabilizers, typical and atypical antipsychotics, anxiolytics, antiepileptic drugs, sleeping agents, cognitive enhancers, stimulants, additional psychoactive drugs, anti-inflammatory drugs, analgesic drugs, and chemotherapeutic drugs.

EXPERIMENTAL SECTION

List of Abbreviations

ACN Acetonitrile
aq aqueous
conc concentrated
d day
DCM Dichloromethane
DIPEA N-Ethyl-diisopropylamine
DMF N,N-Dimethylformamide
DMSO Dimethylsulfoxide
equiv Equivalent
h Hour(s)
HPLC High performance liquid chromatography
HOAc acetic acid
MeOH Methanol
min Minute(s)
mL Milliliter
N Normal
PE Petroleum ether
rt Room temperature (20 to 25° C.)
tBME Tert-butylmethylether
TEA Triethylamine
TFA Trifluoroacetic acid
THF Tetrahydrofuran
RT Retention time (min)
μl Microliter
HPLC-Methods:
Method Name: A
Column: Sunfire C18, 2.1×30 mm, 2.5 μm
Column Supplier: Waters

| Gradient/Solvent Time [min] | % Sol [H$_2$O, 0.1% TFA] | % Sol [ACN] | Flow [mL/min] | Temp [° C.] |
|---|---|---|---|---|
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method Name: B
Column: XBridge BEH Phenyl, 2.1×30 mm, 1.7 μm
Column Supplier: Waters

| Gradient/Solvent Time [min] | % Sol [H₂O, 0.1% NH₃] | % Sol [Acetonitril] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: C
Column: XBridge C18, 4.6×30 mm, 3.5 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.00 | 97 | 3 | 5 | 60 |
| 0.02 | 97 | 3 | 5 | 60 |
| 1.60 | 0 | 100 | 5 | 60 |
| 1.70 | 0 | 100 | 5 | 60 |

Method Name: D
Column: XBridge BEH C18, 2.1×30 mm, 1.7 μm
Column Supplier: Waters

| Gradient/Solvent Time [min] | % Sol [H₂O, 0.1% NH₃] | % Sol [ACN] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

Method Name: E
Column: Chiralpak® AD-H, 4.6×250 mm, 5 μm
Column Supplier: Agilent

| Gradient/Solvent Time [min] | % Sol [scCO₂] | % Sol [IPA 20 mM NH₃] | Flow [mL/min] | Temp [° C.] | Back pressure (PSI) |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Method Name: F
Column: Sunfire C18, 3.0×30 mm, 2.5 μm
Column Supplier: Waters

| Gradient/Solvent Time [min] | % Sol [H₂O, 0.1% TFA (v/v)] | % Sol [ACN] | Flow [mL/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |

Method Name: G
Column: XBridge BEH C18, 2.1×30 mm, 2.5 μm
Column Supplier: Waters NMR Method:
NMR spectra were recorded on a Bruker AVANCE IIIHD 400 MHz instrument using TopSpin 3.2 p16 software. Chemical shifts are given in parts per million (ppm) downfield from internal reference trimethylsilane in δ units. Selected data are reported in the following manner: chemical shift (multiplicity, coupling constants (J), number of hydrogens). Abbreviations are as follows: s (singulet), d (doublet), t (triplet), q (quartet), spt (septet), m (multiplet), br (broad).

INTERMEDIATES

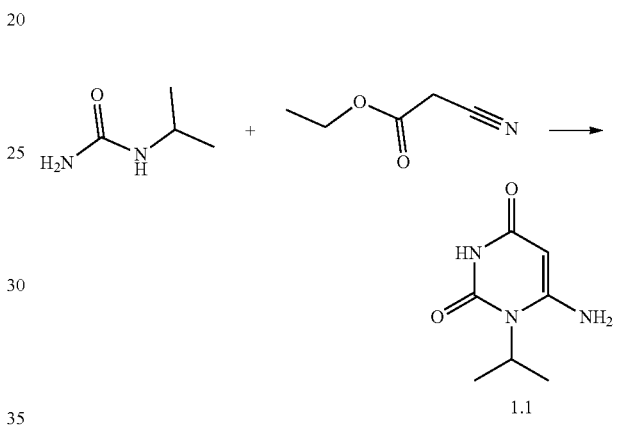

Intermediate 1.1

The reaction was performed under argon atmosphere and in dried glassware. Na (4.50 g, 196 mmol) was added in pieces to dry propan-2-ol (150 mL). The mixture was stirred for 2 h and heated to 95° C. After the Na was completely dissolved, isopropyl-urea (10.0 g, 97.9 mmol) and cyanoacetic acid ethyl ester (10.4 mL, 97.9 mmol) were added and the mixture was stirred overnight at 95° C. The mixture was cooled down and H₂O (40.0 mL) was added and the pH was adjusted to 6 with conc HCl. Stirring was continued under ice cooling and N₂ atmosphere for 12 h. The obtained precipitate was filtered and dried to obtain the product.
MS (ESI⁺): (M+H)⁺ 170
HPLC: RT=0.23 min, Method F Intermediate 2.1

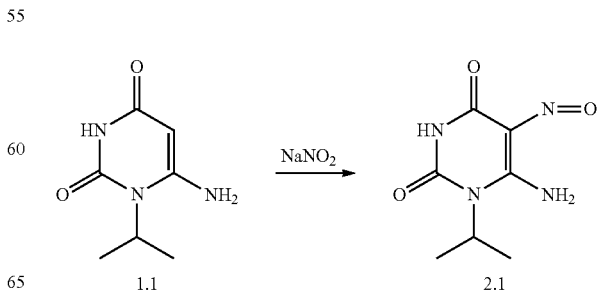

To a mixture of intermediate 1.1 (1.00 g, 5.91 mmol) in HCl (1 mol/l, 16.5 mL, 16.5 mmol) NaNO₂ (571 mg, 8.28 mmol) in H₂O (6.00 mL) was added dropwise. NaOH (4 N, about 4 mL) was added until the pH of the solution reached pH=9. The obtained precipitate was filtered, washed with MeOH and tBMe and dried to obtain the product.

MS (ESI⁺): (M+H)⁺ 199

HPLC: RT=0.24 min, Method F

Intermediate 2.2

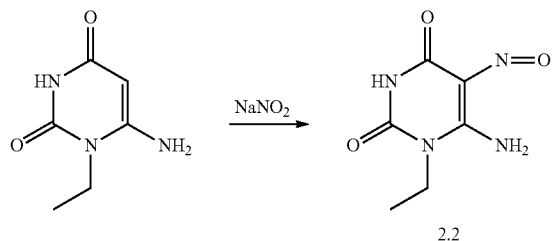

2.2

To a mixture of 6-amino-1-ethyl-1H-pyrimidine-2,4-dione (41.4 g, 0.267 mol) in HOAc (510 mL, 8.74 mol) NaNO₂ (25.7 g, 0.373 mol) in H₂O (185 mL) was added dropwise. The mixture was stirred for 1.5 h at rt and 400 mL of a NH₃ solution (25%) was added under ice cooling. The resulting precipitate was filtered and washed with MeOH and tBME to obtain the product.

MS (ESI⁺): (M+H)⁺ 185

HPLC: RT=0.10 min, Method B

Intermediate 3.1

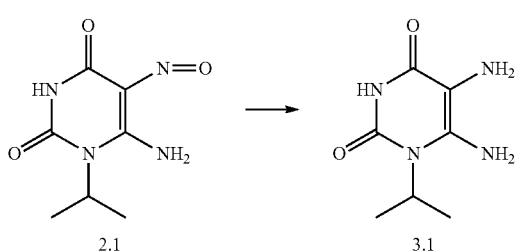

2.1                    3.1

A mixture of intermediate 2.1 (142 g, 666 mmol), Pd/C (10%, 14.0 g) and NaOH (1 mol/L, 1.00 L, 1.00 mol) was hydrogenated at rt and 50 psi of H₂ for 3 h. The mixture was filtered off and the pH was adjusted to 7 with conc HCl solution (82.0 mL, 864 mmol). After 30 min stirring the mixture was filtered, washed with H₂O and dried to obtain the product.

MS (ESI⁺): (M+H)⁺ 185

HPLC: RT=0.14 min, Method G

Intermediate 3.2

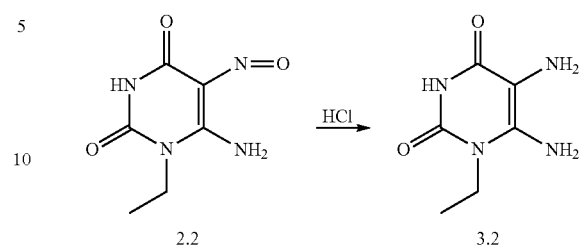

2.2                    3.2

A mixture of intermediate 2.2 (12.0 g, 42.4 mmol), Pd/C (10%, 1.50 g) and HCl solution (1 mol/L, 72.0 mL, 72.0 mmol) was hydrogenated at rt and 50 psi of H₂ for 1 d. The mixture was filtered, washed with HCl solution (1 mol/L), concentrated and freezedried to obtain the product.

MS (ESI⁺): (M+H)⁺ 171

HPLC: RT=0.13 min, Method D

Intermediate 3.3

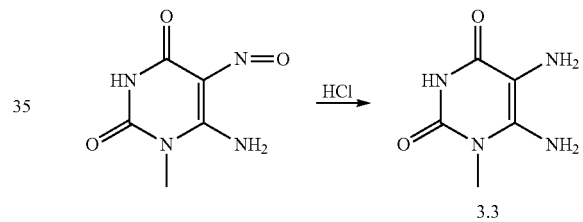

3.3

A mixture of 6-Amino-1-methyl-5-nitrosouracil (2.00 g, 11.8 mmol), Pd/C (10%, 600 mg), MeOH (24.0 mL), H₂O (16.0 mL) and HCl solution (1 mol/L, 12.9 mL, 12.9 mmol) was hydrogenated at rt and 50 psi of H₂ for 3.5 h. The mixture was filtered and concentrated in vacuo to give the product.

MS (ESI⁺): (M+H)⁺ 157

HPLC: RT=0.07 min, Method C

Intermediate 4.1

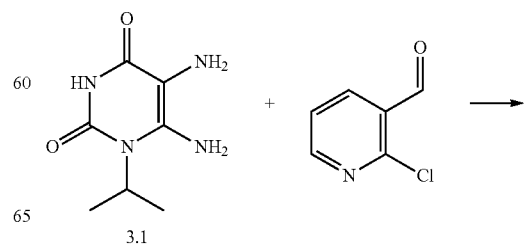

3.1

-continued

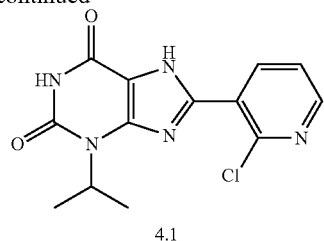

4.1

To a mixture of intermediate 3.1 (1.00 g, 5.43 mmol) in DMF (3.00 mL) and DMSO (3.00 mL) was added HCl solution in dioxan (4 mol/L, 1.36 mL, 5.43 mmol). Then 2-chloro-pyridine-3-carbaldehyde (0.769 g, 5.43 mmol) was added and the mixture was stirred 2.5 h at 70° C. The mixture was cooled to rt, MeOH was added and the obtained precipitate was filtered and dried to obtain the product.

MS (ESI$^+$): (M+H)$^+$ 306

HPLC: RT=0.58 min, Method F

Intermediate 4.2

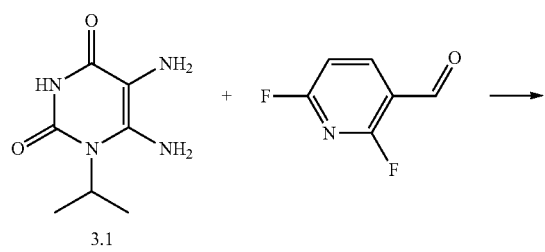

3.1

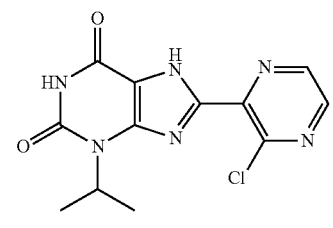

4.2

To a mixture of intermediate 3.1 (500 mg, 2.71 mmol) and 2,6-difluoro-pyridine-3-carbaldehyde (388 mg, 2.71 mmol) in DMF (1.00 mL) and DMSO (1.00 mL) was added dropwise HCl solution in dioxane (136 µl, 0.543 mmol). The mixture was stirred for 45 min at 100° C., then H$_2$O was added, stirred for 30 min at rt, the precipitate was filtered, washed with H$_2$O and dried to obtain the product.

MS (ESI$^+$): (M+H)$^+$ 308

HPLC: RT=0.68 min, Method F

Intermediate 4.3

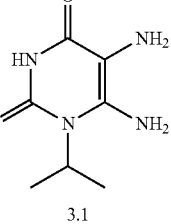 + 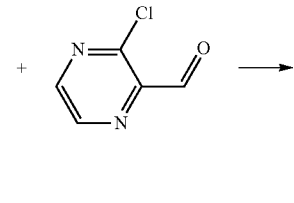 →

3.1

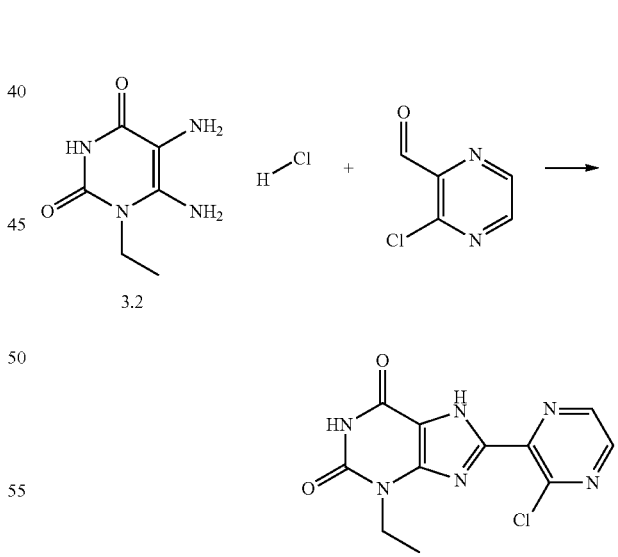

4.3

Intermediate 4.3 was prepared in an analogous manner to intermediate 4.1 using intermediate 3.1 and 3-chloro-pyrazine-2-carbaldehyde.

MS (ESI$^+$): (M+H)$^+$ 307

HPLC: RT=0.73 min, Method F

Intermediate 4.4

Intermediate 4.4 was prepared in an analogous manner to intermediate 4.1 using intermediate 3.2 and 3-chloro-pyrazine-2-carbaldehyde.

MS (ESI$^+$): (M+H)$^+$ 294

HPLC: RT=0.49 min, Method F

Intermediate 4.5

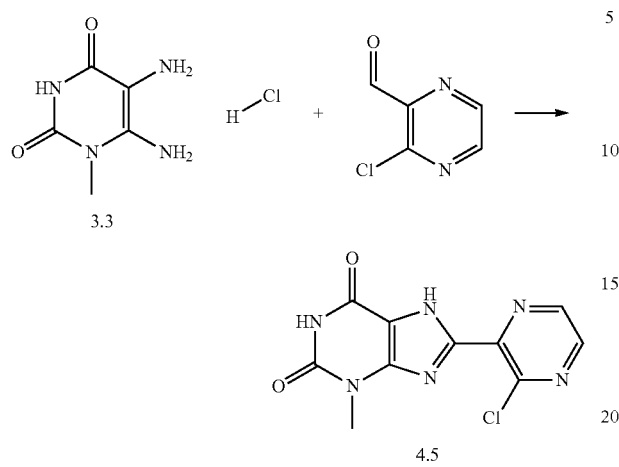

3.3

4.5

A mixture of intermediate 3.3 (2.00 g, 10.4 mmol) and 3-chloro-pyrazine-2-carbaldehyde (1.48 g, 10.4 mmol) in DMF (10.0 mL) and DMSO (5.00 mL) was stirred for 45 min at 100° C. in a microwave. 1,1,1-Triacetoxy-1,1-di-hydro-1,2-benziodoxol-3(1H)-one (4.40 g, 10.4 mmol) was added and the mixture was stirred for 1 h at rt. The mixture was poured into $H_2O$, filtered, washed with $H_2O$ and dried to obtain the product.

MS (ESI$^+$): (M+H)$^+$ 279

HPLC: RT=0.41 min, Method F

Intermediate 4.6

3.1

4.6

Intermediate 4.6 was prepared in an analogous manner to intermediate 4.1 using intermediate 3.1 and 2-chloro-6-methyl-pyridine-3-carbaldehyde.

MS (ESI$^+$): (M+H)$^+$ 320

HPLC: RT=0.64 min, Method F

Intermediate 4.7

4.7

To a mixture of intermediate 3.1 (3.00 g, 16.3 mmol) in diethoxymethoxy-ethane (25.4 mL, 153 mmol) formic acid (823 µl, 18.8 mmol) was added and the mixture was stirred at 150° C. overnight. The mixture was cooled down to rt, filtered and the precipitate was washed with tBME and dried (2.82 g, 89%) to give the product.

MS (ESI$^+$): (M+H)$^+$ 195

HPLC: RT=0.36 min, Method F

Intermediate 5.1

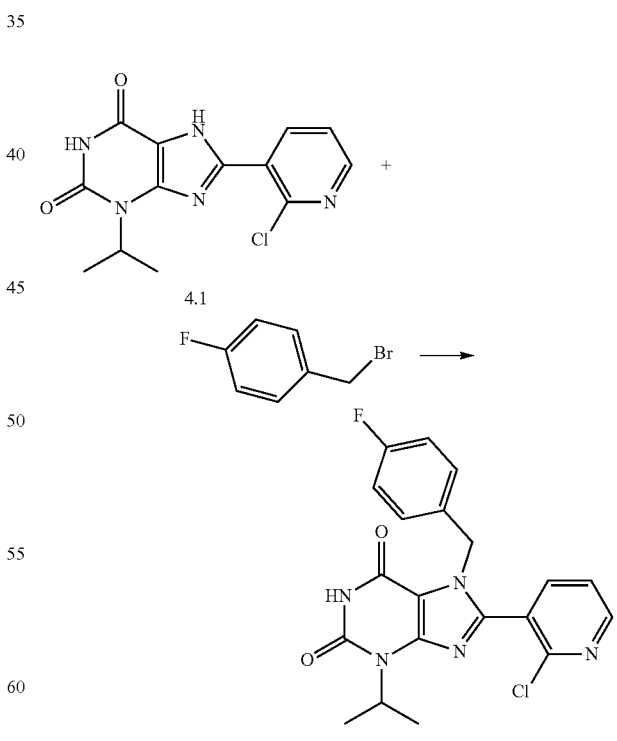

4.1

5.1

To a mixture of intermediate 4.1 (250 mg, 0.818 mmol) in DMF (7.00 mL) DIPEA (0.169 mL, 0.981 mmol) was added and the mixture was stirred 15 min at 55° C. 1-bromomethyl-4-fluoro-benzene (0.102 mL, 0.818 mmol) was added and the mixture was stirred at 55° C. overnight. H₂O was added and the resulting mixture extracted twice with EtOAc. The combined organic layers were washed with saturated NaCl solution, dried, concentrated and purified by chromatography to obtain the product.

MS (ESI⁺): (M+H)⁺ 415

HPLC: RT=0.79 min, Method F

Intermediate 5.2

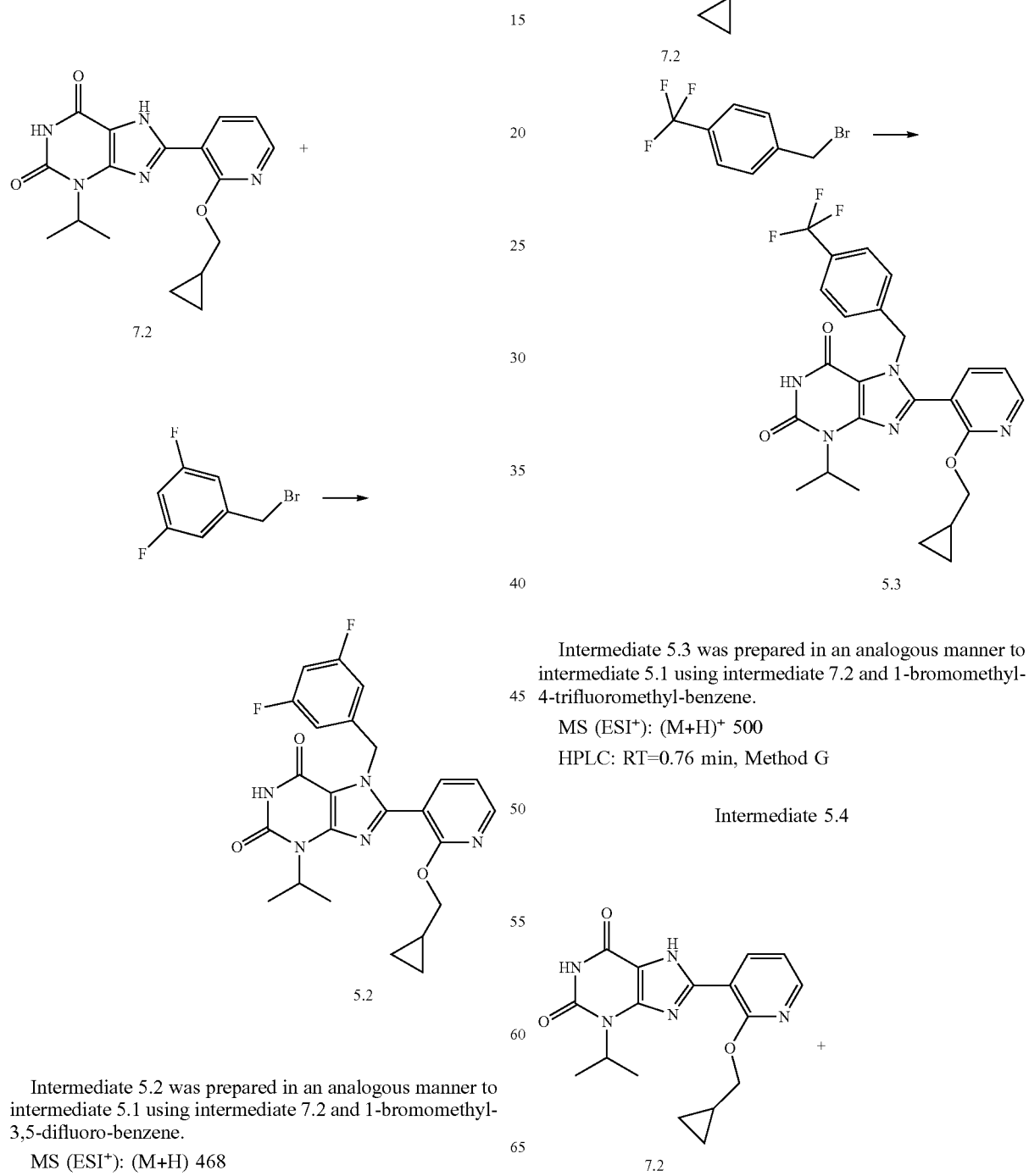

Intermediate 5.2 was prepared in an analogous manner to intermediate 5.1 using intermediate 7.2 and 1-bromomethyl-3,5-difluoro-benzene.

MS (ESI⁺): (M+H) 468

HPLC: RT=0.72 min, Method G

Intermediate 5.3 was prepared in an analogous manner to intermediate 5.1 using intermediate 7.2 and 1-bromomethyl-4-trifluoromethyl-benzene.

MS (ESI⁺): (M+H)⁺ 500

HPLC: RT=0.76 min, Method G

Intermediate 5.4

-continued

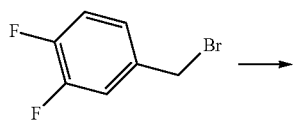

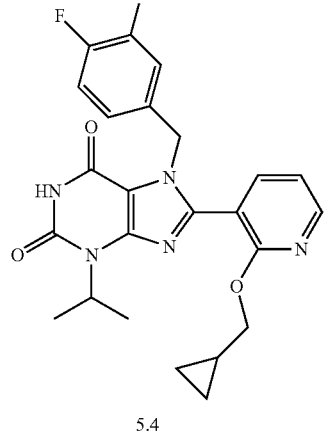

5.4

Intermediate 5.4 was prepared in an analogous manner to intermediate 5.1 using intermediate 7.2 and 4-bromomethyl-1,2-difluoro-benzene.
MS (ESI⁺): (M+H)⁺ 468
HPLC: RT=0.72 min, Method G Intermediate 5.5

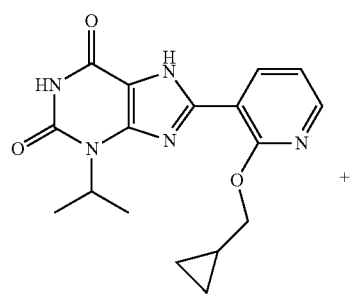

7.2

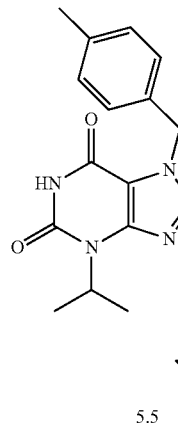

5.5

Intermediate 5.5 was prepared in an analogous manner to intermediate 5.1 using intermediate 7.2 and 1-bromomethyl-4-methyl-benzene.
MS (ESI⁺): (M+H)⁺ 466
HPLC: RT=0.74 min, Method G Intermediate 5.6

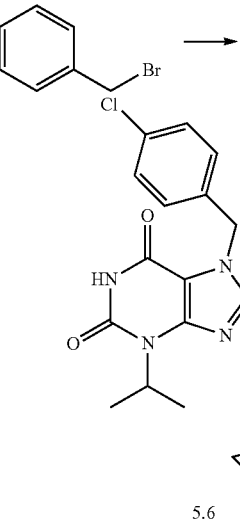

5.6

Intermediate 5.6 was prepared in an analogous manner to intermediate 5.1 using intermediate 7.2 and 1-bromomethyl-4-chloro-benzene.
MS (ESI⁺): (M+H)⁺ 467
HPLC: RT=0.74 min, Method G Intermediate 5.7

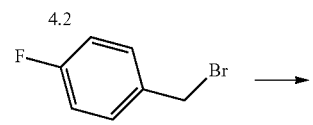

4.2

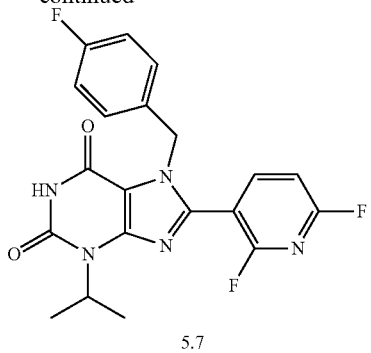

5.7

Intermediate 5.7 was prepared in an analogous manner to intermediate 5.1 using intermediate 4.2 and 1-bromomethyl-4-fluoro-benzene.
MS (ESI⁺): (M+H)⁺ 416
HPLC: RT=0.87 min, Method F Intermediate 5.8

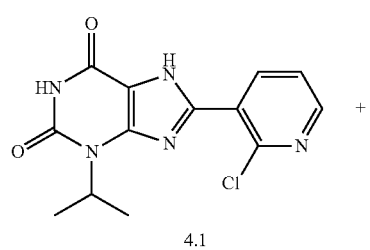

4.1

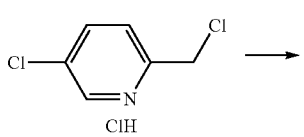

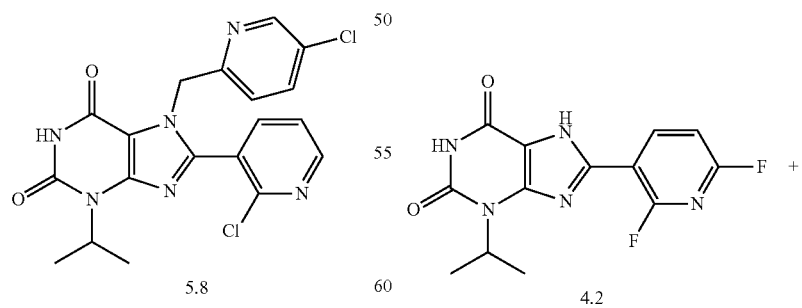

5.8

Intermediate 5.8 was prepared in an analogous manner to intermediate 5.1 using intermediate 4.1 and 5-chloro-2-chloromethyl-pyridine hydrochloride.
MS (ESI⁺): (M+H)⁺ 431
HPLC: RT=0.75 min, Method F Intermediate 5.9

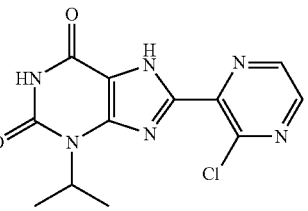

4.3

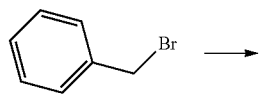

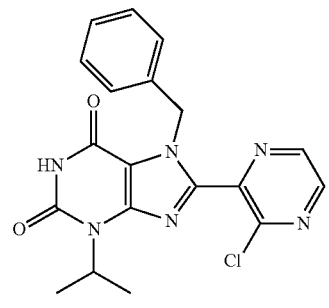

5.9

Intermediate 5.9 was prepared in an analogous manner to intermediate 5.1 using intermediate 4.3 and bromomethyl-benzene.
MS (ESI⁺): (M+H)⁺ 397
HPLC: RT=0.81 min, Method F Intermediate 5.10

4.2

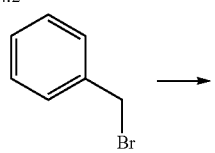

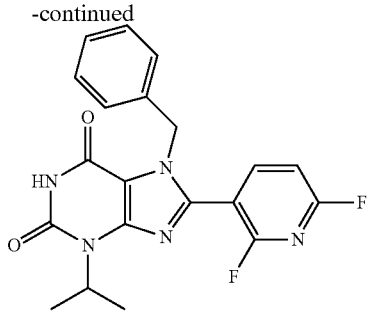

5.10

Intermediate 5.10 was prepared in an analogous manner to intermediate 5.1 using intermediate 4.2 and bromomethyl-benzene.
MS (ESI⁺): (M+H)⁺ 398
HPLC: RT=0.86 min, Method F Intermediate 5.12

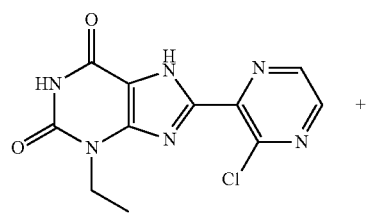

4.4

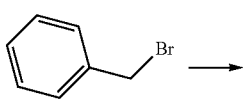

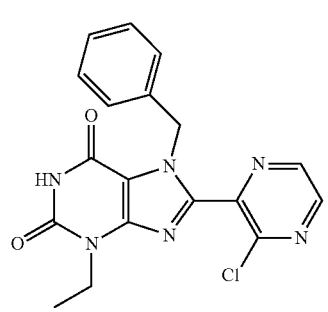

5.12

Intermediate 5.12 was prepared in an analogous manner to intermediate 5.1 using intermediate 4.4 and bromomethyl-benzene.
MS (ESI⁺): (M+H)⁺ 383
HPLC: RT=0.7 min, Method F Intermediate 5.13

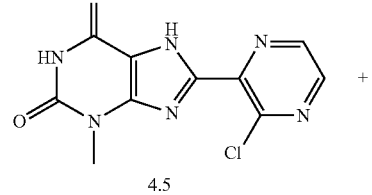

4.5

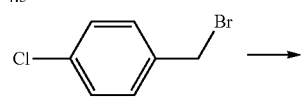

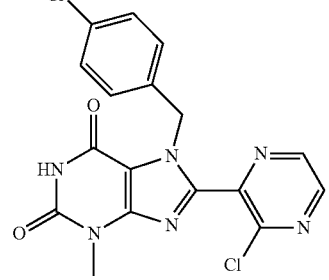

5.13

Intermediate 5.13 was prepared in an analogous manner to intermediate 5.1 using intermediate 4.5 and 1-bromomethyl-4-chloro-benzene.
MS (ESI⁺): (M+H)⁺ 403
HPLC: RT=0.74 min, Method F Intermediate 5.14

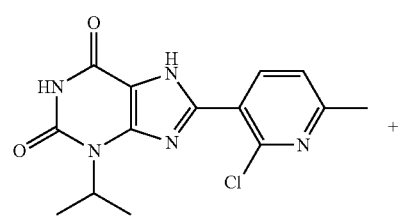

4.6

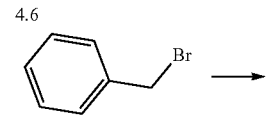

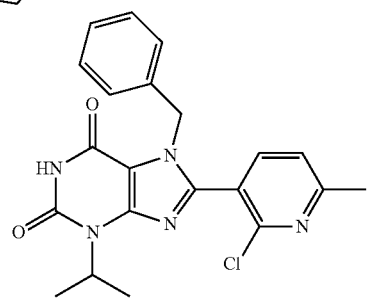

5.14

Intermediate 5.14 was prepared in an analogous manner to intermediate 5.1 using intermediate 4.6 and bromomethyl-benzene.
MS (ESI⁺): (M+H)⁺ 410
HPLC: RT=0.84 min, Method F Intermediate 5.15

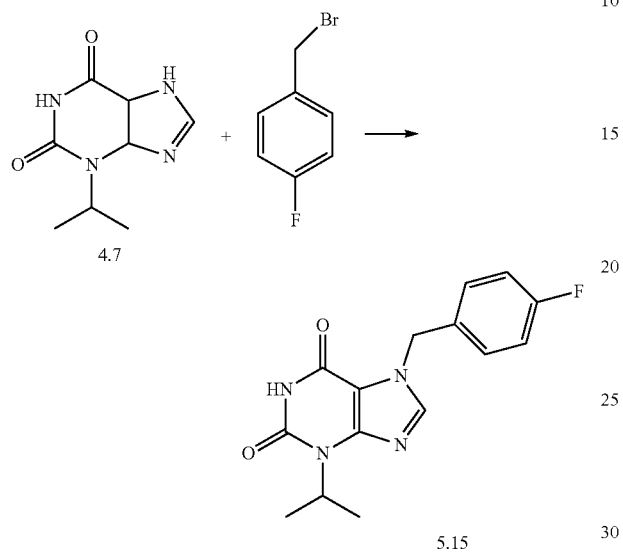

Intermediate 5.15 was prepared in an analogous manner to intermediate 5.1 using intermediate 4.7 and 1-bromomethyl-4-fluoro-benzene.
MS (ESI⁺): (M+H)⁺ 303
HPLC: RT=0.48 min, Method G Intermediate 5.16

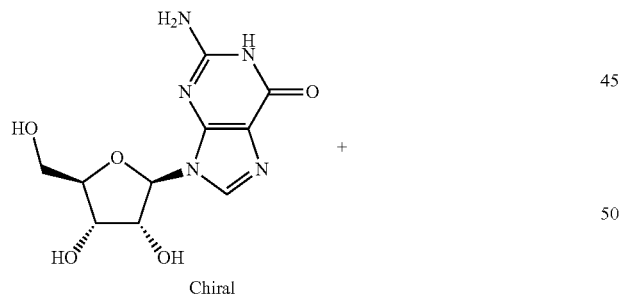

To a mixture of 2-amino-9-((2R,3R,4S,5R)-3,4-dihydroxy-5-hydroxymethyl-tetrahydrofuran-2-yl)-1,9-dihydro-purin-6-one (50.0 g, 177 mmol) in DMSO (133 mL) bromomethyl-benzene (25.2 mL, 212 mmol) was added dropwise. The resulting mixture was stirred for 3 h at 50° C. The mixture was cooled to rt and HCl solution (4 mol/l, 102 mL, 406 mmol) was added dropwise. The mixture was stirred for 5 h at 70° C., then at rt overnight. The obtained precipitate was filtered, washed with cold MeOH and dried to obtain the product.
MS (ESI⁺): (M+H)⁺ 242
HPLC: RT=0.28 min, Method D Intermediate 5.17

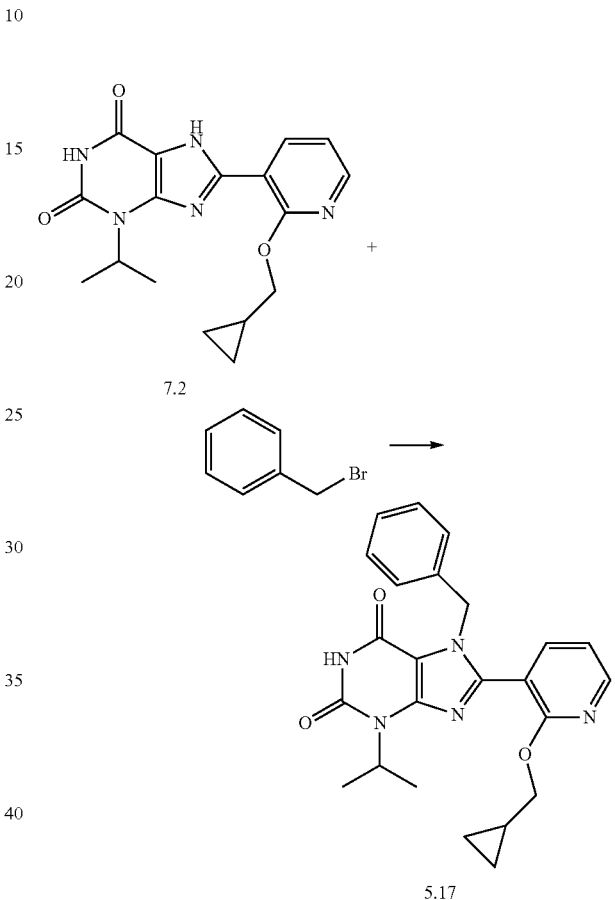

Intermediate 5.17 was prepared in an analogous manner to intermediate 5.1 using intermediate 7.2 and bromomethyl-benzene.
MS (ESI⁺): (M+H)⁺ 432
HPLC: RT=0.69 min, Method G Intermediate 5.18

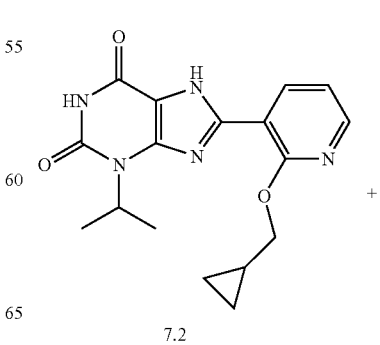

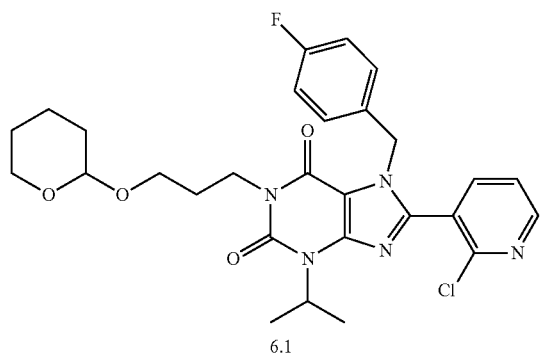

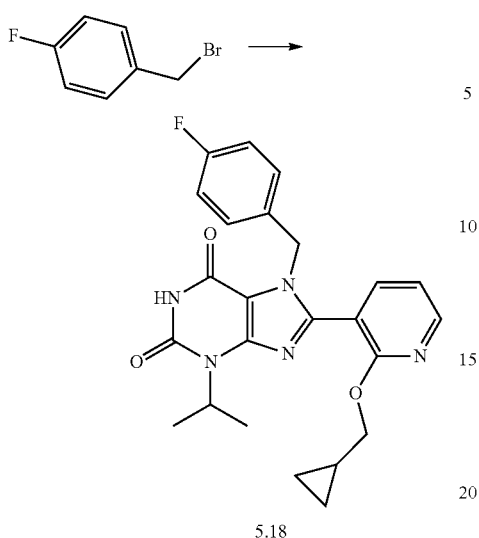

5.18

Intermediate 5.18 was prepared in an analogous manner to intermediate 5.1 using intermediate 7.2 and 1-bromomethyl-4-fluoro-benzene.

MS (ESI+): (M+H)+ 450

HPLC: RT=0.70 min, Method G

Intermediate 6.1

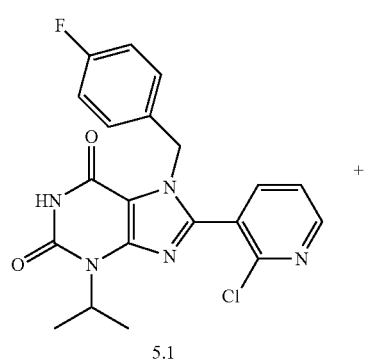

5.1

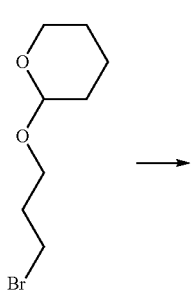

6.1

To a mixture of intermediate 5.1 (1.32 g, 3.19 mmol) in DMF (40.0 mL) K$_2$CO$_3$ (0.882 g, 6.38 mmol) and 2-(3-bromo-propoxy)-tetrahydro-pyran (0.809 mL, 4.79 mmol) were added and the mixture was stirred at 50° C. overnight. The mixture was cooled to rt, H$_2$O was added and extracted with EtOAc. The combined organic layers were washed with saturated NaCl solution, dried, concentrated in vacuo and purified by chromatography to obtain the product.

MS (ESI+): (M+H)+ 557

HPLC: RT=0.78 min, Method D

Intermediate 6.2

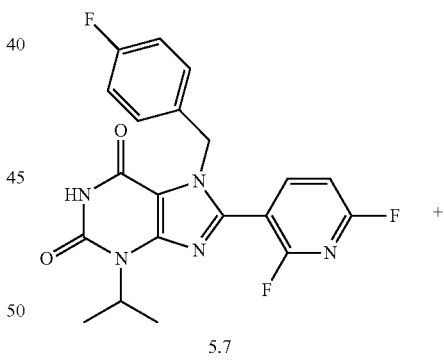

5.7

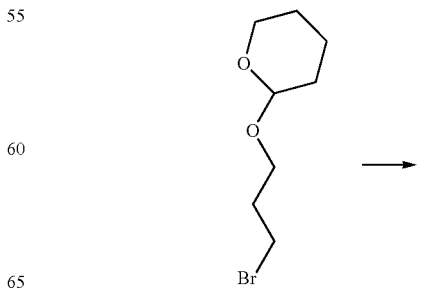

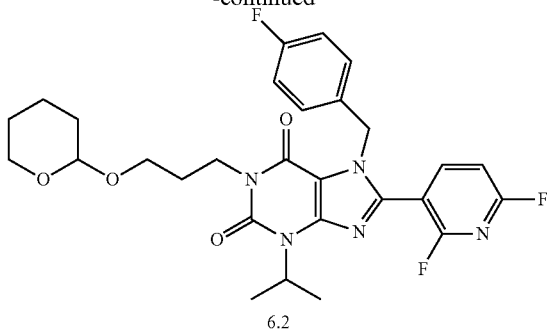

6.2

Intermediate 6.2 was prepared in an analogous manner to intermediate 6.1 using intermediate 5.7.
MS (ESI+): (M+H)+ 558
HPLC: RT=0.81 min, Method G Intermediate 6.3

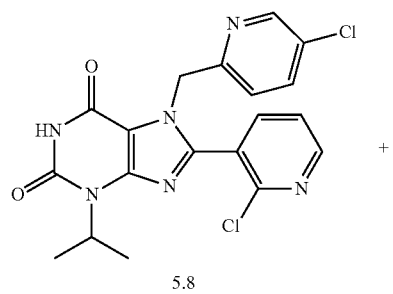

5.8

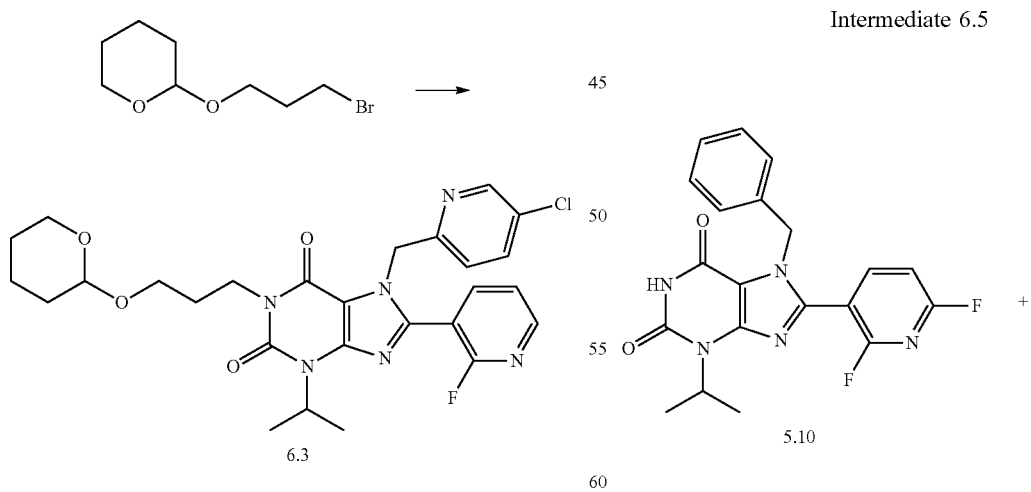

6.3

Intermediate 6.3 was prepared in an analogous manner to intermediate 5.8 using intermediate 5.7.
MS (ESI+): (M+H)+ 573
HPLC: RT=1.04 min, Method F Intermediate 6.4

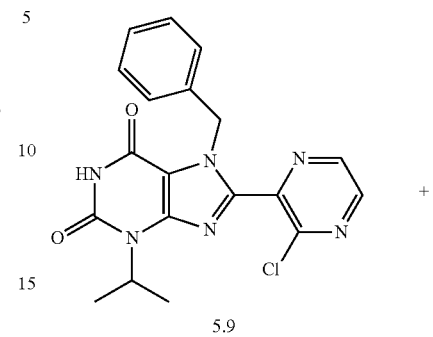

5.9

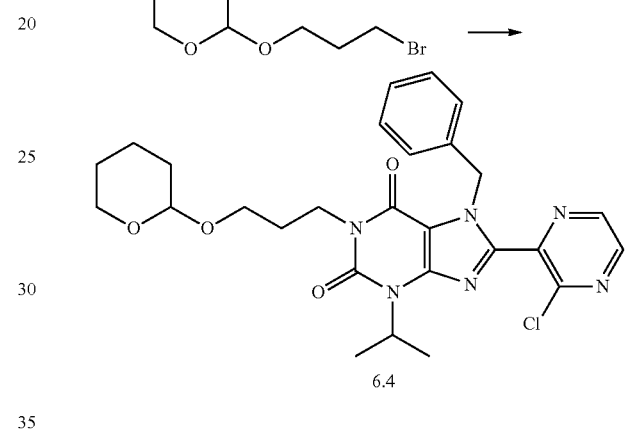

6.4

Intermediate 6.4 was prepared in an analogous manner to intermediate 6.1 using intermediate 5.9.
MS (ESI+): (M+H)+ 539
HPLC: RT=0.78 min, Method D Intermediate 6.5

5.10

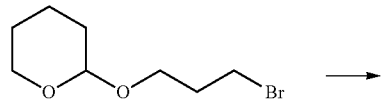

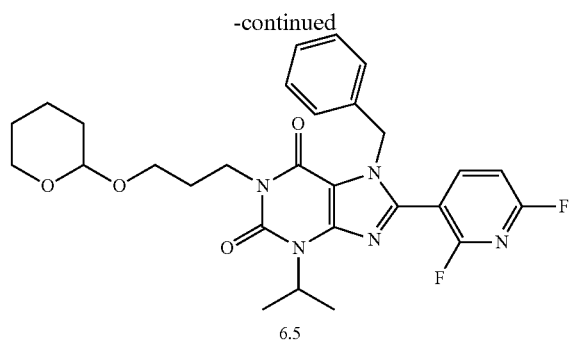

6.5

Intermediate 6.5 was prepared in an analogous manner to intermediate 6.1 using intermediate 5.10.
MS (ESI⁺): (M+H)⁺ 540
HPLC: RT=0.81 min, Method G Intermediate 6.6

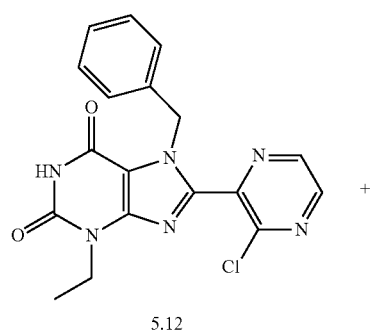

5.12

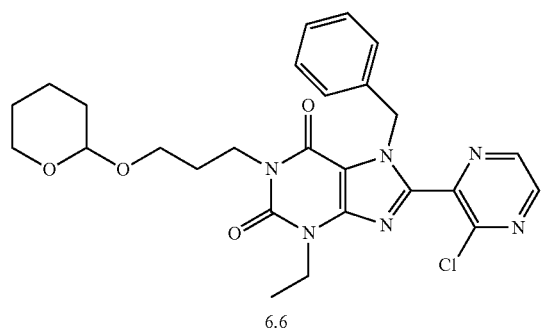

6.6

Intermediate 6.6 was prepared in an analogous manner to intermediate 6.1 using intermediate 5.12.
MS (ESI⁺): (M+H)⁺ 525
HPLC: RT=1.26 min, Method C Intermediate 6.7

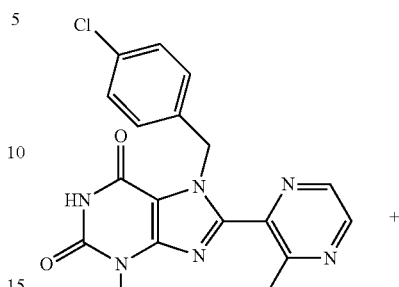

5.13

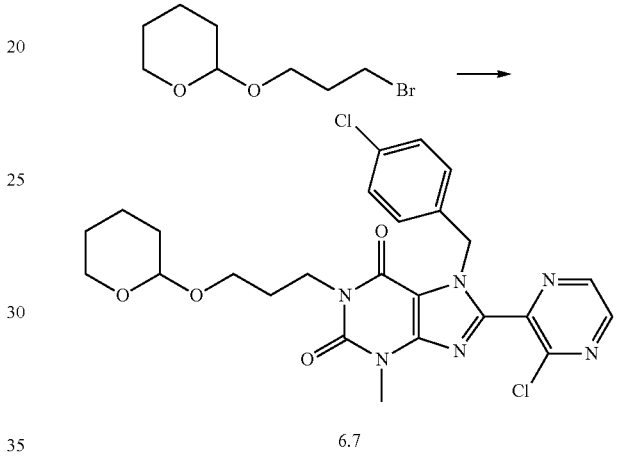

6.7

Intermediate 6.7 was prepared in an analogous manner to intermediate 6.1 using intermediate 6.7.
MS (ESI⁺): (M+H)⁺ 545
HPLC: RT=0.74 min, Method D Intermediate 6.8

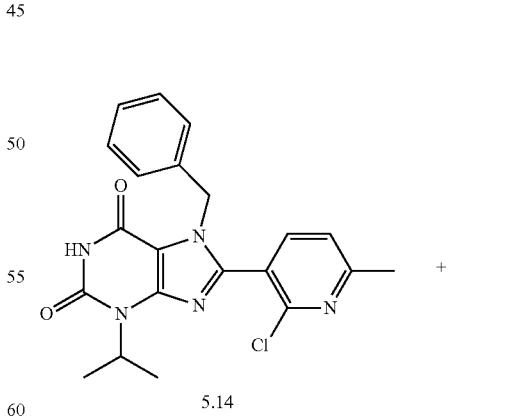

5.14

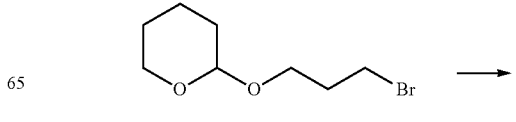

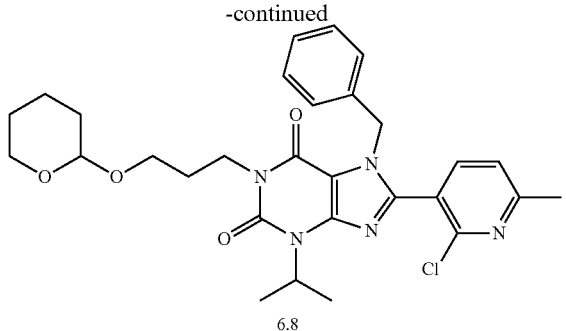

6.8

Intermediate 6.8 was prepared in an analogous manner to intermediate 6.1 using intermediate 5.14.

MS (ESI$^+$): (M+H)$^+$ 552

HPLC: RT=0.80 min, Method G

Intermediate 6.9

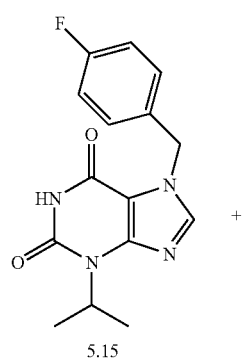

5.15

+

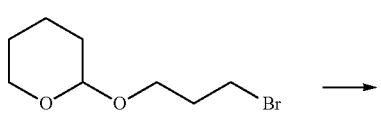

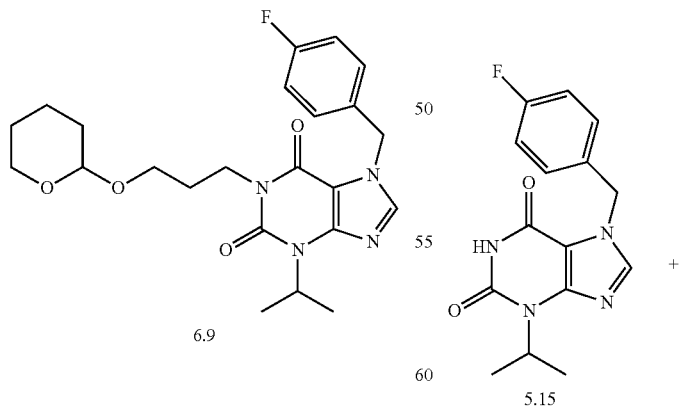

6.9

Intermediate 6.9 was prepared in an analogous manner to intermediate 6.1 using intermediate 5.15.

MS (ESI$^+$): (M+H)$^+$ 446

HPLC: RT=0.70 min, Method G

Intermediate 6.10

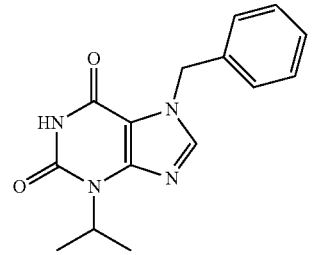

10.1

+

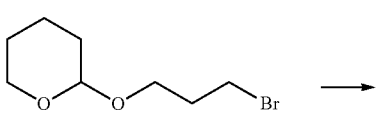

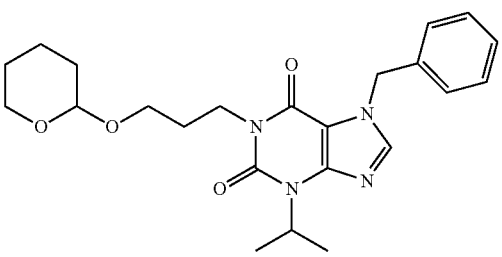

6.10

Intermediate 6.10 was prepared in an analogous manner to intermediate 6.1 using intermediate 10.1.

MS (ESI$^+$): (M+H)$^+$ 428

HPLC: RT=0.97 min, Method F

Intermediate 6.11

5.15

+

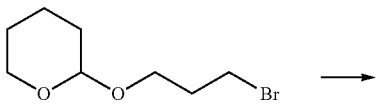

-continued

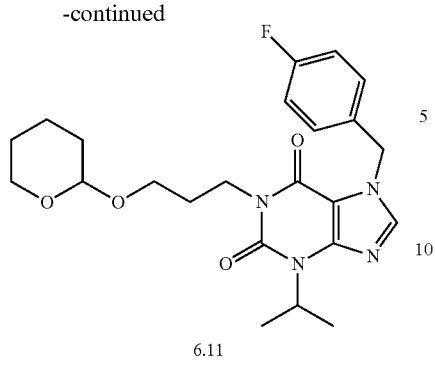

6.11

Intermediate 6.11 was prepared in an analogous manner to intermediate 6.1 using intermediate 5.15.
MS (ESI⁺): (M+H)⁺ 446
HPLC: RT=0.70 min, Method G Intermediate 7.1

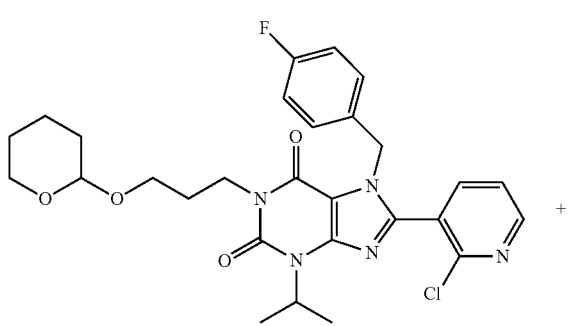

6.1

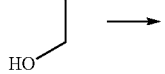

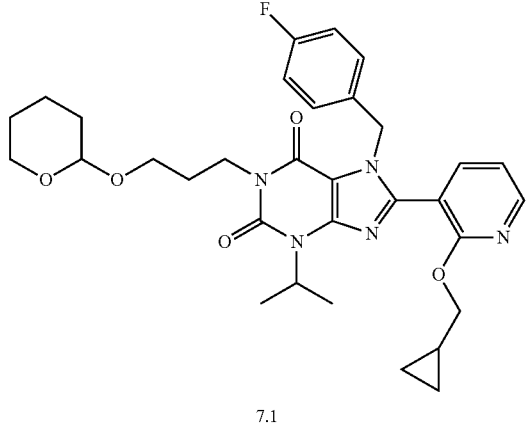

7.1

To a mixture of intermediate 6.1 (1.48 g, 2.66 mmol) and cyclopropyl-methanol (5.00 mL, 63.1 mmol) NaH (55%, 0.232 g, 5.32 mmol) was added. The mixture was stirred 4 h at 100° C. H₂O (100 mL) and NH₄Cl solution (27%, 50 mL) were added and the resulting mixture was extracted with EtOAc. The combined organic layers was washed with saturated NaCl solution (50 mL), dried, concentrated in vacuo and purified by chromatography to obtain the product.

MS (ESI⁺): (M+H)⁺ 593
HPLC: RT=0.87 min, Method D

Intermediate 7.2

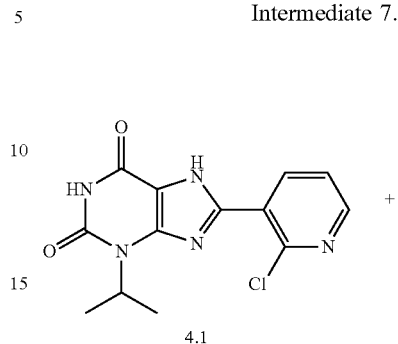

4.1

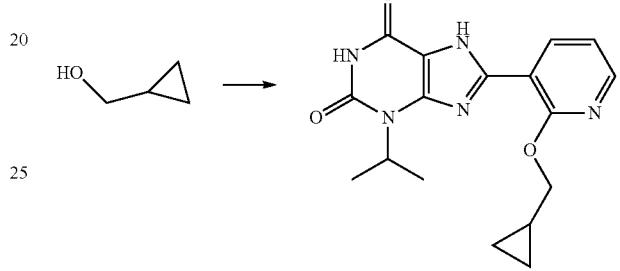

7.2

To a mixture of intermediate 4.1 (1.36 g, 4.43 mmol) in cyclopropyl-methanol (4.00 mL, 49.4 mmol) was added NaH (60%, 0.621 g, 15.5 mmol) portionwise under icebath-cooling. The mixture was stirred at 120° C. for 8 h and overnight at rt. H₂O and PE were added and the layers were separated. The pH of the aq layer was adjusted to pH=4-5 by adding HOAc. The mixture was stirred overnight, filtered and the obtained precipitate dried to give the product.

MS (ESI⁺): (M+H)⁺ 342.
HPLC: RT=0.88 min, Method F

Intermediate 7.3

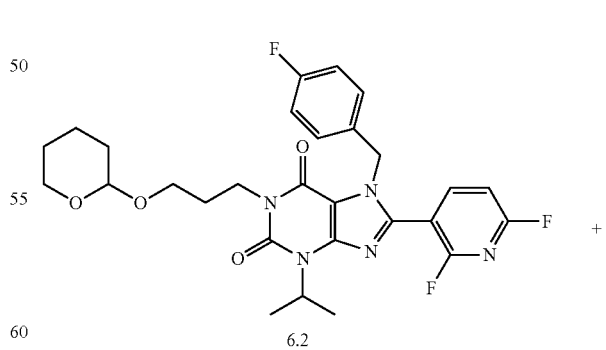

6.2

Intermediate 7.5

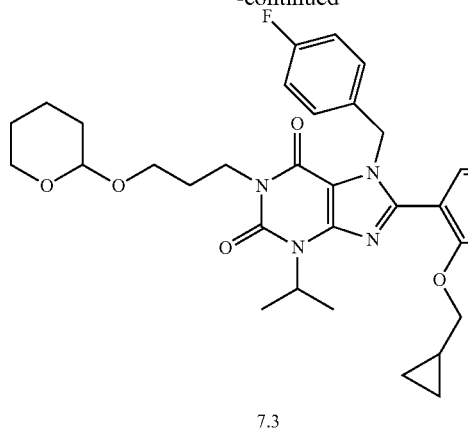

7.3

To a mixture of intermediate 6.2 (362 mg, 0.487 mmol) in dioxane (3.00 mL) cyclopropyl-methanol (39.5 µl, 0.487 mmol) and potassium 2-methyl-propan-2-olate (54.7 mg, 0.487 mmol) were added. The mixture was stirred for 2 h at 40° C. The mixture was filtered and purified by chromatography to obtain the product.
MS (ESI⁺): (M+H)⁺ 610
HPLC: RT=0.91 min, Method G Intermediate 7.4

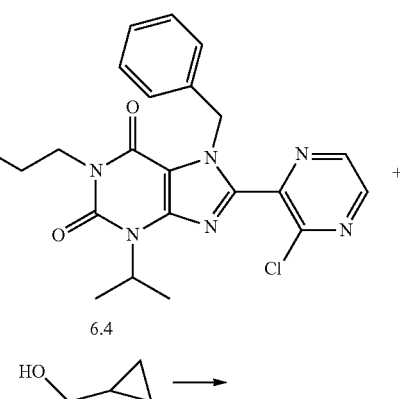

6.4

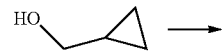

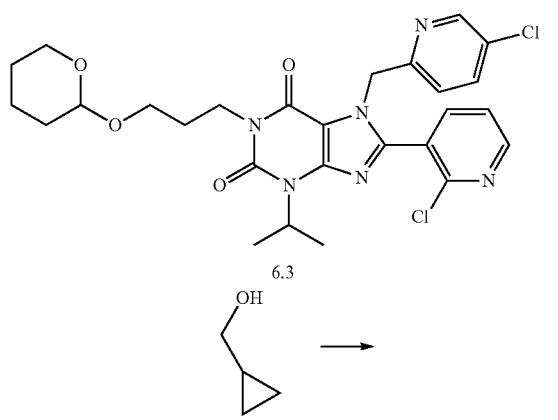

7.5

Intermediate 7.5 was prepared in an analogous manner to intermediate 7.1 using intermediate 6.4.
MS (ESI⁺): (M+H)⁺ 575
HPLC: RT=0.84 min, Method D Intermediate 7.6

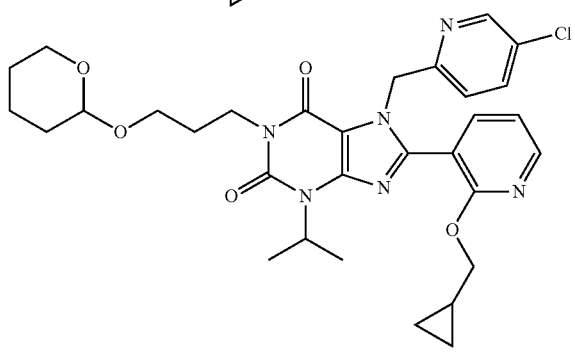

7.4

Intermediate 7.4 was prepared in an analogous manner to intermediate 7.1 using intermediate 6.3.
MS (ESI⁺): (M+H)⁺ 609
HPLC: RT=1.17 min, Method F

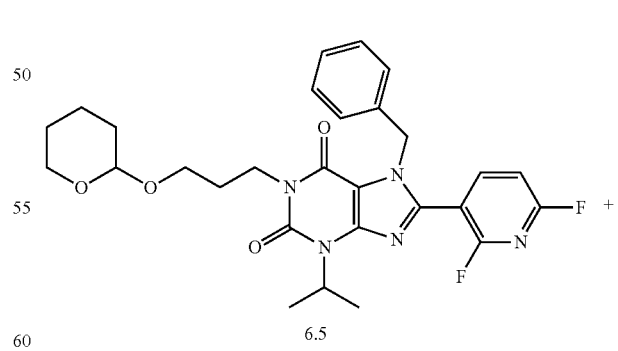

6.5

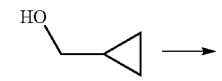

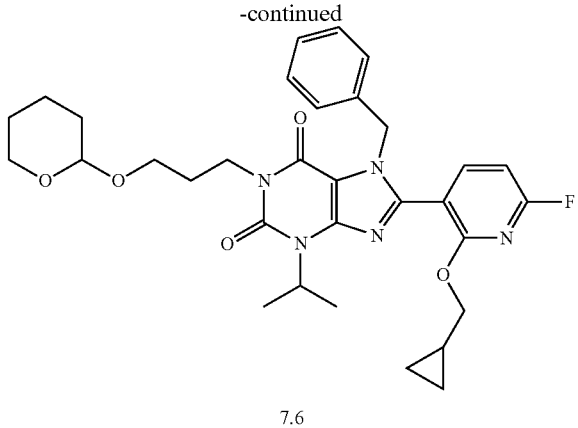

7.6

Intermediate 7.6 was prepared in an analogous manner to intermediate 7.3 using intermediate 6.5.

MS (ESI⁺): (M+H)⁺ 592

HPLC: RT=0.91 min, Method F

Intermediate 7.8

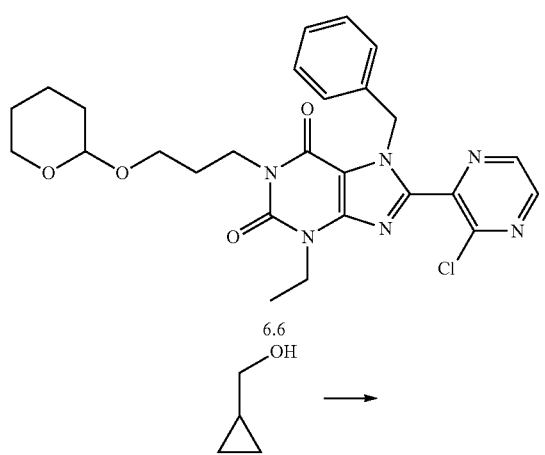

7.8

Intermediate 7.8 was prepared in an analogous manner to intermediate 7.3 using intermediate 6.6.

MS (ESI⁺): (M+H)⁺ 562

HPLC: RT=0.79 min, Method G

Intermediate 7.9

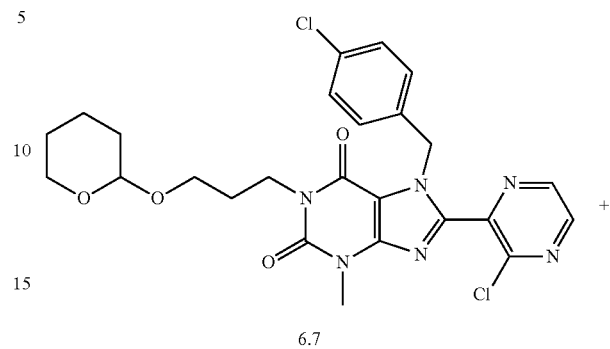

7.9

Intermediate 7.9 was prepared in an analogous manner to intermediate 7.1 using intermediate 6.7.

MS (ESI⁺): (M+H)⁺ 582

HPLC: RT=0.81 min, Method D

Intermediate 7.10

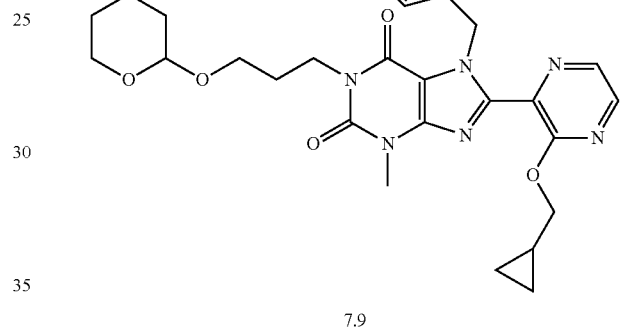

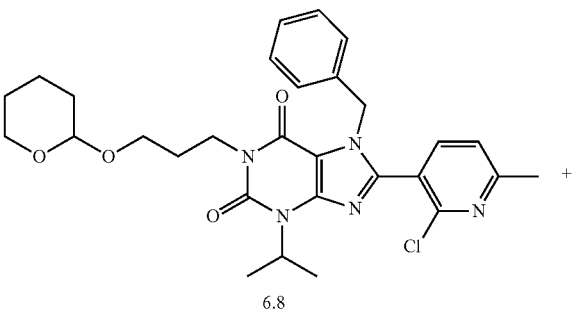

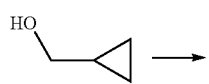

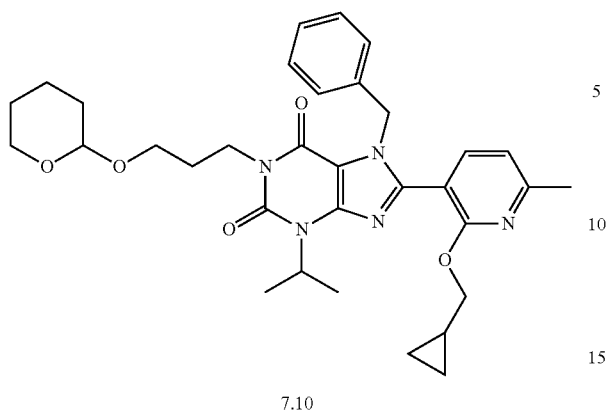

7.10

Intermediate 7.10 was prepared in an analogous manner to intermediate 7.1 using intermediate 6.8.

MS (ESI⁺): (M+H)⁺ 588

HPLC: RT=0.93 min, Method G

Intermediate 7.11

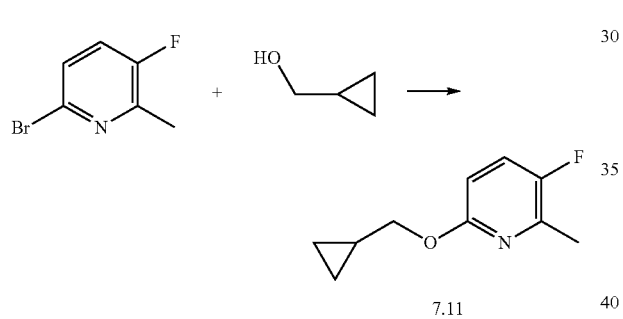

7.11

The reaction was performed under argon atmosphere. A mixture of rac-2-(di-t-butylphosphino)-1,1'-binaphthyl (210 mg, 0.526 mmol) and palladium(II) acetate (118 mg, 0.526 mmol) was stirred for 5 min. 6-bromo-3-fluoro-2-methyl-pyridine (1.00 g, 5.26 mmol), cyclopropyl-methanol (820 μl, 10.5 mmol) and Ca₂CO₃ (1.72 g, 5.26 mmol) were added and the mixture was stirred for 45 min at 140° C. in a microwave oven. The mixture was filtered and concentrated. DCM and H₂O were added and the layers were separated. The organic layer was concentrated and purified by chromatography to obtain the product.

MS (ESI⁺): (M+H)⁺ 182

HPLC: RT=0.98 min, Method F

Intermediate 7.12

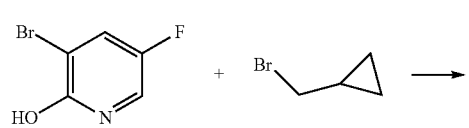

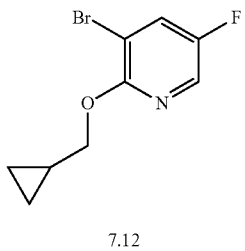

7.12

A mixture of 3-bromo-5-fluoro-pyridin-2-ol (500 mg, 2.60 mmol), cyclopropyl-methanol (505 μl, 5.21 mmol) and Ag₂CO₃ (862 mg, 3.13 mmol) in n-hexan (20.0 mL) was stirred for 10 min at 400 W in a microwave oven. The mixture was filtered off, washed with n-hexan and concentrated to obtain the product.

MS (ESI⁺): (M+H)⁺ 247

HPLC: RT=1.04 min, Method F

Intermediate 7.13

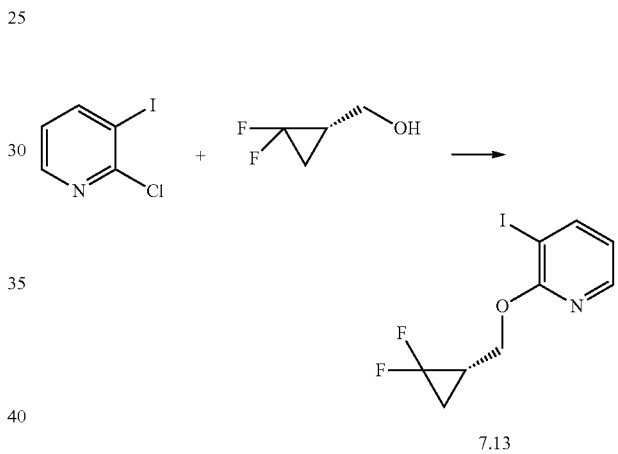

7.13

To a mixture of ((1 S)-2,2-difluoro-cyclopropyl)-methanol (prepared according to WO 2016/041845) (298 mg, 0.76 mmol) in THF (2.50 mL) NaH (150 mg, 3.76 mmol) was added. The mixture was stirred for 15 min at rt, then 2-chloro-3-iodo-pyridine (600 mg, 2.51 mmol) was added. The mixture was stirred overnight at 50° C. and cooled to rt. H₂O was added and the mixture was extracted with EtOAc. The combined organic layers were dried, concentrated in vacuo and purified by chromatography to obtain the product

MS (ESI⁺): (M+H)⁺ 312

HPLC: RT=0.97 min, Method F

Intermediate 7.14

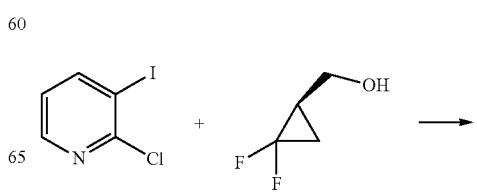

65

-continued

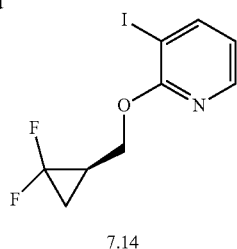

7.14

Intermediate 7.14 was prepared in an analogous manner to intermediate 7.13 using ((1R)-2,2-difluoro-cyclopropyl)-methanol (prepared according to WO 2016/041845).

MS (ESI⁺): (M+H)⁺ 312
HPLC: RT=0.97 min, Method F

Intermediate 7.15

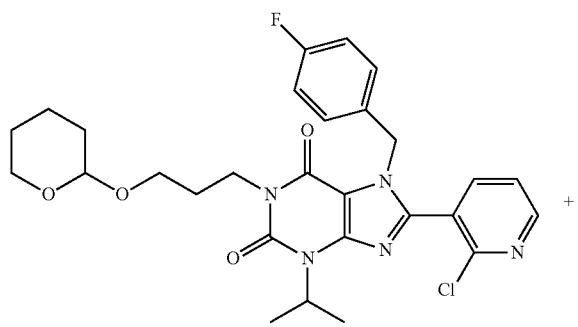

6.1

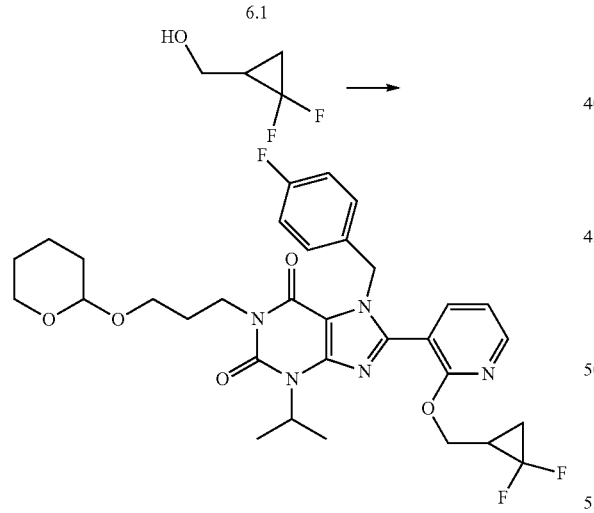

7.15

To a mixture of (2,2-difluoro-cyclopropyl)-methanol (117 mg, 1.08 mmol) in DMF (1.00 mL) was added intermediate 6.1 (300 mg, 0.540 mmol). The mixture was stirred 1 h at 50° C. H₂O and DCM were added, the layers were separated and the organic layer was dried and concentrated in vacuo to obtain the product.

MS (ESI⁺): (M+H)⁺ 629
HPLC: RT=0.85 min, Method G

66

Intermediate 8.1

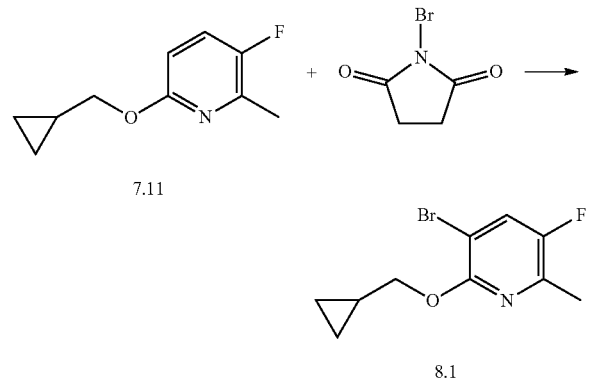

1-bromo-pyrrolidine-2,5-dione (633 mg, 3.56 mmol) was added to intermediate 7.11 (537 mg, 2.96 mmol) in DMF (5.00 mL). The mixture was stirred for 2 h at 60° C. Sodium thiosulfate solution (10%) and DCM were added and the layers were separated. The organic layer was dried, concentrated in vacuo and purified by chromatography to obtain the product.

MS (ESI⁺): (M+H)⁺ 261
HPLC: RT=1.15 min, Method F

Intermediate 9.1

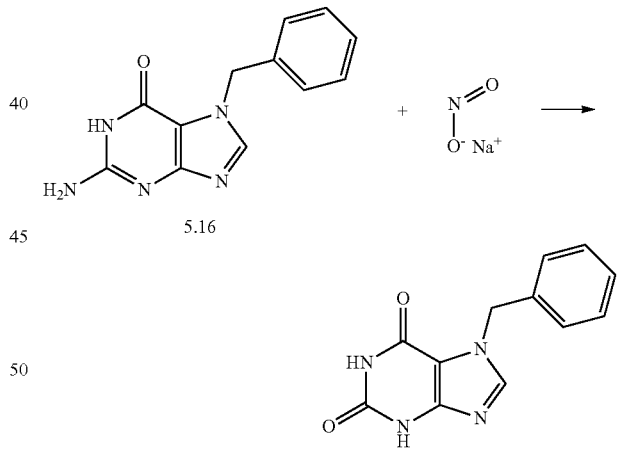

To a mixture of intermediate 5.16 (5.76 g, 23.9 mmol) in HOAc (80.0 mL) and H₂O, a solution of NaNO₂ (3.30 g, 47.8 mmol) in H₂O was added dropwise at 50° C. The mixture was stirred for 30 min at 50° C. Another equivalent of NaNO₂ (1 equiv) in H₂O was added dropwise. The mixture was stirred for 30 min at 50° C. and cooled to rt. The resulting precipitate was filtered off, washed with H₂O, suspended in H₂O/ACN and freeze dried to give the product.

MS (ESI⁺): (M+H)⁺ 243.1
HPLC: RT=0.37 min, Method A

Intermediate 10.1

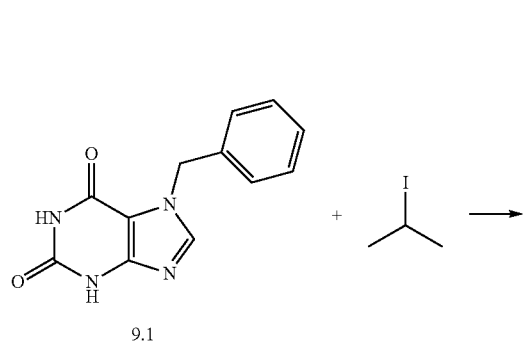

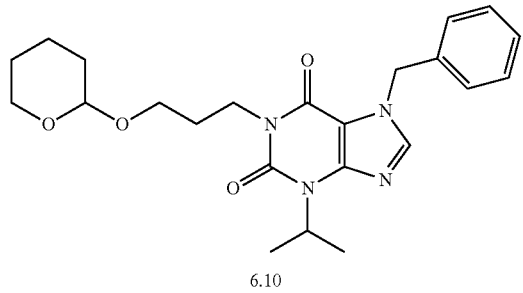

A mixture of intermediate 9.1 (2.64 g, 10.9 mmol) in DMF (45.0 mL) was heated to 50° 0, then NaH (476 mg, 10.9 mmol) was added. The mixture was stirred 2 h. 2-Iodo-propane (5.45 mL, 54.5 mmol) was added and the mixture was stirred for 2 h at 80° C. The mixture was cooled to rt and purified by chromatography to obtain the product.

MS (ESI$^+$): (M+H)$^+$ 285

HPLC: RT=0.65 min, Method F

Intermediate 11.1

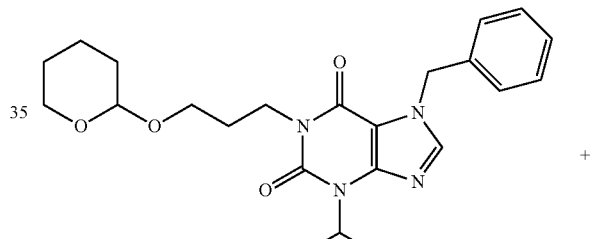

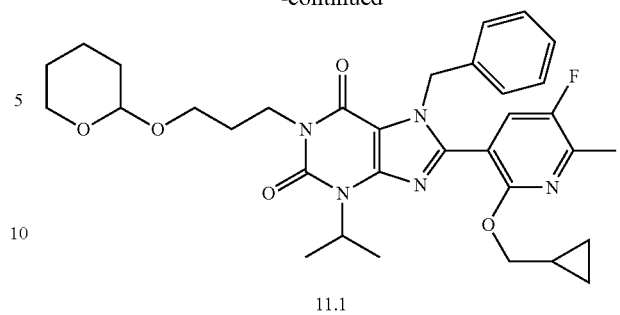

A mixture of intermediate 8.1 (61.0 mg, 0.234 mmol), intermediate 6.10 (100 mg, 0.234 mmol), copper(I)iodide (134 mg, 0.703 mmol), palladium acetate (10.5 mg, 0.047 mmol), tricyclohexylphosphine (26.3 mg, 0.094 mmol) and K$_2$CO$_3$ (64.8 mg, 0.469 mmol) in THF (207 µl) and DMF (438 µl) was stirred at 130° C. overnight. MeOH was added, the resulting mixture was filtered, concentrated in vacuo and purified by chromatography to obtain the product.

MS (ESI$^+$): (M+H)$^+$ 607

HPLC: RT=0.96 min, Method G

Intermediate 11.2

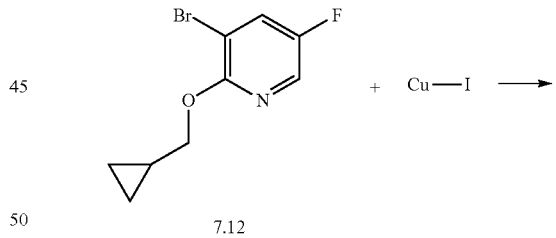

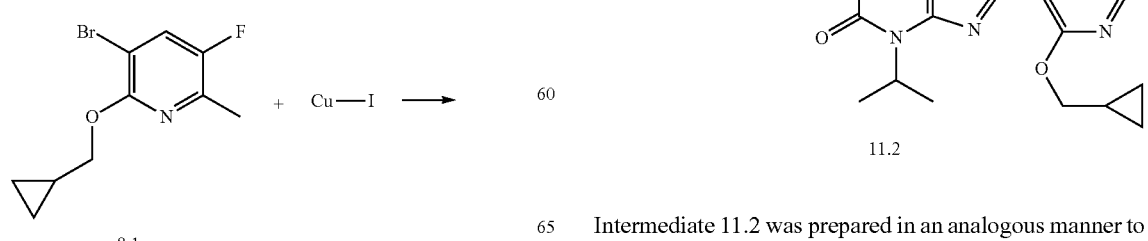

Intermediate 11.2 was prepared in an analogous manner to intermediate 11.1 using intermediate 6.10 and intermediate 7.12.

MS (ESI⁺): (M+H)⁺ 593
HPLC: RT=0.91 min, Method G

Intermediate 11.3

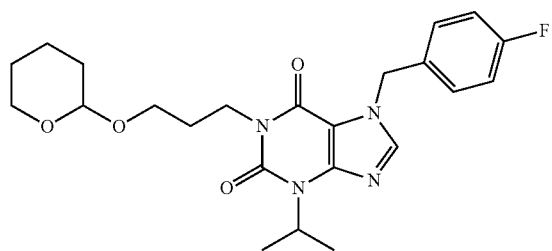
6.11

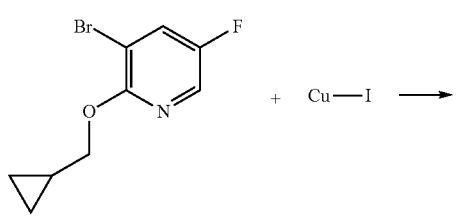
7.12

+ Cu—I →

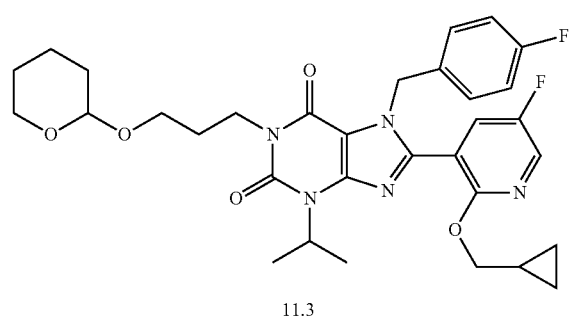
11.3

Intermediate 11.3 was prepared in an analogous manner to intermediate 11.1 using intermediate 6.11 and intermediate 7.12.
MS (ESI⁺): (M+H)⁺ 611
HPLC: RT=0.91 min, Method G Intermediate 11.4

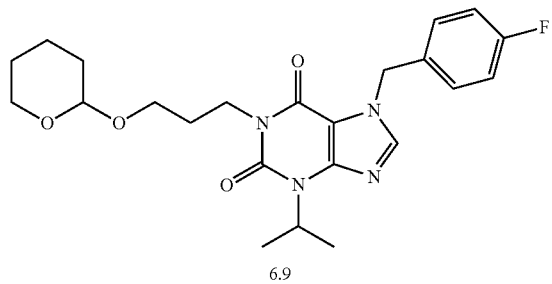
6.9

+

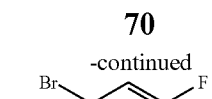
8.1

→

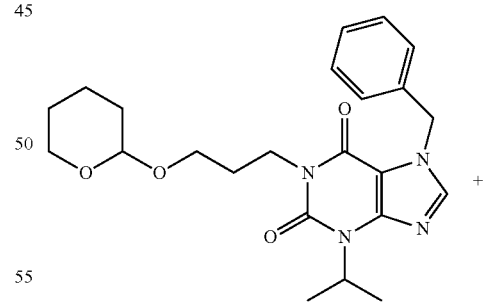
11.4

Intermediate 11.4 was prepared in an analogous manner to intermediate 11.1 using intermediate 6.9 and intermediate 8.1.
MS (ESI⁺): (M+H)⁺ 625
HPLC: RT=0.96 min, Method G Intermediate 11.5

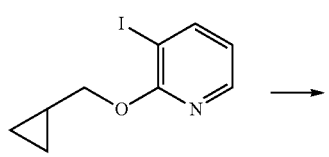
6.10

+

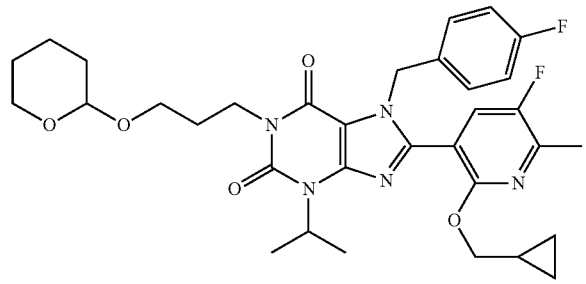

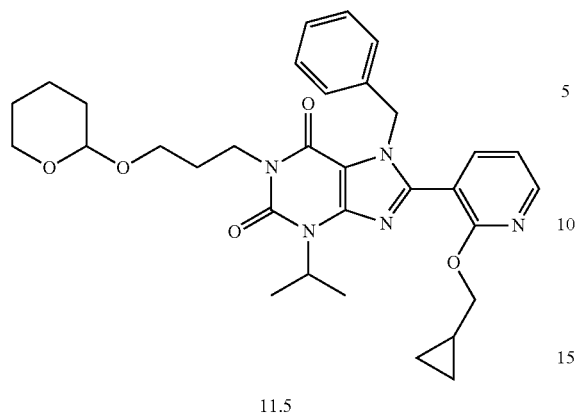

11.5

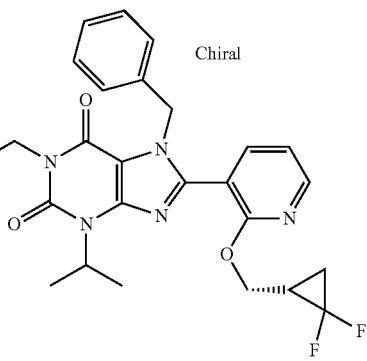

11.6

The reaction was performed under argon. A mixture of intermediate 6.10 (200 mg, 0.469 mmol), 2-cyclopropyl-methoxy-3-iodo-pyridine (258 mg, 0.938 mmol), copper(I) iodide (268 mg, 1.41 mmol), palladium acetate (21.1 mg, 0.094 mmol), triphenylphosphine (49.2 mg, 0.188 mmol) and K$_2$CO$_3$ (130 mg, 0.938 mmol) in THF (6.02 mL) and DMF (3.05 mL) was stirred at 180° C. for 3 h and 44 min in a microwave. The mixture was filtered off and purified by chromatography to give the product.

MS (ESI$^+$): (M+H)$^+$ 574.3

HPLC: RT=1.21 min, Method F

Intermediate 11.6

The reaction was performed under argon. A mixture of intermediate 6.10 (200 mg, 0.469 mmol), intermediate 7.13 (201 mg, 0.647 mmol), copper(I)iodide (268 mg, 1.41 mmol), palladium acetate (21.1 mg, 0.094 mmol), tricyclo-hexylphosphine (52.6 mg, 0.188 mmol) and K$_2$CO$_3$ (260 mg, 1.88 mmol) in THF (469 µL) and DMF (938 µL) was stirred at 130° C. for 12 h. Diluted NH$_3$ solution was added and extracted three times with EtOAc. The organic layers were dried and concentrated in vacuo to give the product.

MS (ESI$^+$): (M+H)$^+$ 610

HPLC: RT=1.16 min, Method F

Intermediate 11.7

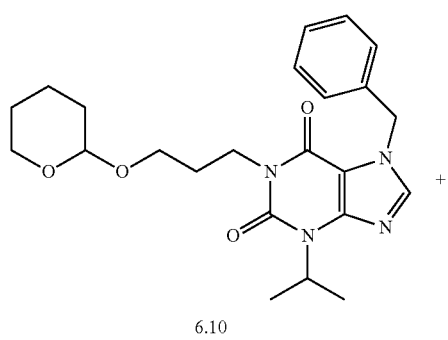

6.10

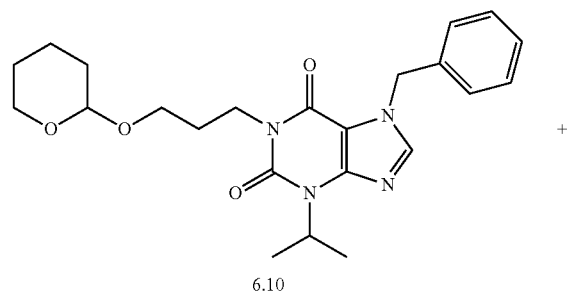

6.10

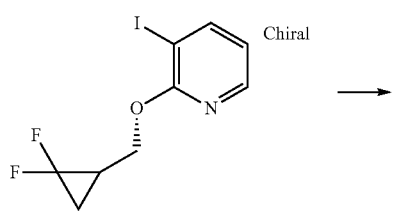

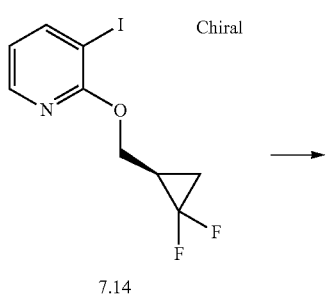

7.14

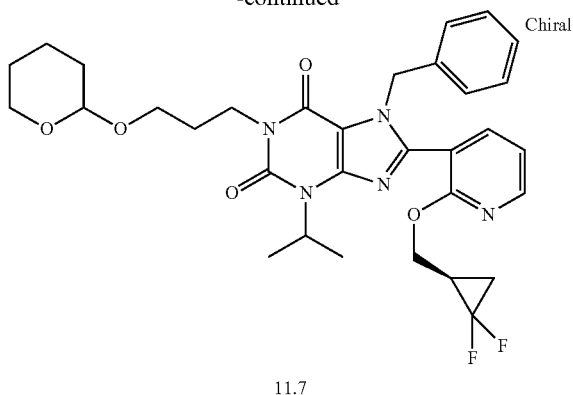

11.7

Intermediate 11.7 was prepared in an analogous manner to intermediate 11.6 using intermediate 6.10 and intermediate 7.14.

MS (ESI$^+$): (M+H)$^+$ 610.8
HPLC: RT=1.15 min, Method F

Intermediate 12.1

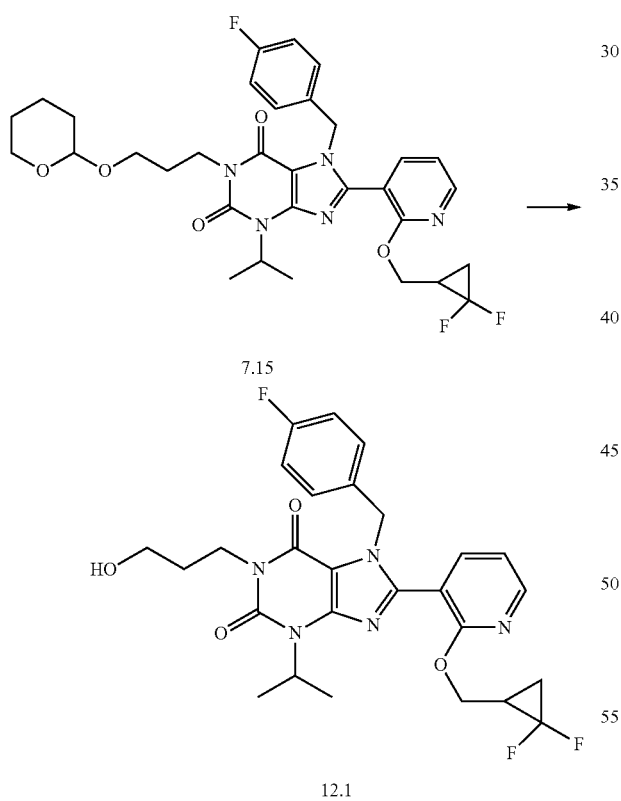

7.15

↓

12.1

To a mixture of intermediate 7.15 (338 mg, 0.539 mmol) in MeOH (3.00 mL) was added toluene-4-sulfonic acid monohydrate (512 mg, 2.69 mmol). The mixture was stirred at rt for 1 h and purified by chromatography to obtain the product.

MS (ESI$^+$): (M+H)$^+$ 545
HPLC: RT=0.71 min, Method G

Intermediate 13.1

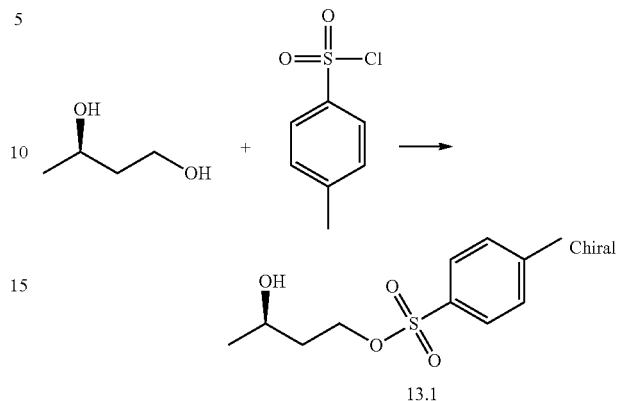

13.1

To a mixture of (3R)-butane-1,3-diol (500 mg, 5.55 mmol) in DCM (16.3 mL) was added TEA (3.19 mL, 22.7 mmol). The mixture was cooled with an icebath, 4-methyl-benzenesulfonyl chloride (1.16 g, 6.10 mmol) was added and stirred at rt overnight. Saturated NH$_4$Cl solution and DCM were added and the layers were separated. The aq layer was twice extracted with DCM. The combined organic layers was washed with H$_2$O, concentrated in vacuo and purified by chromatography to obtain the product.

MS (ESI$^+$): (M+H)$^+$ 245
HPLC: RT=0.68 min, Method F

EXAMPLES

Example 1

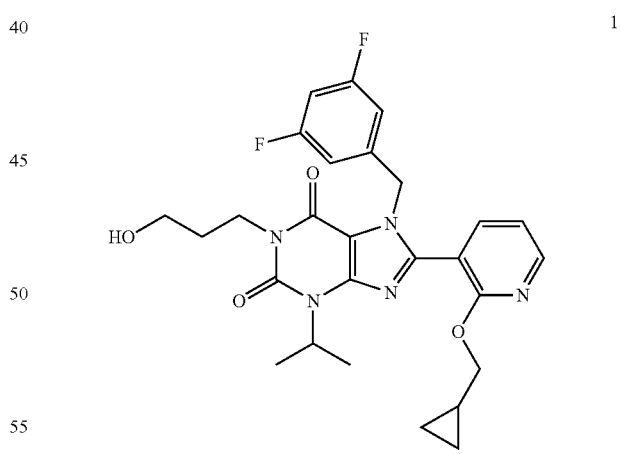

1

To a mixture of intermediate 5.2 (80.0 mg, 0.171 mmol) in ACN (1.00 mL) K$_3$PO$_4$ (54.5 mg, 0.257 mmol) was added. Then 3-bromo-propan-1-ol (29.7 mg, 0.214 mmol) was added and the mixture was stirred at 90° C. for 3 h and 15 min. The mixture was cooled to rt and purified by chromatography to obtain the product.

MS (ESI$^+$): (M+H)$^+$ 526
HPLC: RT=0.74 min, Method G
$^1$H NMR (400 MHz, DMSO-d$_6$) δ 8.34 (dd, J=1.89, 4.93 Hz, 1H), 7.84 (dd, J=1.89, 7.45 Hz, 1H), 7.05-7.14 (m, 2H), 6.61-6.66 (m, 2H), 5.52 (s, 2H), 5.11 (spt, J=6.9 Hz, 1H), 4.41 (t, J=5.18 Hz, 1H), 4.13 (d, J=7.07 Hz, 2H), 3.90-3.96 (m, 2H), 3.34-3.47 (m, 2H), 2.52-2.54 (m, 1H), 1.66-1.74 (m, 2H), 1.53 (d, J=6.9 Hz, 6H), 1.11-1.21 (m, 1H), 0.45-0.52 (m, 2H), 0.25-0.30 (m, 2H).

Example 2

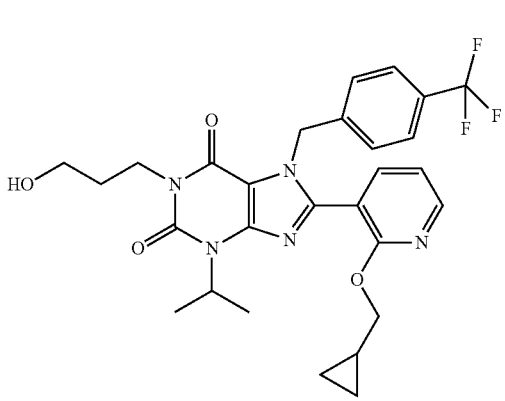

Example 2 was prepared in an analogous manner to Example 1 using intermediate 5.3.

MS (ESI$^+$): (M+H)$^+$ 558

RT=0.79 min, Method G $^1$H NMR (400 MHz, DMSO-d$_6$) δ 8.33 (dd, J=1.9, 4.9 Hz, 1H), 7.83 (dd, J=2.0, 7.3 Hz, 1H), 7.59 (d, J=8.1 Hz, 2H), 7.08-7.16 (m, 3H), 5.60 (s, 2H), 5.11 (sept, J=6.9 Hz, 1H), 4.42 (br s, 1H), 4.09 (d, J=7.1 Hz, 2H), 3.88-3.96 (m, 2H), 3.39-3.48 (m, 2H), 3.18 (br s, 1H), 1.64-1.76 (m, 2H), 1.53 (d, J=6.9 Hz, 6H), 1.08-1.20 (m, 1H), 0.44-0.51 (m, 2H), 0.23-0.28 (m, 2H).

Example 3

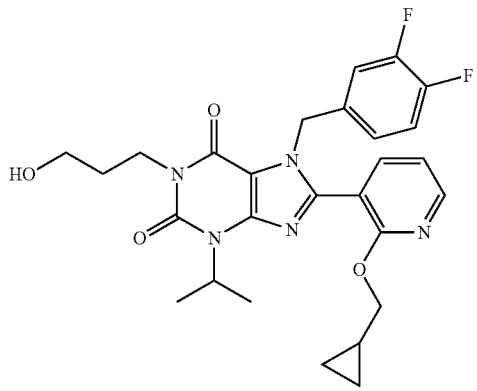 [SMILES: CC(C)n1c(=O)n(CCCO)c(=O)c2c1nc(-c1cccnc1OCC1CC1)n2Cc1ccc(F)c(F)c1]

Example 3 was prepared in an analogous manner to Example 1 using intermediate 5.4.

MS (ESI$^+$): (M+H)$^+$ 526

HPLC RT=0.74 min, Method G $^1$H NMR (DMSO-d$_6$) δ 8.35 (dd, J=2.0, 5.1 Hz, 1H), 7.81 (dd, J=2.0, 7.3 Hz, 1H), 7.28 (td, J=8.5, 10.8 Hz, 1H), 7.12 (dd, J=4.9, 7.5 Hz, 1H), 6.95-7.02 (m, 1H), 6.73 (ddd, J=1.9, 4.1, 6.4 Hz, 1H), 5.50 (s, 2H), 5.10 (spt, J=6.9 Hz, 1H), 4.42 (t, J=5.2 Hz, 1H), 4.16 (d, J=7.3 Hz, 2H), 3.90-3.97 (m, 2H), 3.36-3.47 (m, 2H), 1.65-1.77 (m, 2H), 1.52 (d, J=6.9 Hz, 6H), 1.13-1.23 (m, 1H), 0.44-0.53 (m, 2H), 0.27-0.34 (m, 2H).

Example 4

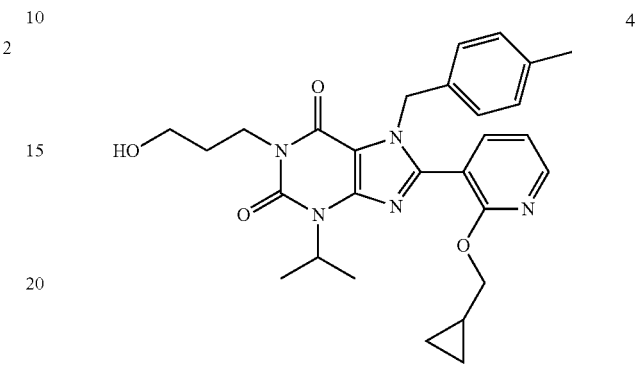

Example 4 was prepared in an analogous manner to Example 1 using intermediate 5.5.

MS (ESP): (M+H)$^+$ 504

HPLC: RT=0.76 min, Method G $^1$H NMR (DMSO-d$_6$) δ 8.35 (dd, J=1.9, 5.0 Hz, 1H), 7.77 (dd, J=1.9, 7.4 Hz, 1H), 7.10 (dd, J=5.0, 7.4 Hz, 1H), 6.97-7.02 (m, J=8.0 Hz, 2H), 6.75-6.79 (m, J=8.0 Hz, 2H), 5.50 (s, 2H), 5.09 (spt, J=6.9 Hz, 1H), 4.44 (br s, 1H), 4.19 (d, J=7.2 Hz, 2H), 3.90-3.98 (m, 2H), 3.45 (br d, J=3.7 Hz, 2H), 2.19 (s, 3H), 1.66-1.75 (m, 2H), 1.51 (d, J=6.9 Hz, 6H), 1.17-1.28 (m, 1H), 0.46-0.54 (m, 2H), 0.29-0.37 (m, 2H).

Example 5

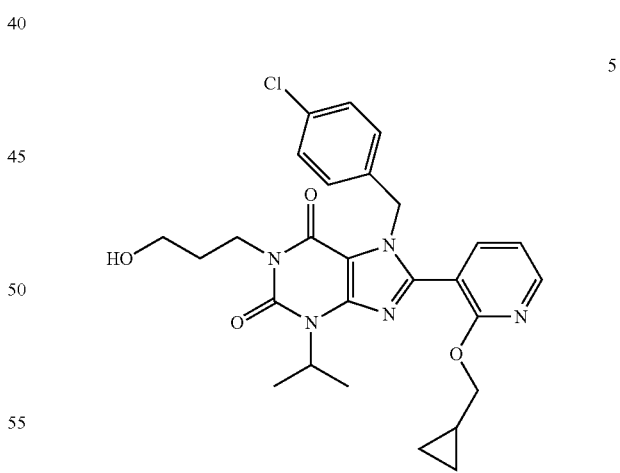

Example 5 was prepared in an analogous manner to Example 1 using intermediate 5.6.

MS (ESI$^+$): (M+H)$^+$ 524

RT=0.77 min, Method G $^1$H NMR (DMSO-d$_6$) δ 8.34 (dd, J=1.9, 4.9 Hz, 1H), 7.79 (dd, J=2.0, 7.3 Hz, 1H), 7.27 (d, J=7.9 Hz, 2H), 7.11 (dd, J=5.0, 7.3 Hz, 1H), 6.92 (d, J=8.6 Hz, 2H), 5.52 (s, 2H), 5.10 (spt, J=6.9 Hz, 1H), 4.42 (t, J=5.2 Hz, 1H), 4.16 (d, J=7.1 Hz, 2H), 3.90-3.97 (m, 2H), 3.35-3.47 (m, 2H), 1.67-1.80

(m, 2H), 1.52 (d, J=6.9 Hz, 6H), 1.14-1.24 (m, 1H), 0.45-0.54 (m, 2H), 0.25-0.35 (m, 2H).

Example 6

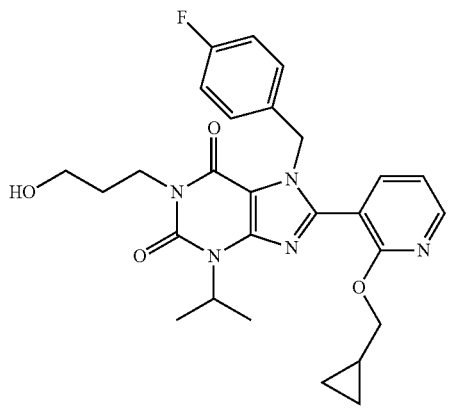

To a mixture of intermediate 7.1 (58.0 mg, 0.10 mmol) in MeOH (2.0 mL) and THF (4.0 mL) p-toluenesulfonic acid (18.6 mg, 0.11 mmol) was added. The mixture was stirred at rt for 2 h. To the mixture was basified with $NH_4OH$ to pH 8, concentrated in vacuo and purified by chromatography to obtain the product.

MS (ESI$^+$): (M+H)$^+$ 509
HPLC: RT=0.74 min, Method D
$^1$H NMR (DMSO-$d_6$) δ 8.34 (dd, J=1.89, 4.9 Hz, 1H), 7.78 (dd, J=2.0, 7.3 Hz, 1H), 7.00-7.12 (m, 3H), 6.91-6.96 (m, 2H), 5.52 (s, 2H), 5.10 (spt, J=6.9 Hz, 1H), 4.44 (br t, J=4.8 Hz, 1H), 4.18 (d, J=7.3 Hz, 2H), 3.91-3.97 (m, 2H), 3.42-3.48 (m, 2H), 1.66-1.75 (m, 2H), 1.52 (d, J=6.9 Hz, 6H), 1.16-1.26 (m, 1H), 0.47-0.53 (m, 2H), 0.28-0.32 (m, 2H).

Example 7

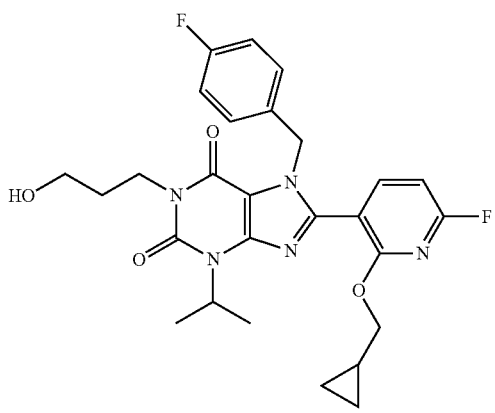

Example 7 was prepared in an analogous manner to Example 6 using intermediate 7.3.
MS (ESP): (M+H)$^+$ 526
HPLC: RT=0.77 min, Method G
$^1$H NMR (DMSO-$d_6$) δ 7.96 (t, J=8.1 Hz, 1H), 6.95-7.08 (m, 4H), 6.85 (dd, J=2.6, 8.1 Hz, 1H), 5.50 (s, 2H), 5.09 (spt, J=6.9 Hz, 1H), 4.41 (t, J=5.3 Hz, 1H), 4.12 (d, J=7.2 Hz, 2H), 3.91-3.97 (m, 2H), 3.42-3.48 (m, 2H), 1.66-1.76 (m, 2H), 1.51 (d, J=6.9 Hz, 6H), 1.02-1.29 (m, 3H), 0.46-0.57 (m, 2H), 0.28-0.36 (m, 2H).

Example 8

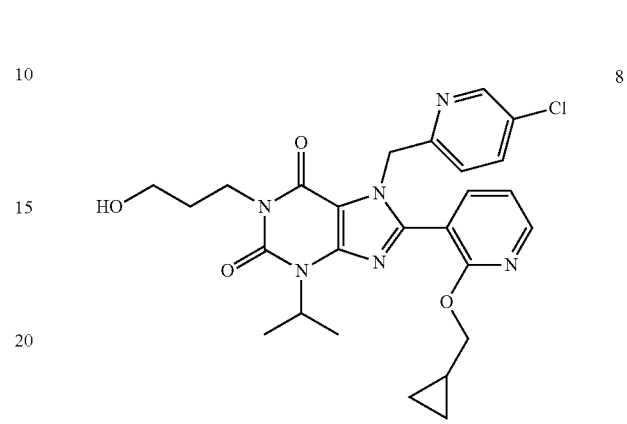

Example 8 was prepared in an analogous manner to Example 6 using intermediate 7.4.
MS (ESI$^+$): (M+H)$^+$ 525
HPLC: RT=0.95 min, Method F
$^1$H NMR (DMSO-$d_6$) δ 8.42 (d, J=2.5 Hz, 1H), 8.29 (dd, J=1.9, 4.9 Hz, 1H), 7.80 (td, J=2.4, 7.9 Hz, 2H), 7.16 (d, J=8.3 Hz, 1H), 7.1 (dd, J=5.05, 7.33 Hz, 1H), 5.60 (s, 2H), 5.11 (spt, J=6.9 Hz, 1H), 4.40 (t, J=5.2 Hz, 1H), 4.12 (d, J=7.1 Hz, 2H), 3.85-3.93 (m, 2H), 3.38-3.45 (m, 2H), 1.64-1.71 (m, 2H), 1.54 (d, J=6.9 Hz, 6H), 1.12-1.22 (m, 1H), 0.45-0.53 (m, 2H), 0.26-0.32 (m, 2H).

Example 9

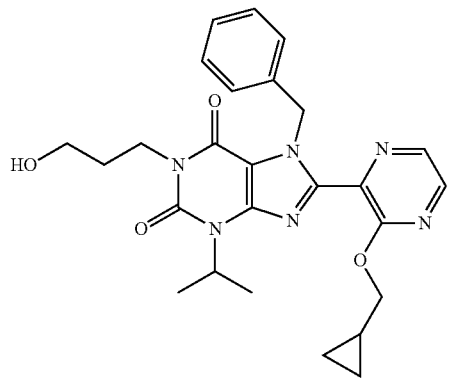

Example 9 was prepared in an analogous manner to Example 6 using intermediate 7.5.
MS (ESI$^+$): (M+H)$^+$ 491
HPLC: RT=0.69 min, Method D
$^1$H NMR (DMSO-$d_6$) (8.39 (d, J=2.7 Hz, 1H), 8.34 (d, J=2.7 Hz, 1H), 7.18-7.23 (m, 3H), 6.93-6.98 (m, 2H), 5.69 (s, 2H), 5.12 (spt, J=6.9 Hz, 1H), 4.35-4.46 (m, 1H), 4.17 (d, J=7.0 Hz, 2H), 3.91-3.98 (m, 2H), 3.42-3.48 (m, 2H), 1.68-1.76 (m, 2H), 1.54 (d, J=6.9 Hz, 6H), 1.12-1.22 (m, 1H), 0.45-0.53 (m, 2H), 0.28-0.35 (m, 2H)

Example 10

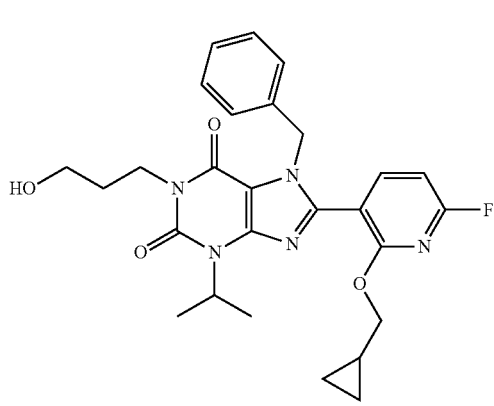 [SMILES: CC(C)n1c(=O)n(CCCO)c(=O)c2c1nc(-c1ccc(F)nc1OCC1CC1)n2Cc1ccccc1]

Example 10 was prepared in an analogous manner to Example 6 using intermediate 7.6.

MS (ESI+): (M+H)+ 508

HPLC: RT=0.76 min, Method G $^1$H NMR (DMSO-$d_6$) δ 7.96 (t, J=8.1 Hz, 1H), 7.17-7.25 (m, 3H), 6.89-6.95 (m, 2H), 6.84 (dd, J=2.7, 8.1 Hz, 1H), 5.53 (s, 2H), 5.09 (spt, J=6.9 Hz, 1H), 4.43 (t, J=5.3 Hz, 1H), 4.11 (d, J=7.2 Hz, 2H), 3.90-3.97 (m, 2H), 3.33-3.47 (m, 2H), 1.67-1.75 (m, 2H), 1.52 (d, J=6.9 Hz, 6H), 1.13-1.25 (m, 1H), 0.49-0.57 (m, 2H), 0.29-0.37 (m, 2H).

Example 11

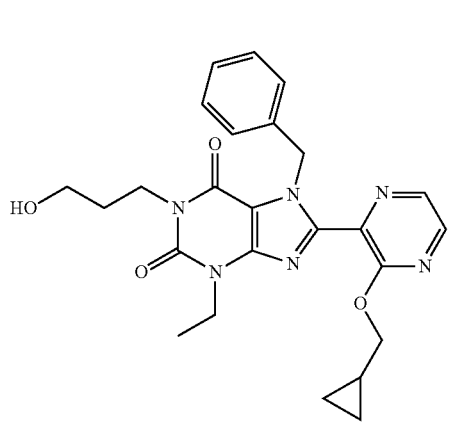

Example 11 was prepared in an analogous manner to Example 6 using intermediate 7.8.

MS (ESI+): (M+H)+ 477.4

HPLC: RT=0.62 min, Method G $^1$H NMR (400 MHz, DMSO-$d_6$) δ 8.40 (d, J=2.7 Hz, 1H), 8.35 (d, J=2.7 Hz, 1H), 7.17-7.24 (m, 3H), 6.91-6.97 (m, 2H), 5.65 (s, 2H), 4.44 (t, J=5.2 Hz, 1H), 4.17 (d, J=7.0 Hz, 2H), 4.07 (q, J=7.0 Hz, 2H), 3.91-4.00 (m, 2H), 3.33-3.48 (m, 2H), 1.72 (quin, J=6.9 Hz, 2H), 1.26 (t, J=7.03 Hz, 3H), 1.10-1.20 (m, 1H), 0.44-0.54 (m, 2H), 0.29-0.36 (m, 2H).

Example 12

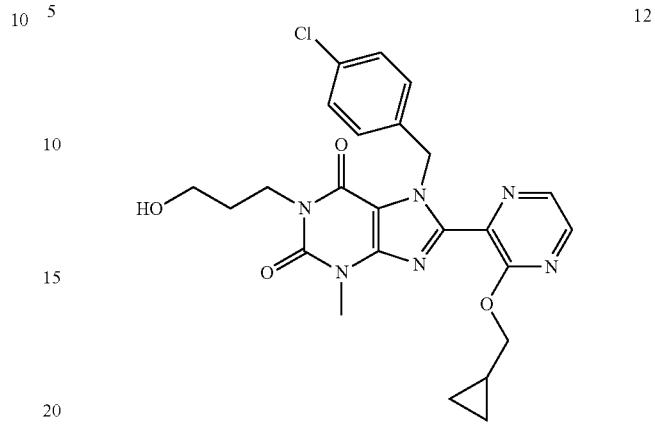

Example 12 was prepared in an analogous manner to Example 6 using intermediate 7.9.

MS (ESI+): (M+H)+ 497

HPLC: RT=0.65 min, Method D $^1$H NMR (DMSO-$d_6$) δ 8.40 (d, J=2.7 Hz, 1H), 8.34 (d, J=2.7 Hz, 1H), 7.25-7.32 (m, 2H), 6.93-7.00 (m, 2H), 5.62 (s, 2H), 4.41 (t, J=5.3 Hz, 1H), 4.19 (d, J=6.97 Hz, 2H), 3.93-3.97 (m, 2H), 3.43-3.49 (m, 5H), 1.69-1.76 (m, 2H), 1.12-1.33 (m, 1H), 0.45-0.55 (m, 2H), 0.26-0.37 (m, 2H).

Example 13

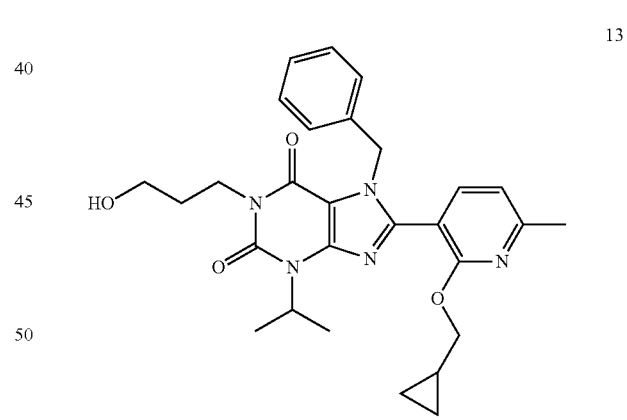

Example 13 was prepared in an analogous manner to Example 6 using intermediate 7.10.

MS (ESI+): (M+H)+ 504

HPLC: RT=0.80 min, Method G $^1$H NMR (DMSO-$d_6$) δ 7.66 (d, J=7.6 Hz, 1H), 7.16-7.23 (m, 3H), 6.95 (d, J=7.6 Hz, 1H), 6.90 (dd, J=1.7, 7.5 Hz, 2H), 5.54 (s, 2H), 5.10 (spt, J=6.9 Hz, 1H), 4.40 (t, J=5.3 Hz, 1H), 4.17 (d, J=7.1 Hz, 2H), 3.88-3.97 (m, 2H), 3.40-3.47 (m, 2H), 2.45 (s, 3H), 1.70 (quin, J=6.9 Hz, 2H), 1.52 (d, J=6.9 Hz, 6H), 1.06-1.30 (m, 1H), 0.46-0.55 (m, 2H), 0.29-0.37 (m, 2H).

Example 14

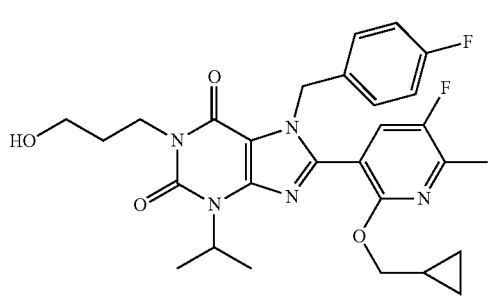

Example 14 was prepared in an analogous manner to Example 6 using intermediate 11.4.

MS (ESI+): (M+H)+ 541

HPLC: RT=0.83 min, Method G $^1$H NMR (DMSO-$d_6$) δ 7.74 (d, J=8.7 Hz, 1H), 6.96-7.09 (m, 4H), 5.52 (s, 2H), 5.09 (spt, J=6.9 Hz, 1H), 4.41 (t, J=5.1 Hz, 1H), 4.11 (d, J=7.1 Hz, 2H), 3.90-3.96 (m, 2H), 3.41-3.47 (m, 2H), 2.43 (d, J=3.0 Hz, 3H), 1.66-1.74 (m, 2H), 1.51 (d, J=6.9 Hz, 6H), 1.13-1.23 (m, 1H), 0.46-0.52 (m, 2H), 0.26-0.31 (m, 2H).

Example 15

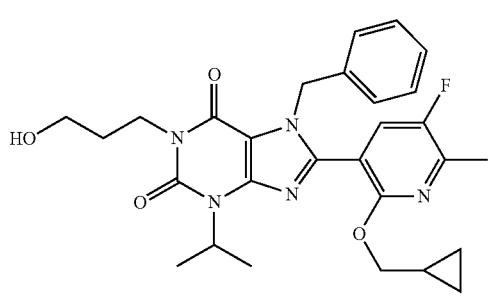

Example 15 was prepared in an analogous manner to Example 6 using intermediate 11.1.

MS (ESI+): (M+H)+ 522/523

HPLC: RT=0.83 min, Method G $^1$H NMR (DMSO-$d_6$) δ 7.73 (d, J=8.7 Hz, 1H), 7.18-7.25 (m, 3H), 6.90-6.98 (m, 2H), 5.55 (s, 2H), 5.09 (spt, J=6.9 Hz, 1H), 4.34-4.51 (m, 1H), 4.12 (d, J=7.1 Hz, 2H), 3.89-3.96 (m, 2H), 3.36-3.49 (m, 2H), 2.42 (d, J=3.0 Hz, 3H), 1.60-1.74 (m, 2H), 1.51 (d, J=6.9 Hz, 6H), 1.14-1.28 (m, 1H), 0.48-0.53 (m, 2H), 0.27-0.33 (m, 2H).

Example 16

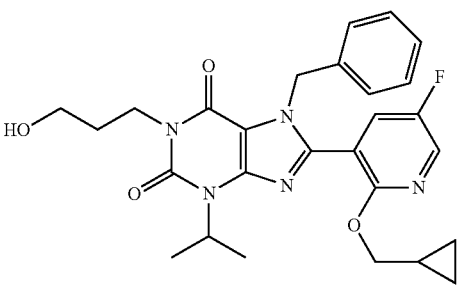

Example 16 was prepared in an analogous manner to Example 6 using intermediate 11.2.

MS (ESP): (M+H)+ 509

HPLC: RT=0.77 min, Method G $^1$H NMR (DMSO-$d_6$) δ 8.35 (d, J=3.0 Hz, 1H), 7.8 (dd, J=3.0, 8.1 Hz, 1H), 7.17-7.24 (m, 3H), 6.92 (dd, J=2.1, 7.4 Hz, 2H), 5.57 (s, 2H), 5.10 (spt, J=6.1 Hz, 1H), 4.41 (t, J=5.3 Hz, 1H), 4.12 (d, J=7.1 Hz, 2H), 3.91-3.97 (m, 2H), 3.42-3.48 (m, 2H), 1.67-1.75 (m, 2H), 1.52 (d, J=6.9 Hz, 6H), 1.13-1.24 (m, 1H), 0.46-0.53 (m, 2H), 0.26-0.34 (m, 2H).

Example 17

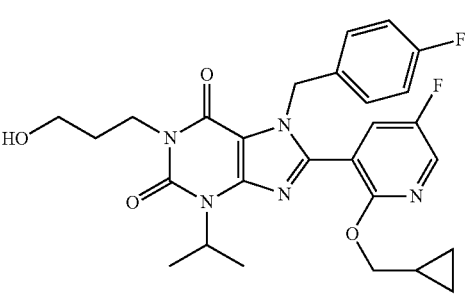

Example 17 was prepared in an analogous manner to Example 6 using intermediate 11.3.

MS (ESI+): (M+H)+ 527

HPLC: RT=0.77 min, Method G $^1$H NMR (DMSO-$d_6$) δ 8.36 (d, J=3.0 Hz, 1H), 7.85 (dd, J=3.0, 8.1 Hz, 1H), 6.95-7.08 (m, 4H), 5.53 (s, 2H), 5.09 (spt, J=6.9 Hz, 1H), 4.41 (t, J=5.3 Hz, 1H), 4.12 (d, J=7.1 Hz, 2H), 3.94 (t, J=7.4 Hz, 2H), 3.42-3.48 (m, 2H), 1.67-1.76 (m, 2H), 1.51 (d, J=6.9 Hz, 6H), 1.12-1.25 (m, 1H), 0.46-0.53 (m, 2H), 0.25-0.31 (m, 2H).

Example 18

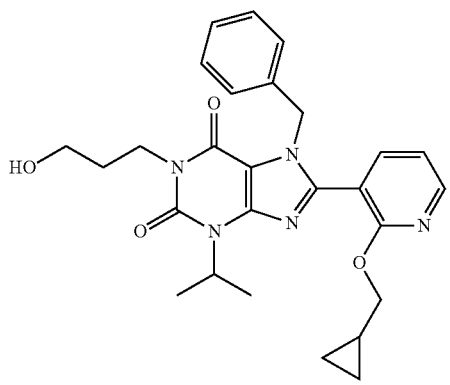 [SMILES: CC(C)n1c(=O)n(CCCO)c(=O)c2c1nc(-c1cccnc1OCC1CC1)n2Cc1ccccc1]

Example 18 was prepared in an analogous manner to Example 6 using intermediate 11.5.

MS (ESP): (M+H)+ 490.5

HPLC: RT=0.73 min, Method D $^1$H NMR (DMSO-d$_6$) δ 8.33 (dd, J=1.9, 4.9 Hz, 1H), 7.77 (dd, J=1.8, 7.3 Hz, 1H), 7.16-7.22 (m, 3H), 7.09 (dd, J=4.9, 7.3 Hz, 1H), 6.85-6.91 (m, 2H), 5.55 (s, 2H), 5.10 (spt, J=6.9 Hz, 1H), 4.41 (t, J=5.3 Hz, 1H), 4.18 (d, J=7.10 Hz, 2H), 3.94 (br t, J=7.3 Hz, 2H), 3.45 (q, J=6.3 Hz, 2H), 1.67-1.76 (m, 2H), 1.52 (d, J=6.9 Hz, 6H), 1.12-1.27 (m, 1H), 0.46-0.54 (m, 2H), 0.31 (q, J=4.7 Hz, 2H).

Example 19

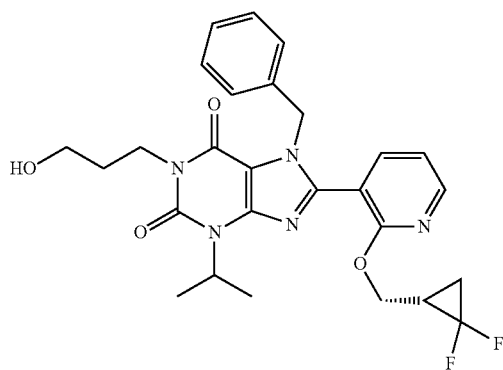

Example 19 was prepared in an analogous manner to Example 6 using intermediate 11.6.

MS (ESI+): (M+H)+ 526

HPLC: RT=0.99 min, Method F $^1$H NMR (DMSO-d$_6$) δ 8.36 (dd, J=1.9, 4.9 Hz, 1H), 7.82 (dd, J=1.9, 7.4 Hz, 1H), 7.13-7.23 (m, 4H), 6.88 (dd, J=2.0, 7.4 Hz, 2H), 5.51 (s, 2H), 5.10 (spt, J=6.9 Hz, 1H), 4.47-4.54 (m, 1H), 4.41 (t, J=5.3 Hz, 1H), 4.25-4.32 (m, 1H), 3.90-3.97 (m, 2H), 3.41-3.48 (m, 2H), 2.14-2.26 (m, 1H), 1.63-1.75 (m, 3H), 1.52 (d, J=6.9 Hz, 6H), 1.41-1.49 (m, 1H).

Example 20

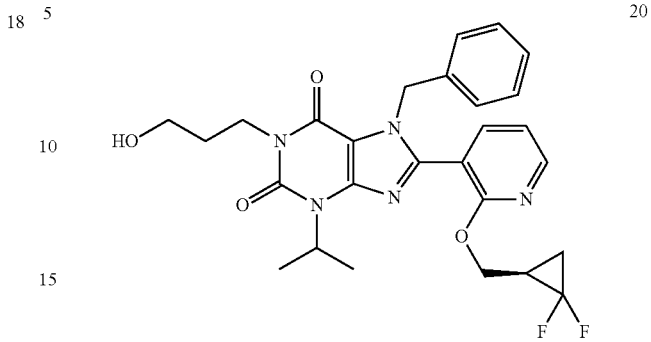

Example 20 was prepared in an analogous manner to Example 6 using intermediate 11.7.

MS (ESI+): (M+H)+ 527

HPLC: RT=0.95 min, Method F $^1$H NMR (DMSO-d$_6$) δ 8.36 (dd, J=1.9, 4.9 Hz, 1H), 7.82 (dd, J=1.9, 7.4 Hz, 1H), 7.13-7.23 (m, 4H), 6.88 (dd, J=2.0, 7.4 Hz, 2H), 5.51 (s, 2H), 5.10 (spt, J=6.9 Hz, 1H), 4.47-4.54 (m, 1H), 4.41 (t, J=5.3 Hz, 1H), 4.25-4.32 (m, 1H), 3.90-3.97 (m, 2H), 3.41-3.48 (m, 2H), 2.14-2.26 (m, 1H), 1.63-1.75 (m, 3H), 1.52 (d, J=6.9 Hz, 6H), 1.41-1.49 (m, 1H).

Example 21

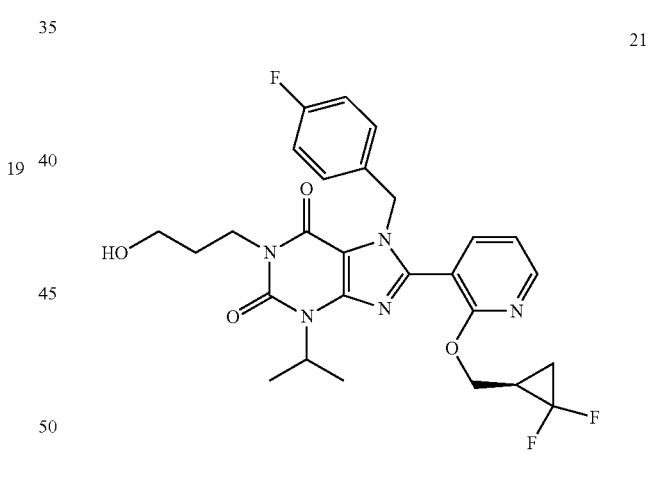

Example 21 was obtained by chiral separation of intermediate 12.1 (170 mg, 0.313 mmol) (Method E) and is the earlier eluting enantiomer. The absolute stereochemistry is not known and arbitrarily assigned. The other enantiomer is represented by Example 22.

MS (ESI+): (M+H)+ 544

RT=3.110 min, Method: E $^1$H NMR (DMSO-d$_6$) δ 8.37 (dd, J=1.9, 4.9 Hz, 1H), 7.82 (dd, J=1.9, 7.4 Hz, 1H), 7.16 (dd, J=5.0, 7.4 Hz, 1H), 7.04 (t, J=8.3 Hz, 2H), 6.90-6.96 (m, 2H), 5.49 (s, 2H), 5.09 (spt, J=6.9 Hz, 1H), 4.39-4.53 (m, 2H), 4.26-4.33 (m, 1H), 3.90-3.98 (m, 2H), 3.42-3.48 (m, 2H), 2.14-2.26 (m, 1H), 1.63-1.75 (m, 3H), 1.51 (d, J=6.9 Hz, 6H), 1.30-1.60 (m, 1H).

Example 22

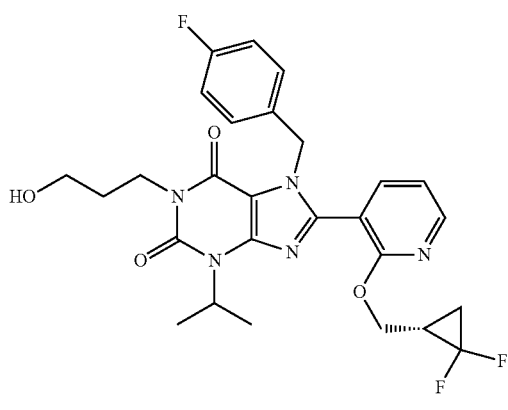

Example 22 was obtained by chiral separation of intermediate 12.1 (170 mg, 0.313 mmol) (Method E) and is the later eluting enantiomer. The absolute stereochemistry is not known and arbitrarily assigned. The other enantiomer is represented by Example 21.

MS (ESI$^+$): (M+H)$^+$ 544
RT=3.467 min, Method E
$^1$H NMR (DMSO-d$_6$) δ 8.37 (dd, J=1.9, 4.9 Hz, 1H), 7.82 (dd, J=1.9, 7.4 Hz, 1H), 7.16 (dd, J=5.0, 7.4 Hz, 1H), 7.04 (t, J=8.3 Hz, 2H), 6.90-6.96 (m, 2H), 5.49 (s, 2H), 5.09 (spt, J=6.9 Hz, 1H), 4.39-4.53 (m, 2H), 4.26-4.33 (m, 1H), 3.90-3.98 (m, 2H), 3.42-3.48 (m, 2H), 2.14-2.26 (m, 1H), 1.63-1.75 (m, 3H), 1.51 (d, J=6.9 Hz, 6H), 1.30-1.60 (m, 1H).

Example 23

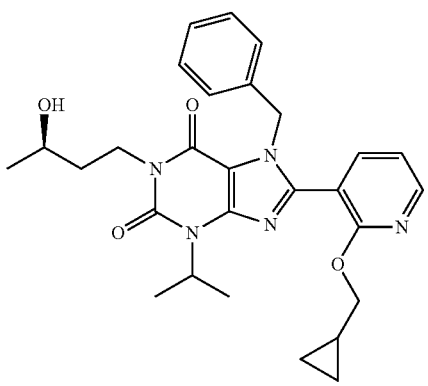

To a mixture of intermediate 5.17 (60.0 mg, 0.139 mmol) in DMF (1.50 mL) was added K$_2$CO$_3$ (38.0 mg, 0.278 mmol). Then intermediate 13.1 (37.0 mg, 0.153 mmol) dissolved in DMF (1.50 mL) was added and the mixture was stirred at 110° C. for 3 h and 20 min. The mixture was cooled rt, H$_2$O was added and extracted twice with EtOAc. The combined organic layers were washed with H$_2$O, dried, filtered off, concentrated in vacuo and purified by chromatography (59.4 mg, 85%).

MS (ESI$^+$): (M+H)$^+$ 504
HPLC: RT=0.75 min, Method G
$^1$H NMR (DMSO-d$_6$) δ 8.33 (dd, J=2.0, 5.0 Hz, 1H), 7.77 (dd, J=2.0, 7.4 Hz, 1H), 7.16-7.23 (m, 3H), 7.09 (dd, J=5.0, 7.4 Hz, 1H), 6.86-6.92 (m, 2H), 5.55 (s, 2H), 5.10 (spt, J=6.9 Hz, 1H), 4.47 (d, J=4.6 Hz, 1H), 4.18 (d, J=7.1 Hz, 2H), 3.98-4.06 (m, 1H), 3.82-3.90 (m, 1H), 3.61-3.70 (m, 1H), 1.60-1.68 (m, 1H), 1.52 (d, J=6.9 Hz, 6H), 1.17-1.28 (m, 1H), 1.09 (d, J=6.1 Hz, 3H), 0.46-0.56 (m, 2H), 0.27-0.37 (m, 2H).

Example 24

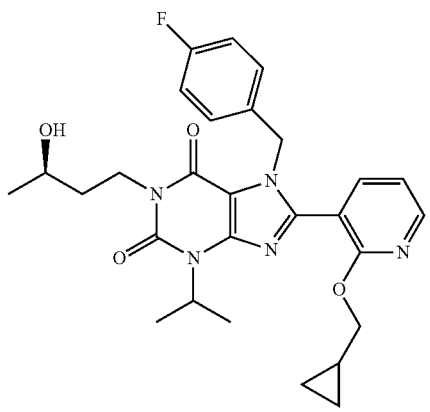

To a mixture of intermediate 5.18 (60.0 mg, 0.133 mmol) in DMF (1.50 mL) was added K$_2$CO$_3$ (37.0 mg, 0.267 mmol). Then intermediate 13.1 (36.0 mg, 0.147 mmol) dissolved in DMF (1.50 mL) was added and the mixture was stirred at 110° C. for 3 h and 40 min. The mixture was cooled to rt, H$_2$O was added and extracted with EtOAc. The combined organic layers were washed with H$_2$O, dried, filtered off, concentrated in vacuo and purified by chromatography (58.7 mg, 84%).

MS (ESI$^+$): (M+H)$^+$ 522
HPLC: RT=0.76 min, Method G
$^1$H NMR (DMSO-d$_6$) δ 8.34 (dd, J=2.0, 5.0 Hz, 1H), 7.78 (dd, J=2.0, 7.4 Hz, 1H), 7.01-7.12 (m, 3H), 6.91-6.96 (m, 2H), 5.52 (s, 2H), 5.09 (spt, J=6.9 Hz, 1H), 4.47 (d, J=4.7 Hz, 1H), 4.17 (d, J=7.1 Hz, 2H), 3.99-4.06 (m, 1H), 3.83-3.90 (m, 1H), 3.62-3.70 (m, 1H), 1.55-1.68 (m, 2H), 1.51 (d, J=6.9 Hz, 6H), 1.16-1.28 (m, 1H), 1.09 (d, J=6.2 Hz, 3H), 0.45-0.55 (m, 2H), 0.25-0.36 (m, 2H).

Example 25

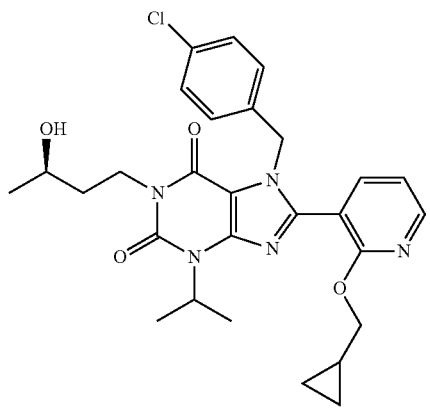

To a mixture of intermediate 5.6 (75.0 mg, 0.161 mmol) in DMF (1.50 mL) was added K$_2$CO$_3$ (44.0 mg, 0.322 mmol). Then intermediate 13.1 (43.0 mg, 0.177 mmol) dissolved in DMF (1.50 mL) was added and the mixture was stirred at 110° C. for 2 h and 30 min. The mixture was cooled to rt, H$_2$O was added and extracted with EtOAc. The combined organic layers were washed with H$_2$O, dried, filtered off, concentrated in vacuo and purified by chromatography (60.3 mg, 70%).

MS (ESI$^+$): (M+H)$^+$ 538

HPLC: RT=0.80 min, Method G $^1$H NMR (DMSO-d$_6$) δ 8.34 (dd, J=2.0, 4.94 Hz, 1H), 7.79 (dd, J=2.0, 7.4 Hz, 1H), 7.26-7.29 (m, 2H), 7.11 (dd, J=5.0, 7.4 Hz, 1H), 6.90-6.94 (m, 2H), 5.52 (s, 2H), 5.10 (spt, J=6.9 Hz, 1H), 4.46 (d, J=4.6 Hz, 1H), 4.15 (d, J=7.1 Hz, 2H), 3.97-4.06 (m, 1H), 3.81-3.89 (m, 1H), 3.61-3.70 (m, 1H), 1.55-1.67 (m, 2H), 1.52 (d, J=6.9 Hz, 6H), 1.14-1.24 (m, 1H), 1.09 (d, J=6.2 Hz, 3H), 0.48-0.53 (m, 2H), 0.27-0.31 (m, 2H).

The invention claimed is:

1. A compound, wherein the compound is:

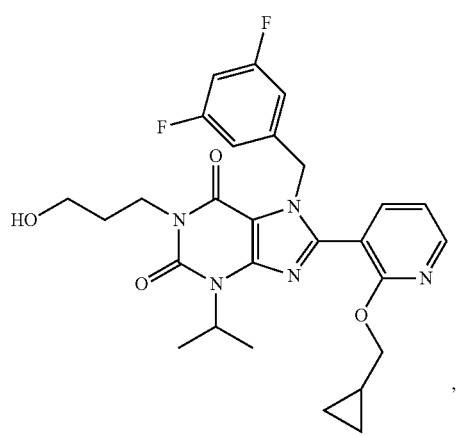

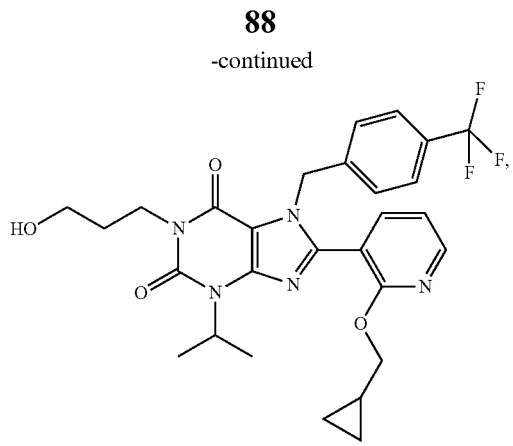

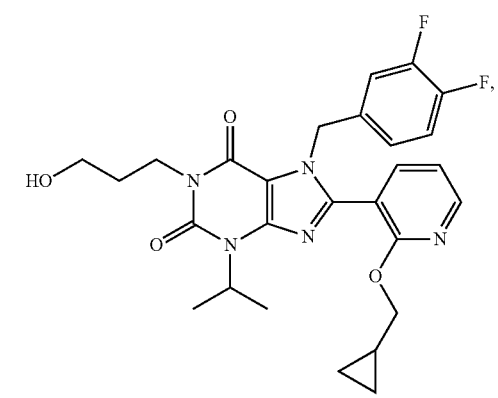

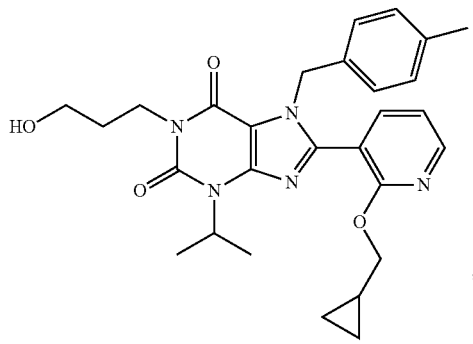

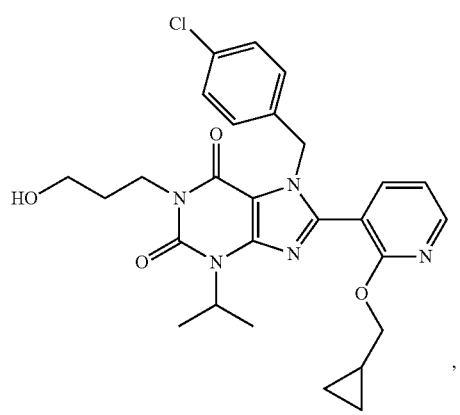

89
-continued
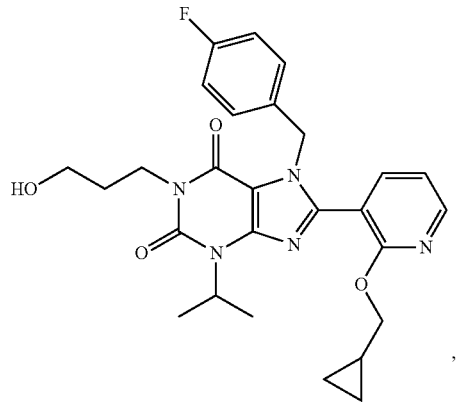
,
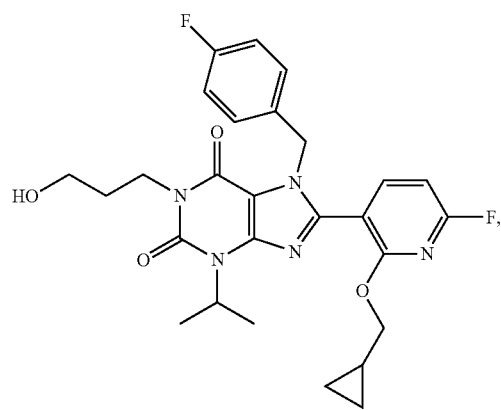
,
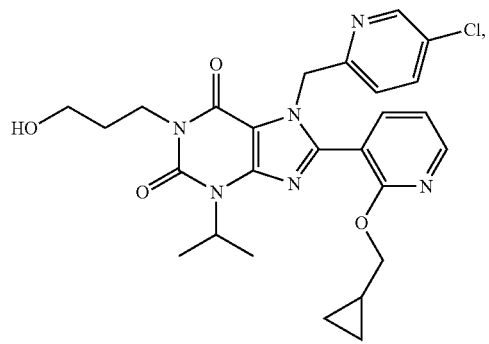
,
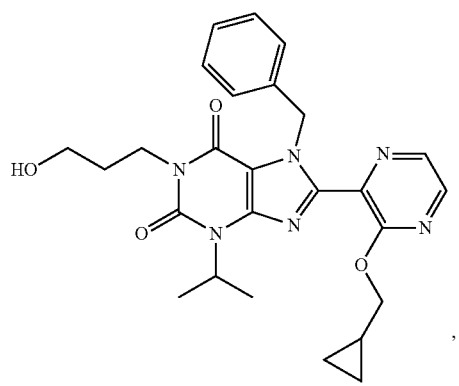
,
90
-continued
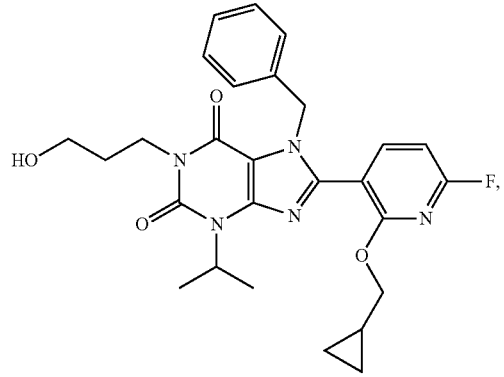
,
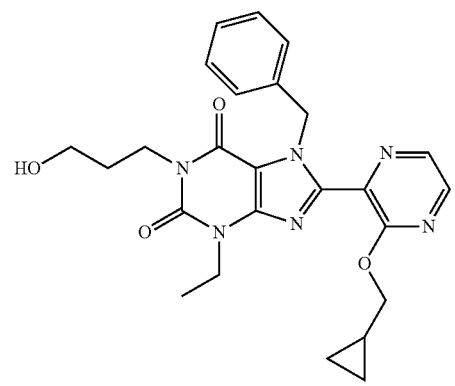
,
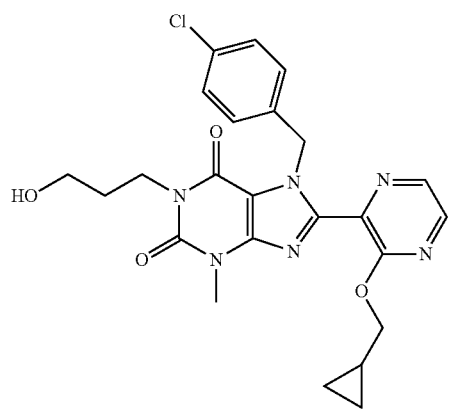
,
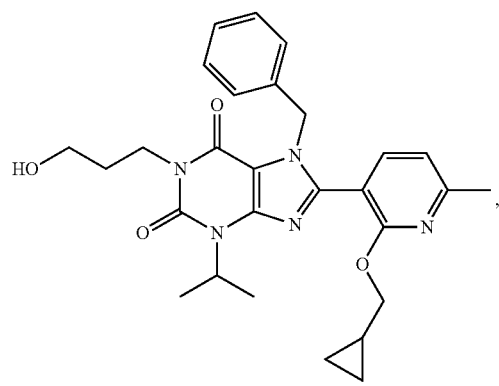
,

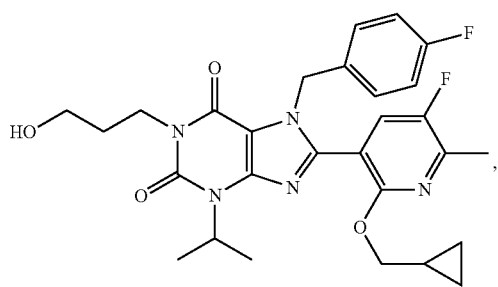
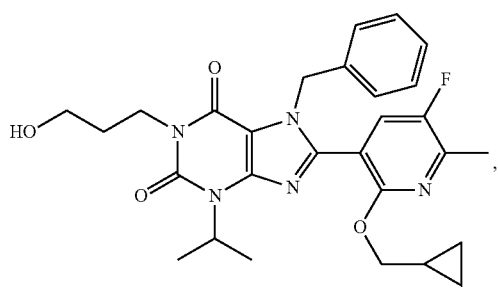
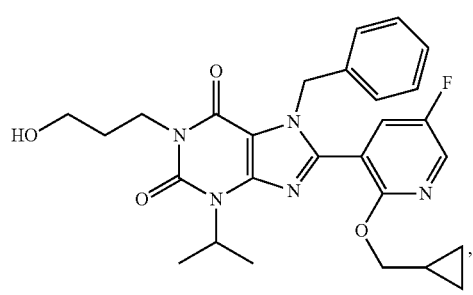
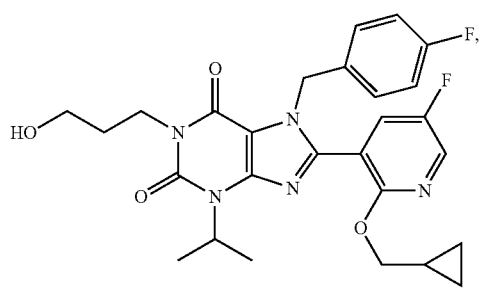
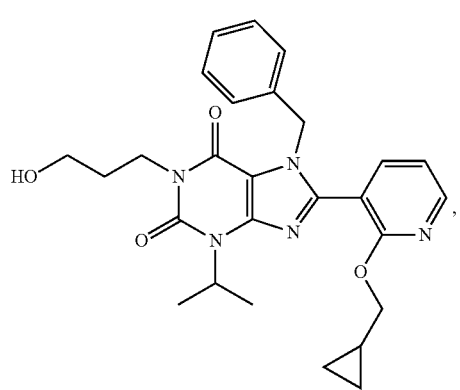
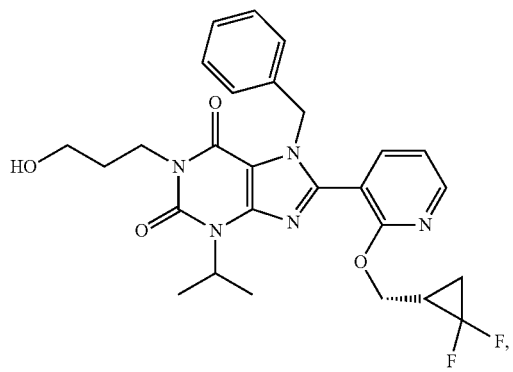
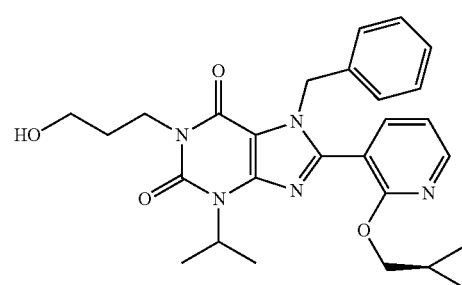
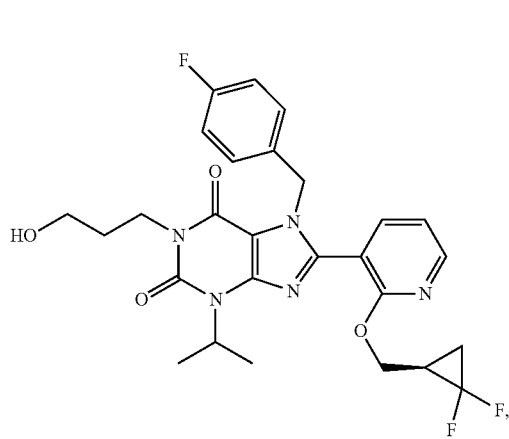
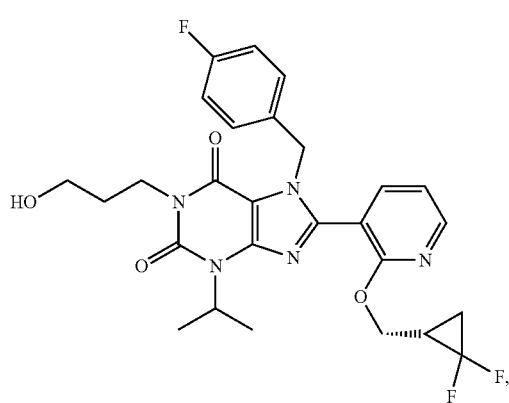

-continued

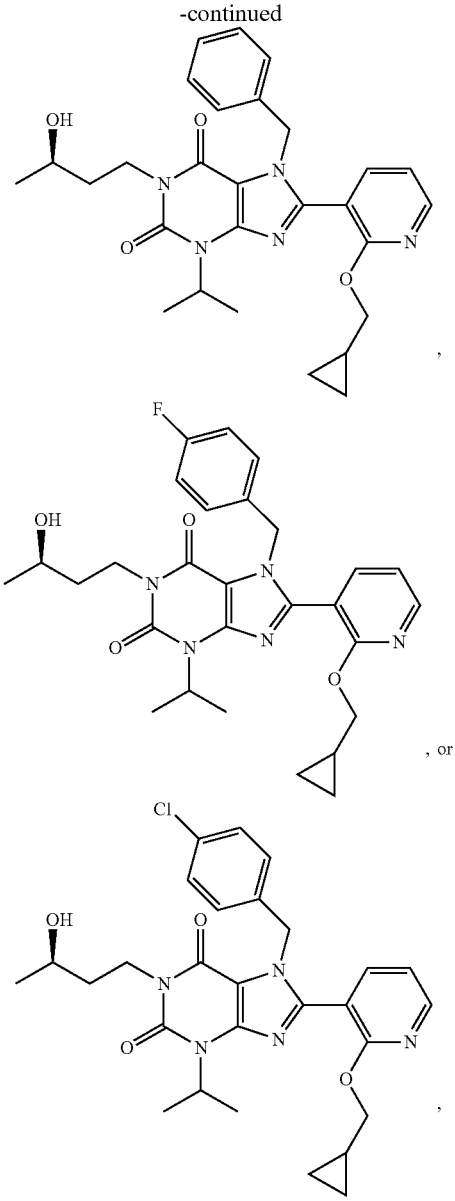

,

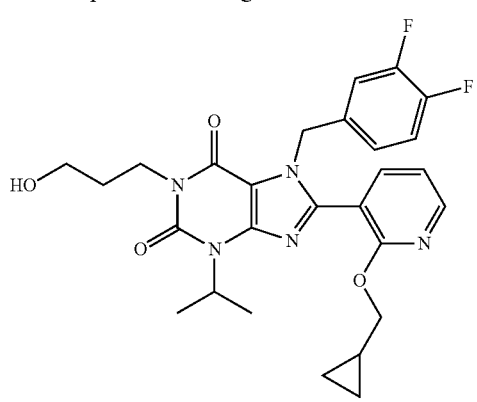

or a pharmaceutically acceptable salt thereof.

2. The compound according to claim 1:

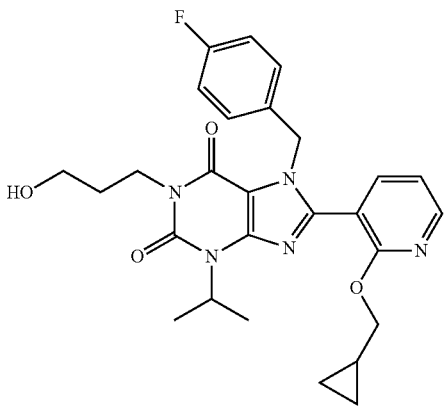

or a pharmaceutically acceptable salt thereof.

3. The compound according to claim 1:

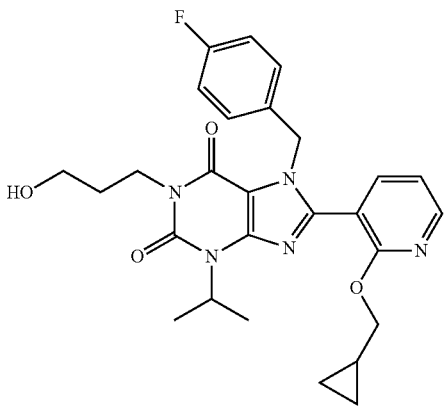

or a pharmaceutically acceptable salt thereof.

4. The compound according to claim 1:

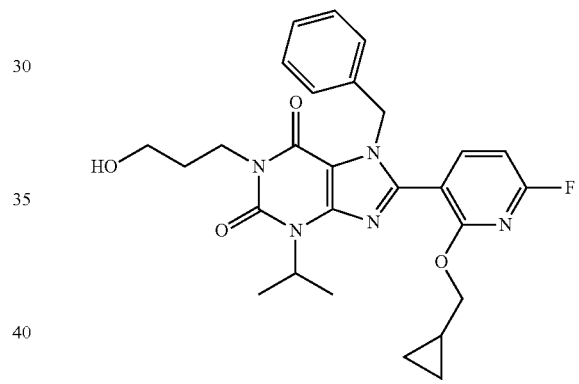

or a pharmaceutically acceptable salt thereof.

5. The compound according to claim 1:

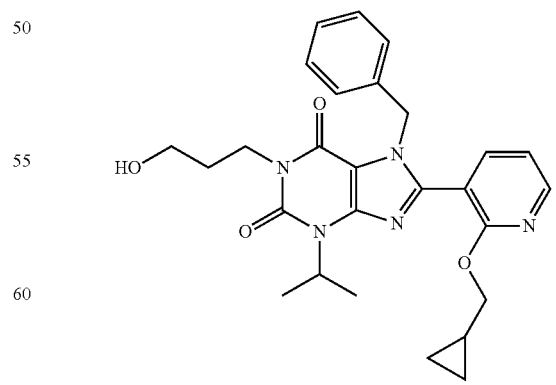

or a pharmaceutically acceptable salt thereof.

6. The compound according to claim 1:
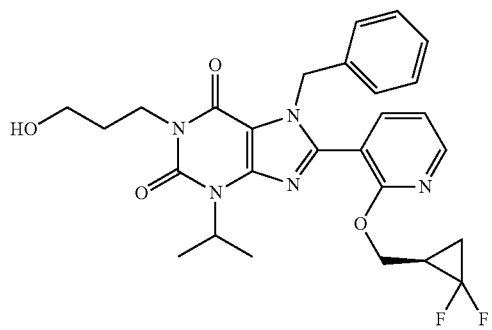 [SMILES: CC(C)n1c(=O)n(CCCO)c(=O)c2c1nc(-c1cccnc1OC[C@H]1CC1(F)F)n2Cc1ccccc1]
or a pharmaceutically acceptable salt thereof.
7. The compound according to claim 1:
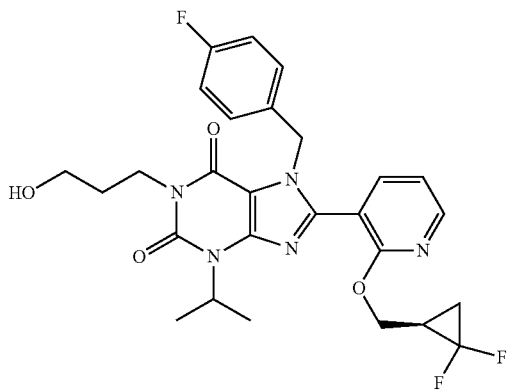 [SMILES: CC(C)n1c(=O)n(CCCO)c(=O)c2c1nc(-c1cccnc1OC[C@H]1CC1(F)F)n2Cc1ccc(F)cc1]
or a pharmaceutically acceptable salt thereof.
8. The compound according to claim 1:
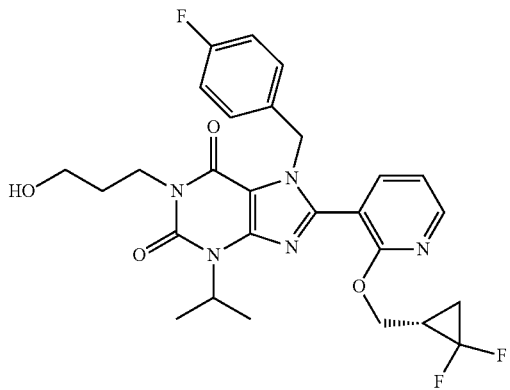 [SMILES: CC(C)n1c(=O)n(CCCO)c(=O)c2c1nc(-c1cccnc1OC[C@@H]1CC1(F)F)n2Cc1ccc(F)cc1]
or a pharmaceutically acceptable salt thereof.
9. The compound according to claim 1:
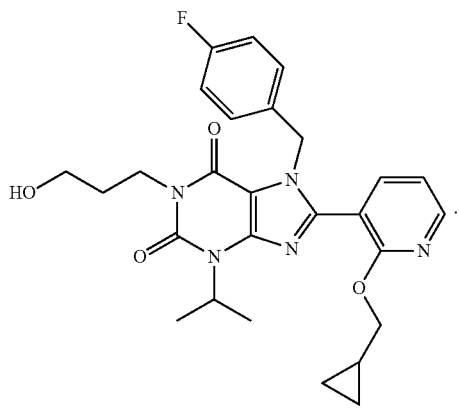 [SMILES: CC(C)n1c(=O)n(CCCO)c(=O)c2c1nc(-c1cccnc1OCC1CC1)n2Cc1ccc(F)cc1]
10. The compound according to claim 1:
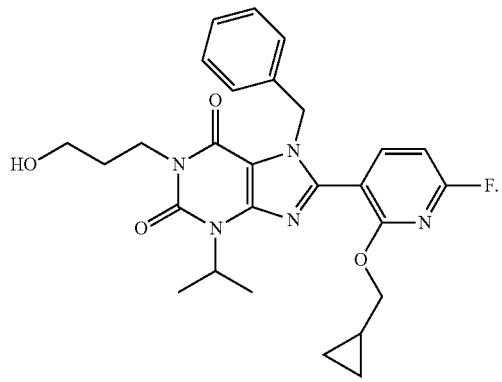 [SMILES: CC(C)n1c(=O)n(CCCO)c(=O)c2c1nc(-c1ccc(F)nc1OCC1CC1)n2Cc1ccccc1]
11. The compound according to claim 1:

12. The compound according to claim 1:

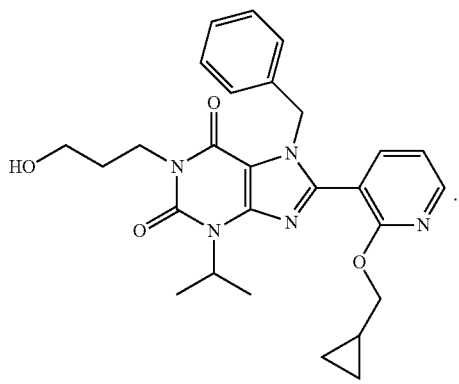 [SMILES: CC(C)n1c(=O)n(CCCO)c(=O)c2c1nc(-c1cccnc1OCC1CC1)n2Cc1ccccc1]

13. The compound according to claim 1:

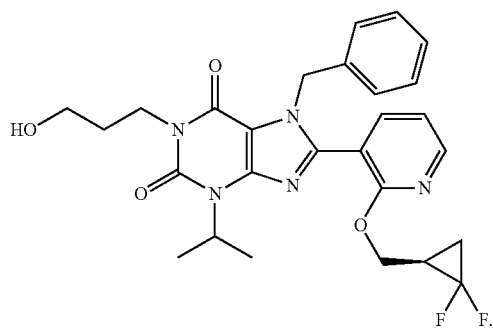 [SMILES: CC(C)n1c(=O)n(CCCO)c(=O)c2c1nc(-c1cccnc1OC[C@H]1CC1(F)F)n2Cc1ccccc1]

14. The compound according to claim 1:

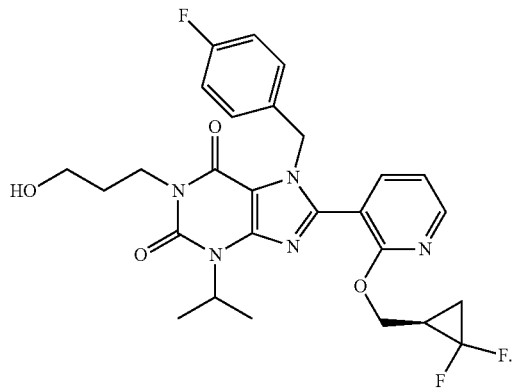 [SMILES: CC(C)n1c(=O)n(CCCO)c(=O)c2c1nc(-c1cccnc1OC[C@H]1CC1(F)F)n2Cc1ccc(F)cc1]

15. The compound according to claim 1:

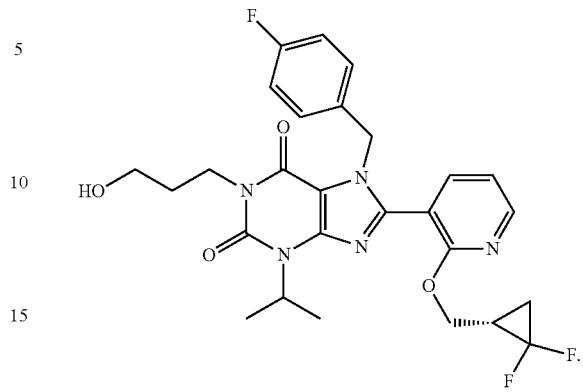

16. A pharmaceutical composition comprising a compound according to claim 1 and a pharmaceutically acceptable excipient.

17. A method for treating a TRPC5 mediated disorder in a subject, the method comprising administering to the subject an effective amount of a compound of claim 1, wherein the TRPC5 mediated disorder is selected from diseases associated with dysregulated emotional processing, anxiety and fear-related disorders, memory disorders, disorders associated with impaired impulse control and addiction, Alzheimer's disease, Parkinson's disease, Huntington's disease, amyotrophic lateral sclerosis, and brain disorders caused by trauma, insults, or aging.

18. A method for treating a TRPC5 mediated disorder in a subject, the method comprising administering to the subject an effective amount of a compound of claim 1, wherein the TRPC5 mediated disorder is borderline personality disorder or depressive disorders, major depression, major depressive disorder, psychiatric depression, dysthymia, postpartum depression, bipolar disorders, post-traumatic stress disorder, panic disorder, agoraphobia, social phobias, generalized anxiety disorder, panic disorder, social anxiety disorder, obsessive compulsive disorder, separation anxiety, Alzheimer's disease, amnesia, aphasia, brain injury, brain tumor, chronic fatigue syndrome, Creutzfeldt-Jakob disease, dissociative amnesia, fugue amnesia, Huntington's disease, learning disorders, sleeping disorders, multiple personality disorder, pain, post-traumatic stress disorder, schizophrenia, sports injuries, stroke, Wernicke-Korsakoff syndrome, Alzheimer's disease, Parkinson's disease, Huntington's disease, or amyotrophic lateral sclerosis.

* * * * *